United States Patent
Gobbi et al.

(10) Patent No.: US 7,858,630 B2
(45) Date of Patent: Dec. 28, 2010

(54) $D_3$ AND 5-HT$_{2A}$ RECEPTOR MODULATORS

(75) Inventors: Luca Gobbi, Muttenz (CH); Georg Jaeschke, Basel (CH); Rosa Maria Rodriguez Sarmiento, Basel (CH); Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/560,459

(22) Filed: Sep. 16, 2009

(65) Prior Publication Data

US 2010/0075983 A1   Mar. 25, 2010

(30) Foreign Application Priority Data

Sep. 22, 2008 (EP) ................... 08164802

(51) Int. Cl.
A61K 31/496 (2006.01)
C07D 261/20 (2006.01)
C07D 413/12 (2006.01)
(52) U.S. Cl. .................. 514/254.04; 544/368
(58) Field of Classification Search ............... None
See application file for complete search history.

(56) References Cited

FOREIGN PATENT DOCUMENTS

| WO | WO 95/11680 | 5/1995 |
|----|-------------|--------|
| WO | WO 02/066446 | 8/2002 |
| WO | WO 2004/026864 | 4/2004 |
| WO | WO 2004/100954 | 11/2004 |
| WO | WO 2004/100955 | 11/2004 |
| WO | WO 2007/093540 | 8/2007 |
| WO | WO 2009/013212 | 1/2009 |

OTHER PUBLICATIONS

Roth et al., Nat. Rev. Drug. Discovery vol. 3 pp. 353-359 (2004).
Lieberman et al., N. Engl. J. Med. vol. 353, pp. 1209-1223 (2005).
Missale et al., Physiol. Rev. vol. 78 pp. 189-225 (1998).
Gurevich E. V., Neuropsychopharmacology vol. 20 pp. 60-80 (1999).
Joyce J. N., Drug Discovery Today 1, vol. 10, No. 13 pp. 917-925 (2005).
Gurevich E.V., Arch. Gen. Psychiatry vol. 54 pp. 225-232 (1997).
Leikin et al., Med. Toxicol. Adverse Drug Exp. vol. 4 pp. 324-350 (1989).
Harrison P. J., Br. J. Psychiatry Suppl. 38 pp. 12-22 (1999).
Barnes N. M., Neuropharmacology vol. 38 pp. 1083-1152 (1999).
Pompeiano et al., Brain Res. Mol. vol. 23 pp. 163-178 (1994).
Roth et al., Pharmacol. Ther. vol. 79 pp. 231-257 (1998).
Spurlock et al., Mol. Psychiatry vol. 3 pp. 42-49 (1998).
Arranz et al., Lancet vol. 355 pp. 1615-1616 (2000).
Porras et al., Neuropsychopharmacology vol. 26 pp. 311-324 (2002).
DeAngelis L., Curr. Opin. Investig. Drugs. vol. 3 pp. 106-112 (2002).
Meltzer et al., J. Pharmacol. Exp. Ther. vol. 251 pp. 238-246 (1989).
Wustrow, et al., Journal of Medicinal Chemistry vol. 41 pp. 760-771 (1998).
Pazos et al., (1987), Neuroscience, pp. 123-139.
Reavill et al., (2000), JPET vol. 294, pp. 1154-1165.
Millan, M. J. (2005), Drug Discovery Today, pp. 917-925.
Vovel et al. (2002) J. Neurosci. vol. 22, pp. 9595-9603.
Campos et al. (2003) Soc. Neurosci. Abstr. 322.8.
Ashby (2003) Synapse vol. 48 pp. 154-156.
Dresher K. (2002) Am. Soc. Neurosci. Abstr. 894.6.

Primary Examiner—Emily Bernhardt
(74) Attorney, Agent, or Firm—George W. Johnston; Patricia S. Rocha-Tramaloni; Kimberly J. Prior

(57) ABSTRACT

The present invention provides compounds of the general formula (I)

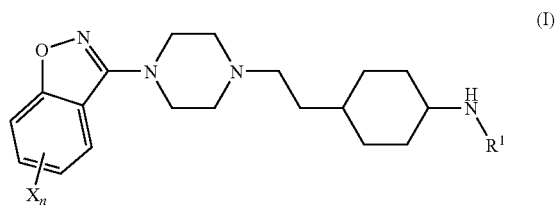

wherein X, n and $R^1$ are as described herein, as well as pharmaceutically acceptable salts and esters thereof, methods for their manufacture, pharmaceutical compositions containing them and their use as medicaments. The active compounds of the present invention are dual modulators of the serotonin 5-HT$_{2a}$ and dopamine $D_3$ receptors, useful in the treatment and/or the prevention of cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions.

36 Claims, No Drawings

D₃ AND 5-HT$_{2A}$ RECEPTOR MODULATORS

PRIORITY TO RELATED APPLICATION(S)

This application claims the benefit of European Patent Application No. 08164802.4, filed Sep. 22, 2008, which is hereby incorporated by reference in its entirety.

BACKGROUND OF THE INVENTION

Schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M. (2000) Essential Psychopharmacology. Neuroscientific Basis and Practical Applications. Cambridge University Press, second edition, Cambridge, UK). The different categories and the clinical features of the disorder are defined in diagnostic schemes such as DSM-IV (Diagnostic and statistical manual of mental disorders, 4$^{th}$ edition) or ICD-10 (International classification of diseases, 10$^{th}$ edition). Currently used medications to treat schizophrenia, bipolar mania and other psychoses, include antipsychotics both typical ($D_2/D_3$ preferring) or the more recent atypicals, which exhibit polypharmacology interacting at multiple receptors (eg., $D_1$, $D_2$, $D_3$, $D_4$, 5-HT$_{1A}$, 5-HT$_{2A}$, 5-HT$_{2C}$, $H_1$, $M_1$, $M_2$, $M_4$, etc; Roth, B. L. et al. (2004) Magic shotguns versus magic bullets: selectively non-selective drugs for mood disorders and schizophrenia. Nat. Rev. Drug Discov. 3, 353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). Furthermore, patient compliance is compromised by prevalent side effects such as weight gain, extrapyramidal symptoms (EPS), and cardiovascular effects (Lieberman, J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). In the current invention, compounds with high affinity and greater selectivity for $D_3$ and 5-HT$_{2A}$ receptors are described and are proposed to treat psychoses and other diseases, with fewer associated side affects.

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha I}$ (Missale, C. et al. (1998) Dopamine receptors: from structure to function. Physiol. Rev. 78, 189-225). The $D_3$ dopamine receptor is most highly expressed in the nucleus accumbens (Gurevich, E. V., Joyce, J. N. (1999) Distribution of dopamine D3 receptor expressing neurons in the human forebrain: comparison with D2 receptor expressing neurons. Neuropsychopharmacology 20, 60-80), and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce, J. N. and Millan, M. J., (2005) Dopamine D3 receptor antagonists as therapeutic agents. Drug Discovery Today, 1 July, Vol. 10, No. 13, 917-25), while these antagonists spare the $D_2$ modulated striatal extrapyramidal system (associated with EPS induction). In addition, it has been reported that drug naive schizophrenic patients show altered levels of $D_3$ receptor expression (Gurevich, E. V. et al. (1997) Mesolimbic dopamine D3 receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

The neurotransmitter serotonin is implicated in several psychiatric conditions including schizophrenia (Kandel, E. R. et al. (eds.; 2000) Principles of Neural Science, 3$^{rd}$ edition Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin, J. B. et al. (1989) Clinical features and management of intoxication due to hallucinogenic drugs. Med. Toxicol. Adverse Drug Exp. 4, 324-350). Furthermore, altered brain distribution of serotonin receptors as well as an altered serotonergic tone, have been detected in schizophrenic patients (Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22). In mammals serotonin exerts its biological activities through a family of 14 5-HT GPCRs (Barnes, N. M., Sharp, T. (1999) A review of central 5-HT receptors and their function. Neuropharmacology 38, 1083-1152). The 5-HT$_{2A}$ receptor is most prominently expressed in the prefrontal cortex and at lower levels in the basal ganglia and the hippocampus in human brain (Pompeiano, M. et al. (1994) Distribution of the serotonin 5-HT2 receptor family mRNAs: comparison between 5-HT2A and 5-HT2C receptors. Brain Res. Mol. Brain. Res. 23, 163-178; Pazos, A., Probst, A., Palacios, J. M. (1987) Serotonin receptors in the human brain—IV. Autoradiographic mapping of serotonin-2 receptors. Neuroscience 21, 123-139), and is coupled predominantly to the G-protein $G_{\alpha q}$ (Roth, B. L. et al. (1998) 5-Hydroxytryptamine-2-family receptors (5-hydroxytryptamine2A, 5-hydroxytryptamine2B, 5-hydroxytryptamine2C): where structure meets function. Pharmacol. Ther. 79, 231-257). Genetic linkage studies of a 5-HT$_{2A}$ polymorphism to schizophrenia (Spurlock, G. et al. (1998) A family based association study of T102C polymorphism in 5HT2A and schizophrenia plus identification of new polymorphisms in the promoter. Mol. Psychiatry. 3, 42-49), as well as responsiveness to antipsychotic drugs (Arranz, M. J. et al. (2000) Pharmacogenetic prediction of clozapine response. Lancet 355, 1615-1616), further suggests a role for the 5-HT$_{2A}$ receptor both in the treatment and pathology of psychosis. In addition, dopaminergic neurotransmission appears to be under the afferent regulation of the 5-HT$_{2A}$ receptor (Porras, G. et al. 5-HT2A and 5-HT2C/2B receptor subtypes modulate dopamine release induced in vivo by amphetamine and morphine in both the rat nucleus accumbens and striatum. Neuropsychopharmacology 26, 311-324-2002). Overall 5-HT$_{2A}$ receptor antagonists are proposed to be suitable for the treatment of disorders associated with dysfunctional dopaminergic systems. Moreover, 5-HT$_{2A}$ receptor antagonism has been recognized as beneficial for the treatment of psychosis (reviewed in de Angelis, L. (2002) 5-HT2A antagonists in psychiatric disorders. Curr. Opin. Investig. Drugs 3, 106-112) and indeed is one of the defining features of so-called atypical antipsychotic drugs which are characterized by a relatively high affinity for the 5-HT$_{2A}$-relative to the D$_2$ receptor (Meltzer, H. Y. et al. (1989) Classification of typical and atypical antipsychotic drugs on the basis of dopamine D-1, D-2 and serotonin2 pKi values. J. Pharmacol. Exp. Ther. 251, 238-246).

SUMMARY OF THE INVENTION

The present invention provides compounds of formula (I)

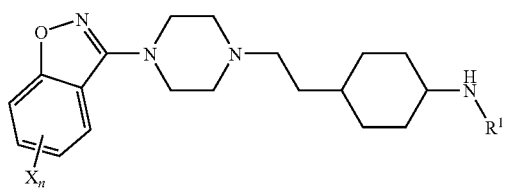

(I)

wherein:

X is independently halogen or C$_{1-6}$-alkyl;

n is 0, 1, or 2;

R$^1$ is —COR$^2$ or —SO$_2$—C$_{1-6}$-alkyl;

R$^2$ is C$_{1-6}$-alkyl, C$_{1-6}$-haloalkyl, C$_{1-6}$-hydroxyalkyl, C$_{1-6}$-alkoxy, 3 to 10 membered cycloalkyl, 4 to 10 membered heterocycloalkyl, or 5 to 10 membered heteroaryl, each of which is optionally substituted by one or more substituents selected from the group consisting of:

halo, hydroxy,

C$_{1-6}$-alkyl,

C$_{1-6}$-haloalkyl,

C$_{1-6}$-hydroxyalkyl,

C$_{1-6}$-alkoxy,

C$_{1-6}$-alkoxy optionally substituted by one or more R$^a$,

—S—C$_{1-6}$-alkyl,

—SO$_2$—C$_{1-6}$-alkyl,

—CONH$_2$,

—CHO, 3 to 10 membered cycloalkyl optionally substituted by one or more R$^a$, 4 to 10 membered heterocycloalkyl optionally substituted by one or more R$^a$, and 5 to 10 membered heteroaryl optionally substituted by one or more R$^a$;

wherein R$^a$ is selected from the group consisting of:

halo, hydroxy,

C$_{1-6}$-alkyl,

C$_{1-6}$-hydroxyalkyl,

C$_{1-6}$-haloalkyl, and

C$_{1-6}$-alkoxy;

as well as pharmaceutically acceptable salts thereof.

Compounds of formula (I) according to the invention are dual modulators of the serotonin 5-HT$_{2a}$ and dopamine D$_3$ receptors.

The compounds of the invention have high affinity for the dopamine D$_3$ and serotonin (5-Hydroxytryptamine; 5-HT) 5-HT$_{2A}$ receptors and are effective in the treatment of psychotic disorders, as well as other diseases such as depression and anxiety, drug dependence, dementias and memory impairment. Psychotic disorders encompass a variety of diseases, which include schizophrenia, schizoaffective disorders, bipolar disease, mania, psychotic depression, and other psychoses involving paranoia and delusions.

As mentioned hereinabove, the compounds of the invention have high affinity for the dopamine D$_3$ and serotonin 5-HT$_{2A}$ receptors and are expected to be effective in the treatment of psychotic disorders which include schizophrenia, schizoaffective disorders, bipolar disease, mania, psychotic depression, and other psychoses involving paranoia and delusions (Reavill-C, et al. (2000) Pharmacological actions of a novel, high-affinity, and selective human dopamine D3 receptor antagonist, SB-277011-A. JPET 294:1154-1165; Harrison, P. J. (1999) Neurochemical alterations in schizophrenia affecting the putative receptor targets of atypical antipsychotics. Focus on dopamine (D1, D3, D4) and 5-HT2A receptors. Br. J. Psychiatry Suppl. 38, 12-22; de Angelis, L. (2002) 5-HT2A antagonists in psychiatric disorders. Curr. Opin. Investig. Drugs 3, 106-112; Joyce, J. N. and Millan, M. J., (2005) Dopamine D3 receptor antagonists as therapeutic agents. Drug Discovery Today, 1 July, Vol. 10, No. 13, P. 917-25); drug dependency and abuse and withdrawal (Vorel, S. R. et al. (2002) Dopamine D3 receptor antagonism inhibits cocaine-seeking and cocaine-enhanced brain reward in rats. J. Neurosci., 22, 9595-9603; Campos, A. C. et al. (2003) The dopamine D3 receptor antagonist SB277011A antagonizes nicotine-enhanced brain-stimulation reward in rat. Soc. Neurosci. Abstr., 322.8; Ashby, et al. (2003) Acute administration of the selective D3 receptor antagonist SB-277011-A blocks the acquisition and expression of the conditioned place preference response to heroin in male rats. Synapse, 48, 154-156); anxiety, and depression (Reavill-C et al. (2000) Pharmacological actions of a novel, high-affinity, and selective human dopamine D3 receptor antagonist, SB-277011-A. JPET 294: 1154-1165; Drescher, K. et al. (2002) In vivo effects of the selective dopamine D3 receptor antagonist A-437203. Am. Soc. Neurosci. 894.6).

DETAILED DESCRIPTION OF THE INVENTION

Unless otherwise indicated, the following definitions are set forth to illustrate and define the meaning and scope of the various terms used to describe the invention herein. The following definitions of the terms apply irrespective of whether the terms in question appear alone or in combination.

The term "substituted," unless specifically defined otherwise, means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents.

When indicating the number of substituents, the term "one or more" means from one substituent to the highest possible number of substitution, i.e. replacement of one hydrogen up to replacement of all hydrogens by substituents. Thereby, one, two or three substituents are preferred.

The term "pharmaceutically acceptable esters" embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

As used herein, the term "$C_{1-6}$-alkyl" denotes monovalent linear or branched saturated hydrocarbon moiety, consisting solely of carbon and hydrogen atoms, having from 1 to 6 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms. Particularly preferred $C_{1-6}$-alkyl are methyl, ethyl and n-propyl. Most preferred is methyl and ethyl.

The term "$C_{1-6}$-alkoxy" denotes a group —O—R' wherein R' is $C_{1-6}$-alkyl as defined above. Preferred $C_{1-6}$-alkoxy are methoxy, ethoxy and isopropoxy. Most preferred is methoxy.

The term "halo or halogen" denotes chloro, iodo, fluoro and bromo. Preferred halo are fluoro, chloro and bromo, more preferred are fluoro and chloro. Most preferred is fluoro.

The term "$C_{1-6}$-haloalkyl" denotes an $C_{1-6}$-alkyl group as defined above wherein at least one of the hydrogen atoms of the alkyl group is replaced by a halogen atom, preferably fluoro or chloro, most preferably fluoro. Examples of $C_{1-6}$-haloalkyl include but are not limited to methyl, ethyl, propyl, isopropyl, isobutyl, sec-butyl, tert-butyl, pentyl or n-hexyl wherein one or more hydrogen atoms are replaced by Cl, F, Br or I atom(s), as well as those $C_{1-6}$-haloalkyl groups specifically illustrated by the examples herein below. Among the preferred $C_{1-6}$-haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl. Most preferred are 3,3,3-trifluoropropyl and 2,2,2-trifluoroethyl.

The term "$C_{1-6}$-hydroxyalkyl" denotes an $C_{1-6}$-alkyl group as defined above wherein at least one of the hydrogen atoms of the alkyl group is replaced by a hydroxy group. Examples of $C_{1-6}$-hydroxyalkyl include but are not limited to methyl, ethyl, propyl, isopropyl, isobutyl, sec-butyl, tert-butyl, pentyl or n-hexyl wherein one or more hydrogen atoms are replaced by OH, as well as those $C_{1-6}$-hydroxyalkyl groups specifically illustrated by the examples herein below. Among the preferred $C_{1-6}$-hydroxyalkyl groups are hydroxymethyl, hydroxyethyl and 2-hydroxypropyl.

The term "3 to 10-membered cycloalkyl" refers to a monovalent saturated monocyclic or bicyclic hydrocarbon radical of 3 to 10 ring carbon atoms. Bicyclic means consisting of two saturated carbocycles having two carbon atoms in common, i.e. the bridge separating the two rings is either a single bond or a chain of preferably one or two carbon atoms. Examples for monocyclic 3 to 10-membered cycloalkyl are cyclopropyl, cyclobutanyl, cyclopentyl, cyclohexyl or cycloheptyl. Examples for bicyclic 3 to 10-membered cycloalkyl are bicyclo[2.2.1]heptanyl, and bicyclo[2.2.2]octanyl. Preferred 3 to 10-membered cycloalkyl is a monocyclic hydrocarbon radical of 3 to 6 ring carbon atoms, and preferred examples are cyclopropyl, cyclobutyl, cyclopentyl and cyclohexyl.

The term "3 to 6-membered cycloalkyl" refers to a monovalent saturated monocyclic hydrocarbon radical of 3 to 6 ring carbon atoms. Preferred examples are cyclopropyl, cyclobutyl, cyclopentyl and cyclohexyl.

The term "4 to 10-membered heterocycloalkyl" refers to a monovalent saturated 4 to 10-membered monocyclic or bicyclic ring system containing one, two or three ring heteroatoms selected from N, O and S, the remaining ring atoms being carbon atoms. In case of monocyclic 4 to 10-membered heterocycloalkyl, the ring is preferably 4- or 6-membered, in case of bicyclic 4 to 10-membered heterocycloalkyl, the bicyclic ring is preferably 7-, 8- or 9-membered. 4 to 10-membered heterocycloalkyl can be unsubstituted or substituted as described herein. Examples for substituents on 4 to 10-membered heterocycloalkyl are independently selected from $C_{1-6}$-alkyl, hydroxy, $C_{1-6}$-hydroxyalkyl, benzyl, oxo, —C(O)O—$C_{1-6}$-alkyl, 3 to 10-membered cycloalkyl, alkylene-O—$C_{1-6}$-alkyl, —C(O)-alkylene-O—$C_{1-6}$-alkyl, cyano-$C_{1-6}$-alkyl, alkylene-S(O)$_x$—$C_{1-6}$-alkyl, -alkylene-C(O)N($C_{1-6}$-alkyl)$_2$, halo, $C_{1-6}$-haloalkyl or $C_{1-6}$-alkoxy, wherein x is 0, 1, or 2. Among the preferred examples of 4- to 10-membered heterocycloalkyl are oxetanyl, tetrahydrofuranyl, tetrahydro-furanyl, tetrahydropyranyl, tetrahydropyranyl, piperidinyl, [1,3]dioxanyl, [1,4]dioxanyl and 7-oxa-bicyclo[2.2.1]heptyl.

The term "4 to 7-membered heterocycloalkyl" refers to a monovalent saturated monocycle or bicycle as defined above. Preferably, 4 to 7-membered heterocycloalkyl is a monovalent saturated monocyclic or bicyclic ring containing one or two ring heteroatoms selected from N, O, and S. Examples for 4 to 7-membered heterocycloalkyl moieties are tetrahydropyranyl, tetrahydrothiopyranyl, tetrahydrofuranyl, tetrahydrothiophenyl, pyrrolidinyl, imidazolidinyl, morpholinyl, thiomorpholinyl, piperidinyl, and piperazinyl. Preferred examples are oxetanyl, tetrahydrofuranyl, tetrahydropyranyl, piperidinyl, [1,3]dioxanyl, [1,4]dioxanyl and 7-oxa-bicyclo[2.2.1]heptyl. Most preferred is [1,4]dioxanyl. The 4 to 7-membered heterocycloalkyl moiety is optionally substituted as described herein.

The term "5 to 10-membered heteroaryl" denotes an aromatic monocyclic or bicyclic ring system of 5 to 10 ring atoms containing one, two, three or four heteroatoms selected from N, O, and S, the remaining ring atoms being C. Preferably, the monocyclic 5 to 10-membered heteroaryl ring is 5 or 6 membered and the bicyclic 5 to 10-membered heteroaryl ring is 9 or 10 membered. The one, two, three or four heteroatoms of the bicyclic 5 to 10-membered heteroaryl moiety are located in either one or both rings. Examples for 5 or 6-membered monocyclic heteroaryl include but are not limited to pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, or tetrazolyl. Examples for 9 or 10-membered bicyclic heteroaryl include but are not limited to indolyl, benzofuranyl, benzothiophenyl, benzimidazolyl, benzoxazolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phthalazinyl, or pteridinyl. Preferred examples for 5- or 6-membered monocyclic heteroaryl are thiophenyl and isoxazolyl. A preferred example for a 9-membered bicyclic heteroaryl is benzoisoxazolyl. 5 to 10-membered heteroaryl is optionally substituted as described herein.

Analogously to the 5 to 10-membered heteroaryl system, phenyl can be unsubstituted or substituted with one or more substituents selected from $C_{1-6}$-alkyl, 3 to 10-membered cycloalkyl, $C_{1-6}$-alkoxy, halo-$C_{1-6}$-alkoxy, $C_{1-6}$-haloalkyl, halo, OH, CN, or an anellated bridge being selected from —O—CH$_2$CH$_2$O—, —O—CHCH$_3$CH$_2$—, or —O—C(CH$_3$)$_2$CH$_2$—, however, wherein phenyl is not para-substituted with halo. Preferred substituents on phenyl are $C_{1-6}$-alkoxy, or an anellated bridge being selected from —O—CHCH$_3$CH$_2$—, or —O—C(CH$_3$)$_2$CH$_2$—.

The term "trans-configuration" denotes the orientation of functional groups within a molecule. Trans-configuration indicates an orientation, wherein a pair of substituents is attached on opposite sides of a stereoisomeric group, as for example

wherein $R^x$ and $R^y$ can be any kind of functional groups as described herein.

In detail, the present invention provides compounds of formula (I)

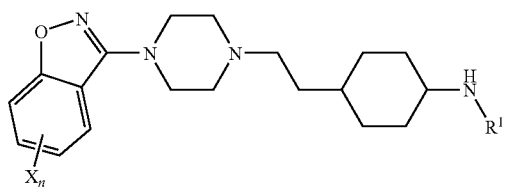

wherein:

X is independently halogen or $C_{1-6}$-alkyl;

n is 0, 1, or 2;

$R^1$ is —CO—$R^2$ or —SO$_2$—$C_{1-6}$-alkyl;

$R^2$ is $C_{1-6}$-alkyl, $C_{1-6}$-haloalkyl, $C_{1-6}$-hydroxyalkyl, $C_{1-6}$-alkoxy, 3 to 10 membered cycloalkyl, 4 to 10 membered heterocycloalkyl, or 5 to 10 membered heteroaryl, each of which is optionally substituted by one or more substituents selected from the group consisting of:

halo, hydroxy, $C_{1-6}$-alkyl, $C_{1-6}$-haloalkyl, $C_{1-6}$-hydroxyalkyl, $C_{1-6}$-alkoxy, $C_{1-6}$-alkoxy optionally substituted by one or more $R^a$, —S—$C_{1-6}$-alkyl, —SO$_2$—$C_{1-6}$-alkyl,

—CONH$_2$,

—CHO, 3 to 10 membered cycloalkyl optionally substituted by one or more $R^a$, 4 to 10 membered heterocycloalkyl optionally substituted by one or more $R^a$, and 5 to 10 membered heteroaryl optionally substituted by one or more $R^a$;

wherein $R^a$ is selected from the group consisting of:

halo, hydroxy, $C_{1-6}$-alkyl, $C_{1-6}$-hydroxyalkyl, $C_{1-6}$-haloalkyl, and $C_{1-6}$-alkoxy;

as well as pharmaceutically acceptable salts or esters thereof.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na-, K-, Ca- and trimethylammoniumsalt. The term "pharmaceutically acceptable salts" also refers to such salts. Preferred are the hydrochloride salts. Also solvates and hydrates of compounds of formula (I) and their salts form part of the present invention.

It will be appreciated, that the compounds of formula (I) in this invention can be derivatized at functional groups to provide derivatives which are capable of conversion back to the parent compound in vivo. Physiologically acceptable and metabolically labile derivatives, which are capable of producing the parent compounds of formula (I) in vivo are also within the scope of this invention.

The compounds of formula (I) can have one or more asymmetric Carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemate, by asymmetric synthesis or asymmetric chromatography (chromatography with a chiral adsorbens or eluant). The invention embraces all of these forms.

Further, it is to be understood that every embodiment relating to a specific residue X, $R^1$ or $R^2$ as disclosed herein can be combined with any other embodiment relating to another residue X, $R^1$ or $R^2$ as disclosed herein.

Particularly preferred compounds of formula (I) are those, wherein the piperazinyl-ethyl moiety and the N-amide moiety are attached to the cyclohexyl-ring in a trans-configuration.

In certain preferred embodiments of the compound of formula (I), X is fluoro or methyl.

In certain preferred embodiments of the compound of formula (I), n is 1 or 2.

In certain preferred embodiments of the compound of formula (I), $R^1$ is —CO—$R^2$.

In certain embodiments of the compound of formula (I), $R^2$ is $C_{1-6}$-alkyl, $C_{1-6}$-haloalkyl, $C_{1-6}$-hydroxyalkyl, $C_{1-6}$-alkoxy, 3 to 6-membered cycloalkyl, 4 to 7-membered heterocycloalkyl, or 5 membered heteroaryl, each of which is optionally substituted by one or more substituents selected from the group consisting of halo, hydroxy, $C_{1-6}$-alkyl, $C_{1-6}$-hydroxyalkyl, $C_{1-6}$-alkoxy, —S—$C_{1-6}$-alkyl, —$SO_2$—$C_{1-6}$-alkyl, —$CONH_2$, 3 to 6-membered cycloalkyl optionally substituted by one or more $R^a$, 4 to 7-membered heterocycloalkyl optionally substituted by one or more $R^a$, and 5 membered heteroaryl optionally substituted by one or more $R^a$, wherein $R^a$ is selected from the group consisting of hydroxy, $C_{1-6}$-alkyl, $C_{1-6}$-hydroxyalkyl, and $C_{1-6}$-alkoxy. Even more preferred compounds of the present invention are those, wherein $R^2$ is $C_{1-6}$-alkyl which is optionally substituted by one substituent selected from the group consisting of $C_{1-6}$-alkoxy, —$SO_2$—$C_{1-6}$-alkyl and 6 membered heterocycloalkyl. Most preferred are compounds of the present invention, wherein $R^2$ is methyl, methyl substituted by methanesulfonyl or [1,4] dioxin-2-yl or ethyl substituted by methoxy.

Preference is given to a compound of formula (I'):

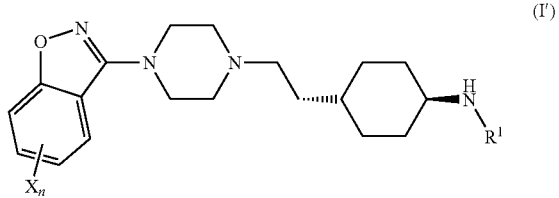

(I')

wherein X, $R^1$ and n are defined as given above.

Special preference is also given to a compound of formula (I') wherein $R^1$ is —$COR^2$; and wherein X, $R^2$ and n are defined as given above.

Another preferred embodiment of the instant invention provides a compound of formula (Ia):

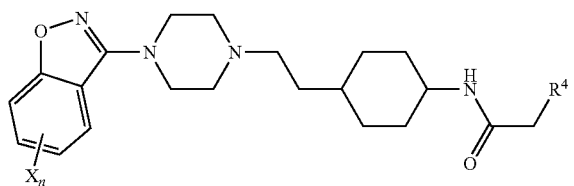

(Ia)

wherein:

X and n are defined as given above;

$R^4$ is hydrogen, hydroxyl, $C_{1-6}$-alkyl, $C_{1-6}$-hydroxyalkyl, $C_{1-6}$-alkoxy, 3 to 6-membered cycloalkyl optionally substituted by one or more $R^b$, or 4 to 7-membered heterocycloalkyl optionally substituted by one or more $R^b$, wherein $R^b$ is selected from the group consisting of:

hydroxy, $C_{1-6}$-alkyl, $C_{1-6}$-hydroxyalkyl, and $C_{1-6}$-alkoxy.

Also preferred is a compound of formula (Ia'):

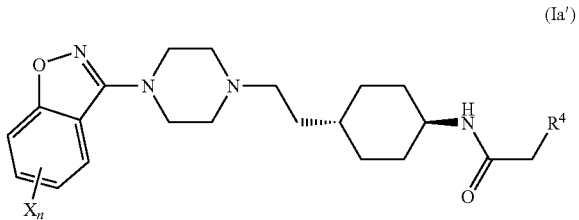

(Ia')

wherein X, $R^4$ and n are defined as given above.

Special preference is given to a compound of formula (Ia') wherein X and n are defined as given above; and $R^4$ is $C_{1-6}$-alkoxy or $C_{1-6}$-alkoxy-$C_{1-6}$-alkyl.

Especially preferred compounds of formula (Ia') include the following compounds:

N-trans-{4-[2-(4-benzo[d]isoxazol-3-yl)-piperazin-1-yl)-ethyl]-cyclohexyl}-3-methoxy-propionamide;

N-trans-(4-{2-[4-(5-Fluoro-benzo[d]isoxazol-3-yl)-piperazin-1-yl]-ethyl}-cyclohexyl)-3-methoxy-propionamide;

N-trans-(4-{2-[4-(5-Fluoro-benzo[d]isoxazol-3-yl)-piperazin-1-yl]-ethyl}-cyclohexyl)-2-methoxy-acetamide;

2-Ethoxy-N-trans-(4-{2-[4-(5-fluoro-benzo[d]isoxazol-3-yl)-piperazin-1-yl]-ethyl}-cyclohexyl)-acetamide;

N-trans-(4-{2-[4-(5-Fluoro-benzo[d]isoxazol-3-yl)-piperazin-1-yl]-ethyl}-cyclohexyl)-3,3-dimethoxy-propionamide;

N-trans-(4-{2-[4-(5-Fluoro-benzo[d]isoxazol-3-yl)-piperazin-1-yl]-ethyl}-cyclohexyl)-4,4-dimethoxy-butyramide;

N-trans-(4-{2-[4-(6-Chloro-benzo[d]isoxazol-3-yl)-piperazin-1-yl]-ethyl}-cyclohexyl)-3-methoxy-propionamide;

N-trans-(4-{2-[4-(6-Chloro-benzo[d]isoxazol-3-yl)-piperazin-1-yl]-ethyl}-cyclohexyl)-3-methoxy-butyramide;

N-trans-(4-{2-[4-(6-Chloro-benzo[d]isoxazol-3-yl)-piperazin-1-yl]-ethyl}-cyclohexyl)-3,3-dimethoxy-propionamide;

N-trans-(4-{2-[4-(5,6-Difluoro-benzo[d]isoxazol-3-yl)-piperazin-1-yl]-ethyl}-cyclohexyl)-3-methoxy-propionamide;

N-trans-(4-{2-[4-(5,6-Difluoro-benzo[d]isoxazol-3-yl)-piperazin-1-yl]-ethyl}-cyclohexyl)-2-methoxy-acetamide;

N-trans-(4-{2-[4-(6-Chloro-5-fluoro-benzo[d]isoxazol-3-yl)-piperazin-1-yl]-ethyl}-cyclohexyl)-3-methoxy-propionamide;

N-trans-(4-{2-[4-(5-Chloro-6-fluoro-benzo[d]isoxazol-3-yl)-piperazin-1-yl]-ethyl}-cyclohexyl)-3-methoxy-propionamide;

N-trans-(4-{2-[4-(5-Chloro-6-fluoro-benzo[d]isoxazol-3-yl)-piperazin-1-yl]-ethyl}-cyclohexyl)-3,3-dimethoxy-propionamide;

N-trans-(4-{2-[4-(5,6-Dichloro-benzo[d]isoxazol-3-yl)-piperazin-1-yl]-ethyl}-cyclohexyl)-3-methoxy-propionamide;

3-Methoxy-N-trans-(4-{2-[4-(6-methyl-benzo[d]isoxazol-3-yl)-piperazin-1-yl]ethyl}-cyclohexyl)-propionamide;

3,3-Dimethoxy-N-trans-(4-{2-[4-(6-methyl-benzo[d]isoxazol-3-yl)-piperazin-1-yl]-ethyl}-cyclohexyl)-propionamide;

3-Methoxy-N-trans-(4-{2-[4-(5-methyl-benzo[d]isoxazol-3-yl)-piperazin-1-yl]-ethyl}-cyclohexyl)-propionamide;

N-trans-(4-{2-[4-(6-Fluoro-5-methyl-benzo[d]isoxazol-3-yl)-piperazin-1-yl]-ethyl}-cyclohexyl)-2-methoxy-acetamide;

N-trans-(4-{2-[4-(6-Fluoro-5-methyl-benzo[d]isoxazol-3-yl)-piperazin-1-yl]-ethyl}-cyclohexyl)-3-methoxy-propionamide; and 2-Ethoxy-N-trans-(4-{2-[4-(6-fluoro-5-methyl-benzo[d]isoxazol-3-yl)-piperazin-1-yl]-ethyl}-cyclohexyl)-acetamide.

Also preferred is a compound of formula (Ia') wherein:

X and n are defined as given above;

$R^4$ is 3 to 6-membered cycloalkyl optionally substituted by one or more $R^b$, or 4 to 7-membered heterocycloalkyl optionally substituted by one or more $R^b$;

wherein $R^b$ is selected from the group consisting of:

hydroxy, $C_{1-6}$-alkyl, $C_{1-6}$-hydroxyalkyl, and $C_{1-6}$-alkoxy.

Further preferred compounds of formula (Ia') include the following compounds:

N-trans-{4-[2-(4-Benzo[d]isoxazol-3-yl)-piperazin-1-yl)-ethyl]-cyclohexyl}-2-trans-(3-methoxy-cyclopentyl)-acetamide;

N-trans-(4-{2-[4-(5-Fluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide;

2-[1,4]Dioxan-2-yl-N-trans-(4-{2-[4-(5-fluoro-benzo[d]isoxazol-3-yl)-piperazin-1-yl]-ethyl}-cyclohexyl)-acetamide;

Rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;

N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide;

N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide;

N-trans-(4-{2-[4-(5-Fluoro-benzo[d]isoxazol-3-yl)-piperazin-1-yl]-ethyl}-cyclohexyl)-2-(3-methyl-oxetan-3-yl)-acetamide;

N-trans-(4-{2-[4-(5-Fluoro-benzo[d]isoxazol-3-yl)-piperazin-1-yl]-ethyl}-cyclohexyl)-2-((S)-2,2,4-trimethyl-tetrahydro-pyran-4-yl)-acetamide;

N-trans-(4-{2-[4-(5-Fluoro-benzo[d]isoxazol-3-yl)-piperazin-1-yl]-ethyl}-cyclohexyl)-2-((R)-2,2,4-trimethyl-tetrahydro-pyran-4-yl)-acetamide;

2-[1,3]Dioxan-2-yl-N-trans-(4-{2-[4-(5-fluoro-benzo[d]isoxazol-3-yl)-piperazin-1-yl]-ethyl}-cyclohexyl)-acetamide;

N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide;

N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide;

N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide;

N-trans-(4-{2-[4-(6-Chloro-benzo[d]isoxazol-3-yl)-piperazin-1-yl]-ethyl}-cyclohexyl)-2-(tetrahydro-pyran-2-yl)-acetamide;

N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide;

N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide;

N-trans-(4-{2-[4-(6-Chloro-benzo[d]isoxazol-3-yl)-piperazin-1-yl]-ethyl}-cyclohexyl)-2-(tetrahydro-pyran-4-yl)-acetamide;

N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide;

N-trans-(4-{2-[4-(6-Chloro-benzo[d]isoxazol-3-yl)-piperazin-1-yl]-ethyl}-cyclohexyl)-2-oxetan-3-yl-acetamide;

N-trans-(4-{2-[4-(6-Chloro-benzo[d]isoxazol-3-yl)-piperazin-1-yl]-ethyl}-cyclohexyl)-2-trans-(3-methoxymethyl-cyclobutyl)-acetamide;

N-trans-(4-{2-[4-(6-Chloro-benzo[d]isoxazol-3-yl)-piperazin-1-yl]-ethyl}-cyclohexyl)-2-(R)-tetrahydro-pyran-2-yl-acetamide;

N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide;

N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide;

N-trans-(4-{2-[4-(6-Chloro-benzo[d]isoxazol-3-yl)-piperazin-1-yl]-ethyl}-cyclohexyl)-2-cyclopropyl-acetamide;

N-trans-(4-{2-[4-(6-Difluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide;

N-trans-(4-{2-[4-(5,6-Difluoro-benzo[d]isoxazol-3-yl)-piperazin-1-yl]ethyl}-cyclohexyl)-2-(tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide;

N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide;

N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5-Chloro-6-fluoro-benzo[d]isoxazol-3-yl)-piperazin-1-yl]-ethyl}-cyclohexyl)-2-cyclopropyl-acetamide;

N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide;

N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide;

N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Dichloro-benzo[d]isoxazol-3-yl)-piperazin-1-yl]-ethyl}-cyclohexyl)-2-(tetrahydro-pyran-4-yl)-acetamide;

2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide;

2-[1,3]Dioxan-2-yl-N-trans-(4-{2-[4-(6-methyl-benzo[d]isoxazol-3-yl)-piperazin-1-yl]-ethyl}-cyclohexyl)-acetamide;

2-[1,4]Dioxan-2-yl-N-trans-(4-{2-[4-(6-methyl-benzo[d]isoxazol-3-yl)-piperazin-1-yl]-ethyl}-cyclohexyl)-acetamide;

2-Cyclopropyl-N-trans-(4-{2-[4-(6-fluoro-5-methyl-benzo[d]isoxazol-3-yl)-piperazin-1-yl]-ethyl}-cyclohexyl)-acetamide;

2-[1,3]-Dioxan-2-yl-N-trans-(4-{2-[4-(6-fluoro-5-methyl-benzo[d]isoxazol-3-yl)-piperazin-1-yl]-ethyl}-cyclohexyl)-acetamide; and N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide.

Another preferred embodiment of the instant invention provides a compound of formula (Ib):

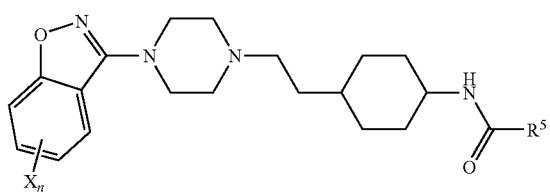

(Ib)

wherein:

X and n are defined as given above; and $R^5$ is 4 to 7-membered heterocycloalkyl; or 3 to 6-membered cycloalkyl optionally substituted by one or more halogen, hydroxyl or $C_{1-6}$-alkoxy.

Also preferred is a compound of formula (Ib'):

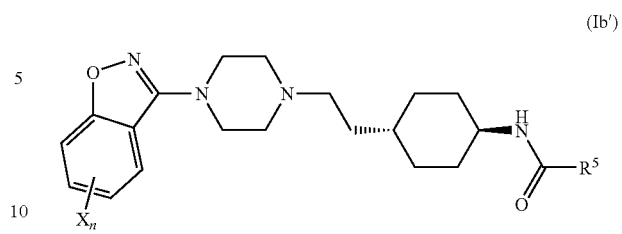

(Ib')

wherein X, $R^5$ and n are defined as given above.

Especially preferred compounds of formula (Ib') include the following compounds:

4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;

3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;

Tetrahydro-pyran-4-carboxylic acid N-trans-(4-{2-[4-(6-chloro-benzo[d]isoxazol-3-yl)-piperazin-1-yl]-ethyl}-cyclohexyl)-amide;

Tetrahydro-furan-3-carboxylic acid N-trans-(4-{2-[4-(6-chloro-benzo[d]isoxazol-3-yl)-piperazin-1-yl]-ethyl}-cyclohexyl)-amide;

1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide;

(S)-Tetrahydro-furan-3-carboxylic acid (4-{2-[4-(6-chloro-benzo[d]isoxazol-3-yl)-piperazin-1-yl]-ethyl}-cyclohexyl)-amide;

4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide;

4-Methoxy-cyclohexanecarboxylic acid N-trans (4-{2-[4-(6-difluoro-benzo[d]isoxazol-3-yl)-piperazin-1-yl]-ethyl}-cyclohexyl)-amide;

Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide;

1-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide;

Cyclobutanecarboxylic acid N-trans-(4-{2-[4-(5-chloro-6-fluoro-benzo[d]isoxazol-3-yl)-piperazin-1-yl]-ethyl}-cyclohexyl)-amide;

Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide;

Particularly preferred compounds of formula (I) include the following compounds:

N-trans-{4-[2-(4-benzo[d]isoxazol-3-yl)-piperazin-1-yl)-ethyl]-cyclohexyl}-3-methoxy-propionamide;

N-trans-{4-[2-(4-benzo[d]isoxazol-3-yl)-piperazin-1-yl)-ethyl]-cyclohexyl}-acetamide;

N-trans-{4-[2-(4-Benzo[d]isoxazol-3-yl)-piperazin-1-yl)-ethyl]-cyclohexyl}-2-trans-(3-methoxy-cyclopentyl)-acetamide;

N-trans-{4-[2-(4-Benzo[d]isoxazol-3-yl)-piperazin-1-yl)-ethyl]-cyclohexyl}-2-hydroxy-acetamide;

N-trans-(4-{4-[2-(5-Fluoro-benzo[d]isoxazol-3-yl)-piperazin-1-yl]-ethyl}-cyclohexyl)-3-methoxy-propionamide;

N-trans-(4-{4-[2-(5-Fluoro-benzo[d]isoxazol-3-yl)-piperazin-1-yl]-ethyl}-cyclohexyl)-2-trans-(4-methoxy-cyclohexyl)-acetamide;
Tetrahydro-pyran-4-carboxylic acid-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide;
N-trans-(4-{2-[4-(5-Fluoro-benzo[d]isoxazol-3-yl)-piperazin-1-yl]-ethyl}-cyclohexyl)-2-methoxy-acetamide;
N-trans-(4-{4-[2-(5-Fluoro-benzo[d]isoxazol-3-yl)-piperazin-1-yl]-ethyl}-cyclohexyl)-2-(4-isopropoxy-cyclohexyl)-acetamide;
N-trans-(4-{4-[2-(5-Fluoro-benzo[d]isoxazol-3-yl)-piperazin-1-yl]-ethyl}-cyclohexyl)-3-hydroxy-3-methyl-butyramide;
2-Ethoxy-N-trans-(4-{2-[4-(5-fluoro-benzo[d]isoxazol-3-yl)-piperazin-1-yl]-ethyl}-cyclohexyl)-acetamide;
4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-methanesulfonamide;
2-[1,4]-Dioxan-2-yl-N-trans-(4-{2-[4-(5-fluoro-benzo[d]isoxazol-3-yl)-piperazin-1-yl]-ethyl}-cyclohexyl)-acetamide;
3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-malonamide;
Rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;
N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide;
N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide;
N-trans-(4-{2-[4-(5-Fluoro-benzo[d]isoxazol-3-yl)-piperazin-1-yl]-ethyl}-cyclohexyl)-2-(3-methyl-oxetan-3-yl)-acetamide;
2-((S)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;
2-((R)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;
2-[1,3]Dioxan-2-yl-N-trans-(4-{2-[4-(5-fluoro-benzo[d]isoxazol-3-yl)-piperazin-1-yl]-ethyl}-cyclohexyl)-acetamide;
N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide;
N-trans-(4-{2-[4-(5-Fluoro-benzo[d]isoxazol-3-yl)-piperazin-1-yl]-ethyl}-cyclohexyl)-3,3-dimethoxy-propionamide;
N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide;
N-trans-(4-{2-[4-(5-Fluoro-benzo[d]isoxazol-3-yl)-piperazin-1-yl]-ethyl}-cyclohexyl)-4,4-dimethoxy-butyramide;
N-trans-(4-{2-[4-(6-Chloro-benzo[d]isoxazol-3-yl)-piperazin-1-yl]-ethyl}-cyclohexyl)-3-methoxy-propionamide;
N-trans-(4-{2-[4-(6-Chloro-benzo[d]isoxazol-3-yl)-piperazin-1-yl]-ethyl}-cyclohexyl)-acetamide;
N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide;
Tetrahydro-pyran-4-carboxylic acid N-trans-(4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-rac-3,3,3-trifluoro-2-hydroxy-propionamide;
Tetrahydro-furan-3-carboxylic acid N-trans-(4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-2-(tetrahydro-pyran-2-yl)-acetamide;
N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide;
N-trans-(4-{2-[4-(6-Chloro-benzo[d]isoxazol-3-yl)-piperazin-1-yl]-ethyl}-cyclohexyl)-3-methoxy-butyramide;
1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide;
N-trans-(4-{2-[4-(6-Chloro-benzo[d]isoxazol-3-yl)-piperazin-1-yl]-ethyl}-cyclohexyl)-2-(tetrahydro-pyran-4-yl)-acetamide;
N-trans-(4-{2-[4-(6-Chloro-benzo[d]isoxazol-3-yl)-piperazin-1-yl]-ethyl}-cyclohexyl)-propionamide;
N-trans-(4-{2-[4-(6-Chloro-benzo[d]isoxazol-3-yl)-piperazin-1-yl]-ethyl}-cyclohexyl)-2-hydroxy-acetamide;
N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide;
N-trans-(4-{2-[4-(6-Chloro-benzo[d]isoxazol-3-yl)-piperazin-1-yl]-ethyl}-cyclohexyl)-3-hydroxy-3-methyl-butyramide;
(S)—N-(4-{2-[4-(6-Chloro-benzo[d]isoxazol-3-yl)-piperazin-1-yl]-ethyl}-cyclohexyl)-3-hydroxy-butyramide;
(S)-Tetrahydro-furan-3-carboxylic acid (4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-2-oxetan-3-yl-acetamide;
N-trans-(4-{2-[4-(6-Chloro-benzo[d]isoxazol-3-yl)-piperazin-1-yl]-ethyl}-cyclohexyl)-2-trans-(3-methoxymethyl-cyclobutyl)-acetamide;
N-trans-(4-{2-[4-(6-Chloro-benzo[d]isoxazol-3-yl)-piperazin-1-yl]ethyl}-cyclohexyl)-2-(R)-tetrahydro-pyran-2-yl-acetamide;
N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide;
N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide;
N-trans-(4-{2-[4-(6-Chloro-benzo[d]isoxazol-3-yl)-piperazin-1-yl]-ethyl}-cyclohexyl)-2-cyclopropyl-acetamide;
N-trans-(4-{2-[4-(6-Chloro-benzo[d]isoxazol-3-yl)-piperazin-1-yl]-ethyl}-cyclohexyl)-3,3,3-trifluoro-propionamide;

4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide;

N-trans-(4-{2-[4-(6-Chloro-benzo[d]isoxazol-3-yl)-piperazin-1-yl]-ethyl}-cyclohexyl)-3,3-dimethoxy-propionamide;

N-trans-(4-{2-[4-(5,6-Difluoro-benzo[d]isoxazol-3-yl)-piperazin-1-yl]-ethyl}-cyclohexyl)-acetamide;

N-trans-(4-{2-[4-(5,6-Difluoro-benzo[d]isoxazol-3-yl)-piperazin-1-yl]-ethyl}-cyclohexyl)-3-methoxy-propionamide;

N-trans-(4-{2-[4-(5,6-Difluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Difluoro-benzo[d]isoxazol-3-yl)-piperazin-1-yl]-ethyl}-cyclohexyl)-propionamide;

N-trans-(4-{2-[4-(5,6-Difluoro-benzo[d]isoxazol-3-yl)-piperazin-1-yl]-ethyl}-cyclohexyl)-2-methoxy-acetamide;

N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-3-hydroxy-3-methyl-butyramide;

N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide;

4-Methoxy-cyclohexanecarboxylic acid N-trans-(4-{2-[4-(5,6-difluoro-benzo[d]isoxazol-3-yl)-piperazin-1-yl]-ethyl}-cyclohexyl)-amide;

Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide;

Ethanesulfonic acid N-trans-(4-{2-[4-(5,6-difluoro-benzo[d]isoxazol-3-yl)-piperazin-1-yl]-ethyl}-cyclohexyl)-amide;

N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide;

N-trans-(4-{2-[4-(6-Chloro-5-fluoro-benzo[d]isoxazol-3-yl)-piperazin-1-yl]-ethyl}-cyclohexyl)-propionamide;

N-trans-(4-{2-[4-(6-Chloro-5-fluoro-benzo[d]isoxazol-3-yl)-piperazin-1-yl]-ethyl}-cyclohexyl)-3-methoxy-propionamide;

N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5-Chloro-6-fluoro-benzo[d]isoxazol-3-yl)-piperazin-1-yl]-ethyl}-cyclohexyl)-acetamide;

N-trans-(4-{2-[4-(5-Chloro-6-fluoro-benzo[d]isoxazol-3-yl)-piperazin-1-yl]-ethyl}-cyclohexyl)-3-methoxy-propionamide;

N-trans-(4-{2-[4-(5-Chloro-6-fluoro-benzo[d]isoxazol-3-yl)-piperazin-1-yl]-ethyl}-cyclohexyl)-2-cyclopropyl-acetamide;

N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-3,3-dimethoxy-propionamide;

N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide;

N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide;

N-trans-(4-{2-[4-(5-Chloro-6-fluoro-benzo[d]isoxazol-3-yl)-piperazin-1-yl]-ethyl}-cyclohexyl)-3-methylsulfanyl-propionamide;

N-trans-(4-{2-[4-(5-Chloro-6-fluoro-benzo[d]isoxazol-3-yl)-piperazin-1-yl]-ethyl}-cyclohexyl)-2-(3-methyl-isoxazol-5-yl)-acetamide;

3-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide;

5-Chloro-thiophene-2-carboxylic acid N-trans-(4-{2-[4-(5-chloro-6-fluoro-benzo[d]isoxazol-3-yl)-piperazin-1-yl]-ethyl}-cyclohexyl)-amide;

5-Methoxy-thiophene-2-carboxylic acid N-trans-(4-{2-[4-(5-chloro-6-fluoro-benzo[d]isoxazol-3-yl)-piperazin-1-yl]-ethyl}-cyclohexyl)-amide;

N-trans-(4-{2-[4-(5-Chloro-6-fluoro-benzo[d]isoxazol-3-yl)-piperazin-1-yl]-ethyl}-cyclohexyl)-propionamide;

N-trans-(4-{2-[4-(5-Chloro-6-fluoro-benzo[d]isoxazol-3-yl)-piperazin-1-yl]-ethyl}-cyclohexyl)-2-hydroxy-acetamide;

N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5-Chloro-6-fluoro-benzo[d]isoxazol-3-yl)-piperazin-1-yl]-ethyl}-cyclohexyl)-2-methanesulfonyl-acetamide;

N-trans-(4-{2-[4-(5-Chloro-6-fluoro-benzo[d]isoxazol-3-yl)-piperazin-1-yl]-ethyl}-cyclohexyl)-3-methanesulfonyl-propionamide;

N-trans-(4-{2-[4-(5-Chloro-6-fluoro-benzo[d]isoxazol-3-yl)-piperazin-1-yl]-ethyl}-cyclohexyl)-carbamic acid methyl ester;

Cyclobutanecarboxylic acid N-trans-(4-{2-[4-(5-chloro-6-fluoro-benzo[d]isoxazol-3-yl)-piperazin-1-yl]-ethyl}-cyclohexyl)-amide;

N-trans-(4-{2-[4-(5-Chloro-6-fluoro-benzo[d]isoxazol-3-yl)-piperazin-1-yl]-ethyl}-cyclohexyl)-3,3,3-trifluoro-propionamide;

N-trans-(4-{2-[4-(5,6-Dichloro-benzo[d]isoxazol-3-yl)-piperazin-1-yl]-ethyl}-cyclohexyl)-3-methoxy-propionamide;

Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide;

N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Dichloro-benzo[d]isoxazol-3-yl)-piperazin-1-yl]-ethyl}-cyclohexyl)-2-(tetrahydro-pyran-4-yl)-acetamide;

3-Methoxy-N-trans-(4-{2-[4-(6-methyl-benzo[d]isoxazol-3-yl)-piperazin-1-yl]-ethyl}-cyclohexyl)-propionamide;

N-trans-(4-{2-[4-(6-Methyl-benzo[d]isoxazol-3-yl)-piperazin-1-yl]-ethyl}-cyclohexyl)-propionamide;

2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide;

2-[1,3]Dioxan-2-yl-N-trans-(4-{2-[4-(6-methyl-benzo[d]isoxazol-3-yl)-piperazin-1-yl]-ethyl}-cyclohexyl)-acetamide;

2-[1,4]Dioxan-2-yl-N-trans-(4-{2-[4-(6-methyl-benzo[d]isoxazol-3-yl)-piperazin-1-yl]-ethyl}-cyclohexyl)-acetamide;

3,3-Dimethoxy-N-trans-(4-{2-[4-(6-methyl-benzo[d]isoxazol-3-yl)-piperazin-1-yl]-ethyl}-cyclohexyl)-propionamide;

3-Methoxy-N-trans-(4-{2-[4-(5-methyl-benzo[d]isoxazol-3-yl)-piperazin-1-yl]-ethyl}-cyclohexyl)-propionamide;

2-Methanesulfonyl-N-trans-(4-{2-[4-(6-methyl-benzo[d]isoxazol-3-yl)-piperazin-1-yl]-ethyl}-cyclohexyl)-acetamide;

N-trans-(4-{2-[4-(6-Fluoro-5-methyl-benzo[d]isoxazol-3-yl)-piperazin-1-yl]-ethyl}-cyclohexyl)-acetamide;

N-trans-(4-{2-[4-(6-Fluoro-5-methyl-benzo[d]isoxazol-3-yl)-piperazin-1-yl]-ethyl}-cyclohexyl)-2-methoxy-acetamide;

N-trans-(4-{2-[4-(6-Fluoro-5-methyl-benzo[d]isoxazol-3-yl)-piperazin-1-yl]-ethyl}-cyclohexyl)-3-methoxy-propionamide;

2-Cyclopropyl-N-trans-(4-{2-[4-(6-fluoro-5-methyl-benzo[d]isoxazol-3-yl)-piperazin-1-yl]-ethyl}-cyclohexyl)-acetamide;

2-Ethoxy-N-trans-(4-{2-[4-(6-fluoro-5-methyl-benzo[d]isoxazol-3-yl)-piperazin-1-yl]-ethyl}-cyclohexyl)-acetamide;

2-[1,3]Dioxan-2-yl-N-trans-(4-{2-[4-(6-fluoro-5-methyl-benzo[d]isoxazol-3-yl)-piperazin-1-yl]-ethyl}-cyclohexyl)-acetamide;

N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide;

2-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;

2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;

2-(S)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;

(S)-4,4,4-Trifluoro-N-trans-(4-{2-[4-(6-fluoro-5-methyl-benzo[d]isoxazol-3-yl)-piperazin-1-yl]-ethyl}-cyclohexyl)-3-hydroxy-butyramide;

N-trans-(4-{2-[4-(6-Fluoro-5-methyl-benzo[d]isoxazol-3-yl)-piperazin-1-yl]-ethyl}-cyclohexyl)-2-(tetrahydro-pyran-2-yl)-acetamide;

N-trans-(4-{2-[4-(6-Fluoro-5-methyl-benzo[d]isoxazol-3-yl)-piperazin-1-yl]-ethyl}-cyclohexyl)-2-(tetrahydro-furan-2-yl)-acetamide; and N-trans-(4-{2-[4-(6-Fluoro-5-methyl-benzo[d]isoxazol-3-yl)-piperazin-1-yl]-ethyl}-cyclohexyl)-2-methoxy-propionamide.

Even more preferred compounds of formula (I) of present invention are those selected from the group consisting of:

2-Methanesulfonyl-N-trans-(4-{2-[4-(6-methyl-benzo[d]isoxazol-3-yl)-piperazin-1-yl]-ethyl}-cyclohexyl)-acetamide;

N-trans-(4-{2-[4-(6-Fluoro-5-methyl-benzo[d]isoxazol-3-yl)-piperazin-1-yl]-ethyl}-cyclohexyl)-acetamide;

N-trans-(4-{2-[4-(6-Fluoro-5-methyl-benzo[d]isoxazol-3-yl)-piperazin-1-yl]-ethyl}-cyclohexyl)-3-methoxy-propionamide; and 2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide.

A further aspect of the present invention provides the process for the manufacture of compounds of formula (I) as defined above.

The preparation of compounds of formula (I) of the present invention can be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the description or in the examples, or by methods known in the art.

A preferred embodiment of the process for preparing a compound of formula (I) comprises one of the following steps:

a) reductive amination of an aldehyde of formula (I-1) with a 3-piperazine-1-yl-1,2-benzisoxazole of formula (I-2) in the presence of a reducing agent, and

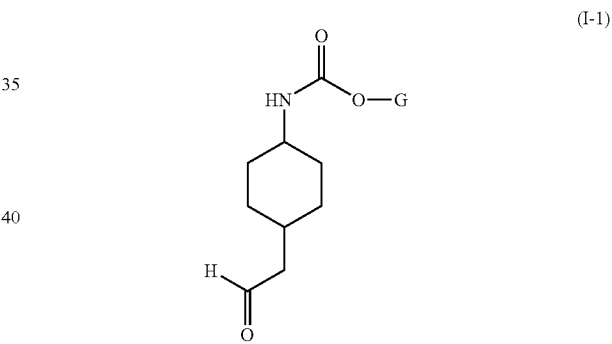

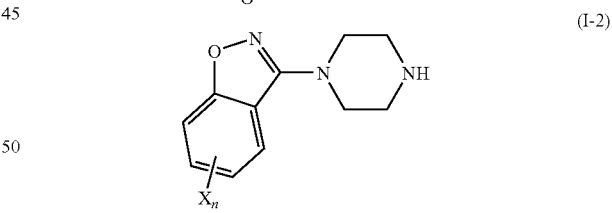

removing the protecting group G under acidic conditions to yield amine intermediate of formula (I-3),

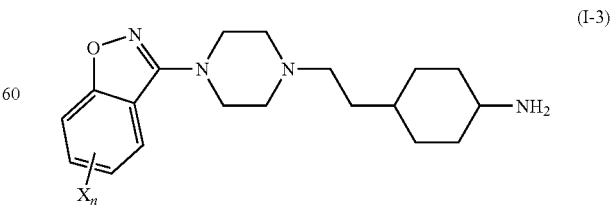

b) and coupling of amine intermediate of formula (I-3) with a carboxylic acid $R^2$—COOH, acid chloride $R^2$—COCl, or sulfonyl chloride R³—SO₂Cl to yield compounds of formula (I), wherein X, n and R² are as defined above and R³ is $C_{1-6}$-alkyl.

yl-1,2-benzisoxazole (4) either commercially available or accessible by methods described in references, by methods described in this patent or by methods known in the art in the

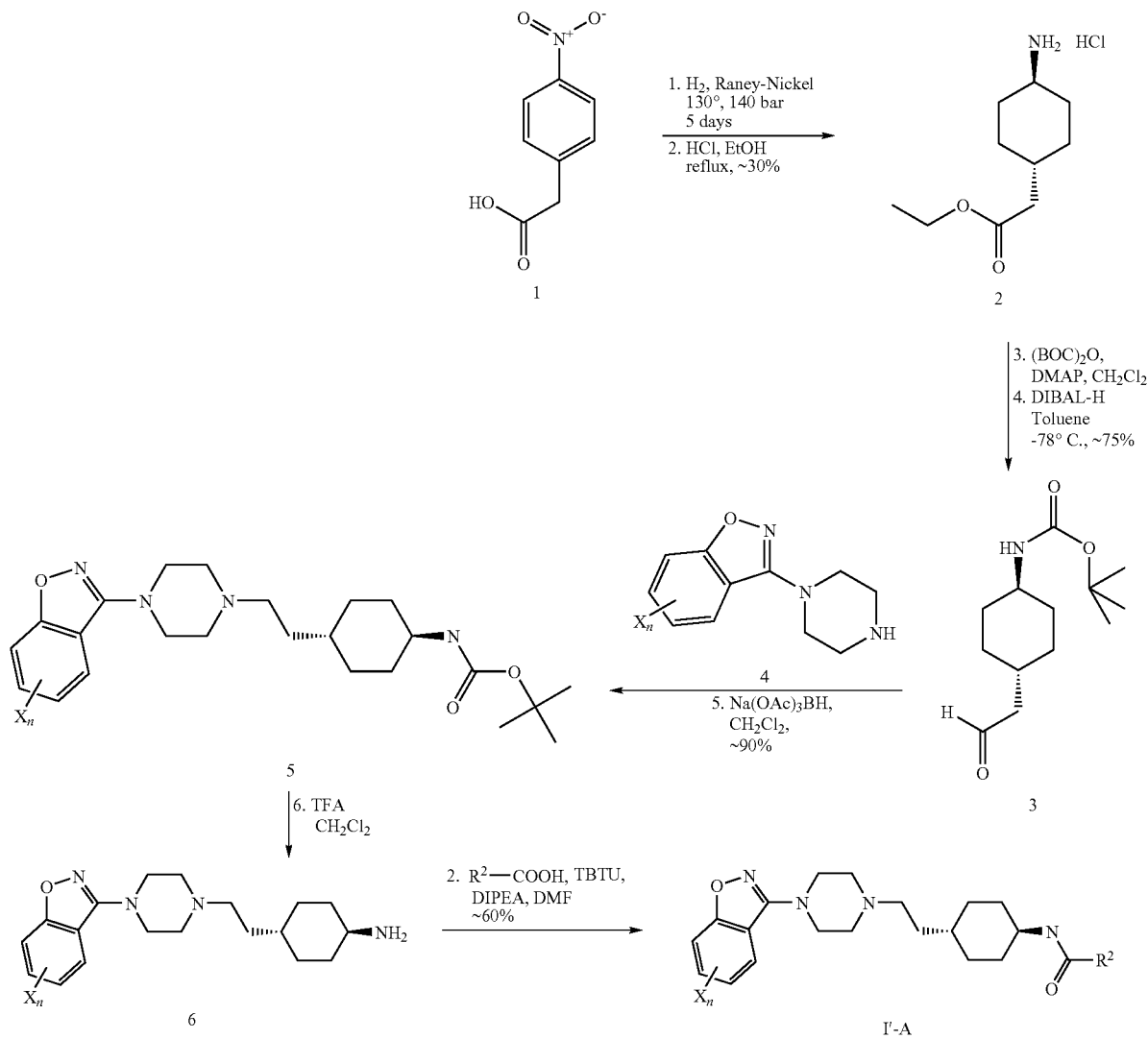

N-{4-[2-(4-Benzo[d]isoxazol-3-yl)-piperazin-1-yl)-ethyl]-cyclohexyl}-amide derivates of formula (I'-A), wherein X, n and R² are as defined above, can be prepared as depicted in scheme 1 starting from 4-nitro-phenylacetic acid (1) that was hydrogenated using Raney nickel as catalyst. The hydrogenation with nickel leads preferentially to the desired trans-isomer (according to Journal of Medicinal Chemistry, 1998, 41, 760-771). Preparing the ethyl ester according to methods known to those skilled in the art and described in the mentioned literature (e.g. by treatment with ethanol on the presence of an acid such as HCl) and crystallizing the HCl salt leads to the resolution of the cis/trans mixture yielding the pure trans amino ester chloride (2). Introduction of a protecting group with a reagent such as tert-butyl dicarbonate (BOC) on the presence of a base like triethylamine and a catalyst like dimethylaminopyridine (DMAP) and reduction with diisobutylaluminium hydride (DIBAL-H) in an appropriate solvent such as, e.g. toluene at −78° C. gives the aldehyde (3) which can be used without purification on the next step. Reductive amination of aldehyde (3) with a substituted 3-piperazin-1-yl-1,2-benzisoxazole (4) either commercially available or accessible by methods described in references, by methods described in this patent or by methods known in the art in the presence of a solvent like dichloromethane and a reducing agent such as sodium triacetoxy borohydride yields intermediate (5). Removal of the BOC protective group under acidic conditions such as trifluoroacetic acid in dichloromethane or hydrochloric acid in dioxane yields the trans-amino cyclohexyl ethyl intermediate (6) (usually the HCl salt). The coupling of the amine intermediate (6) with carboxylic acids (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. dimethylformamide (DMF) or dioxane in the presence of a base (e.g. triethylamine or diisopropylethylamine (DIPEA)) to yield compounds of formula (I'-A), wherein X, n and R² are as defined above. In other cases an acid chloride can also be used in the presence of a base (e.g. triethylamine or diisopropylethylamine) in a solvent like dichloromethane.

oxime derivative. Deprotonation of the oxime with a base such as KOH in water and a solvent like dioxane and intramolecular cyclization leads to the benzo[d]isoxazole derivative.

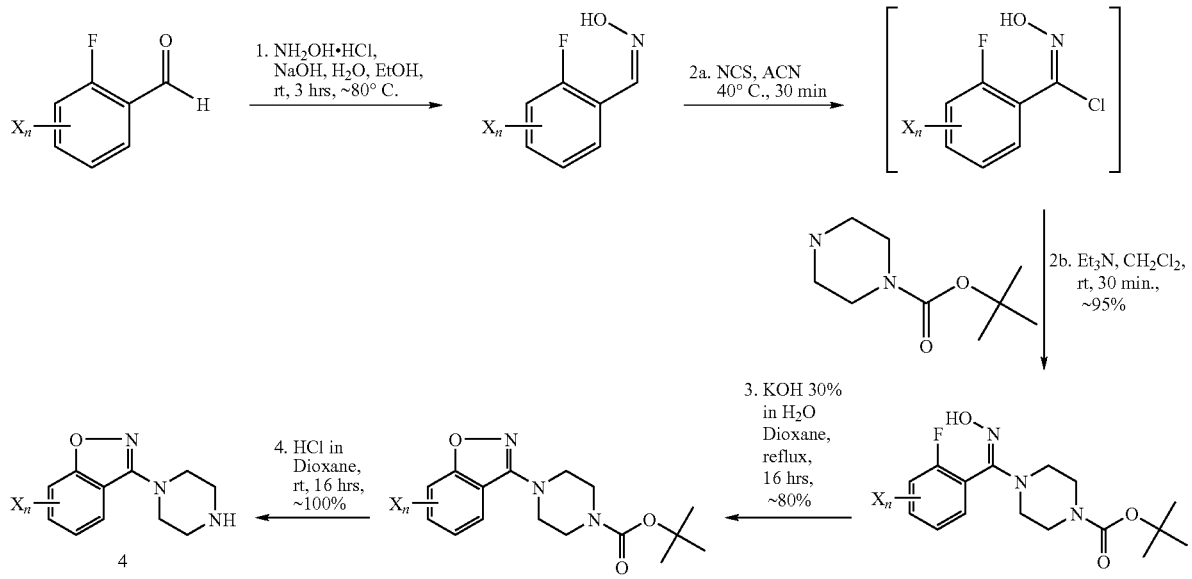

A 3-piperazin-1-yl-1,2-benzisoxazole of formula (4), wherein X and n are as defined above, can be obtained starting from an appropriately substituted benzaldehyde containing a leaving group such as for example F in ortho position. The benzaldehyde can be converted to the corresponding oxime with a reagent such as NH$_2$OH.HCl in the presence of a base such as NaOH in a solvent mixture like water and EtOH. Chlorination of the oxime with a reagent such as N-chlorosuccinimide (NCS) in a solvent like acetonitrile (ACN) and reaction with piperazine-1-carboxylic acid tert-butyl ester yields the corresponding phenyl-piperazin-1-yl-methanone Removal of the BOC protective group under acidic conditions such as hydrochloric acid in dioxane yields the 3-piperazin-1-yl-1,2-benzisoxazole of formula (4), wherein X and n are as defined above.

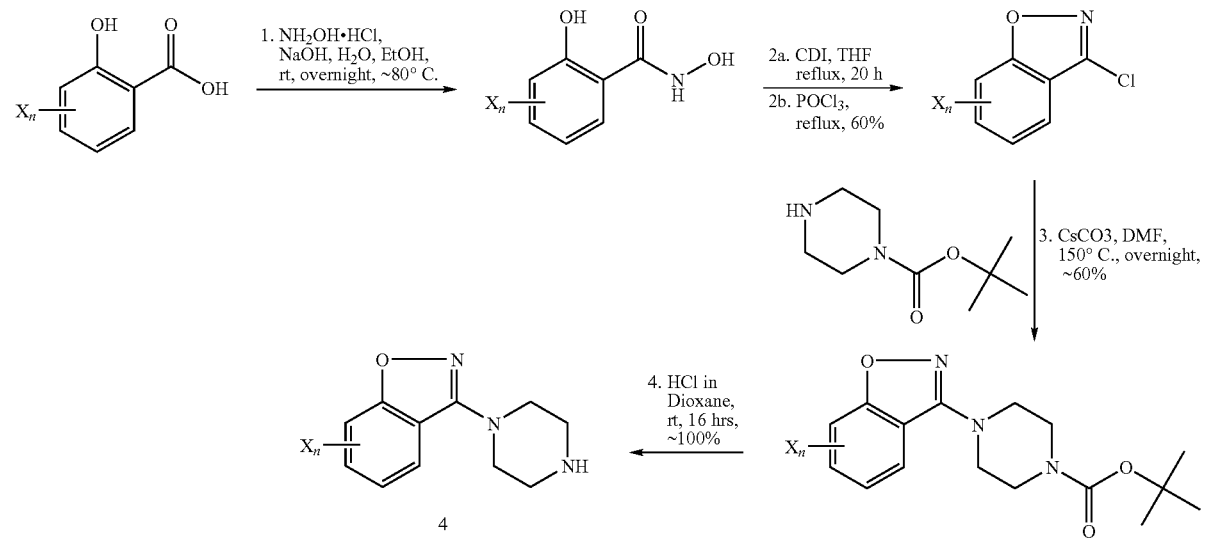

An alternative to the procedure mentioned before to prepare a 3-piperazin-1-yl-1,2-benzisoxazole of formula (4), wherein X and n are as defined above, is to start with an appropriate substituted 2-hydroxybenzoate derivative and prepare the hydroxylamide that can be cyclized using CDI to the substituted hydroxy benzo-isoxazol. Replacement of the hydroxyl group for a chloro can be performed using a chlorinating agent like phosphorus oxychloride. Reaction with piperazine-1-carboxylic acid tert-butyl ester and removal of the BOC protective group under acidic conditions yields the corresponding 3-piperazin-1-yl-1,2-benzisoxazole of formula (4), wherein X and n are as defined above.

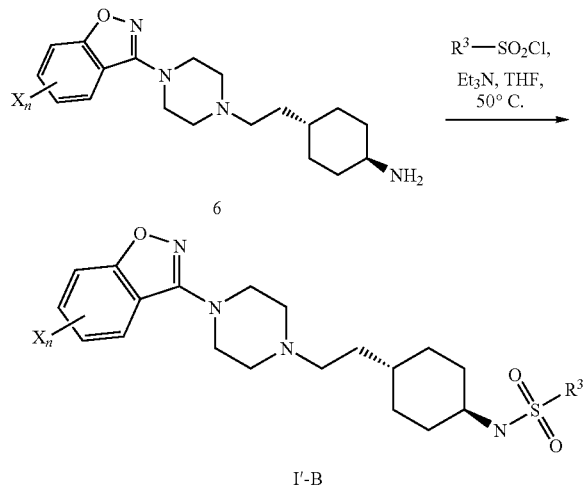

Scheme 4

I'-B

In other examples the intermediate (6), wherein X and n are as defined above, can also react with a sulfonyl chloride in the presence of a base like triethylamine to give the corresponding sulfonyl derivative of the formula (I'-B), wherein X and n are as defined above and $R^3$ is $C_{1-6}$-alkyl.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable hydroxyl group present in the molecule with a acid using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetramethyluronium-tetrafluoroborate (TPTU), or by direct reaction with a suitable acid under acidic conditions, as for example in the presence of a strong mineral acid like hydrochloric acid, sulfuric acid and the like.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

It will be appreciated that the compounds of formula (I) in this invention can be derivatized at functional groups to provide derivatives which are capable of conversion back to the parent compound in vivo.

As described above, the novel compounds of the present invention and their pharmaceutically usable salts and esters possess valuable pharmacological properties and are selective dual modulators of the serotonin 5-$HT_{2a}$ and dopamine $D_3$ receptors. The compounds of the present invention can therefore be used, either alone or in combination with other drugs, for the treatment or prevention of diseases which are modulated by ligands for serotonin 5-$HT_{2a}$ and dopamine $D_3$ receptors. These diseases include, but are not limited to cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions.

The invention also provides pharmaceutical compositions containing a therapeutically effective amount of a compound of formula I or a pharmaceutically acceptable salt thereof and a pharmaceutically acceptable carrier.

The invention also provides methods for treatment and/or the prevention of cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions which comprises administering a compound of formula I or a pharmaceutically acceptable salt thereof.

The invention likewise embraces compounds as described above as well as its pharmaceutically acceptable salt for use as therapeutically active substances, especially as therapeutically active substances for the treatment or prevention of diseases which are related to the serotonin 5-$HT_{2a}$ and dopamine $D_3$ receptors, particularly for the treatment and/or the prevention of cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions.

In another preferred embodiment, the invention provides a method for the treatment or prevention of diseases which are related to the serotonin 5-$HT_{2a}$ and dopamine $D_3$ receptors, particularly for the treatment and/or the prevention of cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions, which method comprises administering a compound as described above as well as its pharmaceutically acceptable salt to a human being or animal.

The invention likewise embraces compounds as described above as well as its pharmaceutically acceptable salt for use in the for use in treatment and/or the prevention of cognitive disorders, drug addiction, depression, anxiety, drug dependence, dementias, memory impairment, psychotic disorders comprising schizophrenia, schizoaffective disorders, bipolar disease, mania, psychotic depression, and psychoses comprising paranoia and delusions.

The invention also embraces the use of compounds as defined above as well as its pharmaceutically acceptable salt for the manufacture of medicaments for the treatment or prevention of diseases which are modulated by ligands for serotonin 5-HT$_{2A}$ and dopamine D$_3$ receptors.

The ability of the compounds to bind to the 5-HT$_{2A}$, D$_3$ and D$_2$ receptors was determined using radioligand binding to cloned receptors selectively expressed in HEK-293 EBNA cells.

Membrane Preparation for Human D$_2$, Human D$_3$ and Human 5-HT$_{2A}$ Receptors HEK-293 EBNA cells were transiently transfected with expression plasmids encoding for the human D$_2$ or D$_3$ dopamine- or for the human 5-HT$_{2A}$ serotonin receptor, respectively. The cells were harvested 48 h post-transfection, washed three times with cold PBS and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at RT, resuspended in assay buffer (D$_2$, D$_3$: 50 mM Tris-HCl, 120 mM NaCl, 5 mM MgCl$_2$, 1 mM EDTA, 5 mM KCl, 1.5 mM CaCl$_2$, pH=7.4; 5-HT$_{2A}$: 50 mM Tris-HCl, 10 mM MgCl$_2$, 1 mM EGTA, pH=7.4), homogenized with a Polytron for 20-30 sec at 12.000 rpm and adjusted to a final concentration of approximately 7.5 μg protein/well (D$_2$, D$_3$) and 15 μg protein/well (5-HT$_{2A}$), respectively.

The binding affinity (K$_i$) of the compounds was determined using radioligand binding. Membranes were incubated in a total volume of 200 μl with a fixed concentration of radioligand (final concentration approximately 0.7 nM [$^3$H]-spiperone for D$_2$, 0.5 nM [$^3$H]-spiperone for D$_3$, and 1.1 nM [$^3$H]-ketanserin for 5-HT$_{2A}$) and ten concentrations of test compound in ranging between 10 μM-0.1 nM for 1 h at RT. At the end of the incubation, the reaction mixtures were filtered on to unifilter 96-well white microplates with bonded GF/C filters (Packard BioScience, Zurich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 μM unlabelled spiperone. Per well 45 μl of Microscint 40 (Perkin Elmer, Schwerzenbach, Switzerland) was added, plates for sealed, shaken for 20 min and counted for 3 min on a Topcount Microplate Scintillation Counter (Canberra Packard SA, Zurich, Switzerland) with quenching correction.

Data Calculation

The CPM value for each duplicate of a concentration of competing compound was averaged (y1), then the % specific binding was calculated according to the equation (((y1−nonspecific)/(total binding-non-specific))×100). Graphs were plotted with the % specific binding using XLfit, a curve fitting program that iteratively plots the data using Levenburg Marquardt algorithm. The single site competition analysis equation used was y=A+((B−A)/(1+((x/C)$^D$))), where y is the % specific binding, A is the minimum y, B is the maximum y, C is the IC$_{50}$, x is the log$_{10}$ of the concentration of the competing compound and D is the slope of the curve (the Hill Coefficient). From these curves the IC$_{50}$ (inhibition concentration at which 50% specific binding of the radioligand was displaced) and Hill coefficient were determined. The affinity constant (K$_i$) was calculated using the Cheng-Prusoff equation K$_i$=(IC$_{50}$/1+([L]/Kd), where [L] is the concentration of radioligand and Kd is the dissociation constant of the radioligand at the receptor as determined by the saturation isotherm.

The compounds of the present invention are selective dual modulators of the serotonin 5-HT$_{2A}$ and dopamine D$_3$ receptors as shown in the activity table hereinafter which gives the K$_i$ values in μM for the human serotonin 5-HT$_{2A}$, human dopamine D$_3$ and human dopamine D$_2$ receptors for some examples of the compounds of the present invention:

Activity table

| Ex. | Compound | Name | K$_i$ 5-HT$_{2A}$ | K$_i$ D$_3$ | K$_i$ D$_2$ |
|---|---|---|---|---|---|
| 1 | [structure] | N-trans-{4-[2-(4-benzo[d]isoxazol-3-yl-piperazin-1-yl)-ethyl]-cyclohexyl}-3-methoxy-propionamide | 0.00488 | 0.0121 | 0.347 |

-continued

Activity table

| Ex. | Compound | Name | $K_i$ 5-HT$_{2A}$ | $K_i$ D$_3$ | $K_i$ D$_2$ |
|---|---|---|---|---|---|
| 2 | | N-trans-{4-[2-(4-benzo[d]isoxazol-3-yl-piperazin-1-yl)-ethyl]-cyclohexyl}-acetamide | 0.00496 | 0.00888 | 0.272 |
| 3 | | N-trans-{4-[2-(4-Benzo[d]isoxazol-3-yl-piperazin-1-yl)-ethyl]-cyclohexyl]-2-trans-(3-methoxy-cyclopentyl)-acetamide | 0.482 | 0.0139 | 0.355 |
| 4 | | N-trans-{4-[2-(4-Benzo[d]isoxazol-3-yl-piperazin-1-yl)-ethyl]-cyclohexyl}-2-hydroxy-acetamide | 0.00336 | 0.0165 | 0.517 |
| 5 | | N-trans-(4-{2-{4-(5-Fluoro-benzo[d]isoxazol-3-yl)-piperazin-1-yl]-ethyl}-cyclohexyl)-3-methoxy-propionamide | 0.0316 | 0.00256 | 0.725 |
| 6 | | N-trans-(4-{2-[4-(5-Fluoro-benzo[d]isoxazol-3-yl)-piperazin-1-yl]-ethyl}-cyclohexyl)-2-trans-(4-methoxy-cyclohexyl)-acetamide | 0.0263 | 0.00644 | 11.8 |

-continued

Activity table

| Ex. | Compound | Name | $K_i$ 5-HT$_{2A}$ | $K_i$ D$_3$ | $K_i$ D$_2$ |
|---|---|---|---|---|---|
| 7 | | Tetrahydro-pyran-4-carboxylic acid-trans-(4-{2-[4-(5-fluoro-benzo[d]isoxazol-3-yl)-piperazin-1-yl]-ethyl}-cyclohexyl)-amide | 0.0138 | 0.0116 | 0.654 |
| 8 | | N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide | 0.0272 | 0.00771 | 1.71 |
| 9 | | N-trans-(4-{2-[4-(5-Fluoro-benzo[d]isoxazol-3-yl)-piperazin-1-yl]-ethyl}-cyclohexyl)-2-methoxy-acetamide | 0.0233 | 0.00749 | 1.86 |
| 10 | | N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide | 0.0104 | 0.0066 | 11.5 |
| 11 | | N-trans-(4-{2-[4-(5-Fluoro-benzo[d]isoxazol-3-yl)-piperazin-1-yl]-ethyl}-cyclohexyl)-3-hydroxy-3-methyl-butyramide | 0.0240 | 0.00482 | 0.482 |

-continued

Activity table

| Ex. | Compound | Name | $K_i$ 5-HT$_{2A}$ | $K_i$ D$_3$ | $K_i$ D$_2$ |
|---|---|---|---|---|---|
| 12 | | 2-Ethoxy-N-trans-(4-{2-[4-(5-fluoro-benzo[d]isoxazol-3-yl)-piperazin-1-yl]-ethyl}-cyclohexyl)-acetamide | 0.0235 | 0.0156 | 1.39 |
| 13 | | 4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide | 0.0351 | 0.0414 | 3.44 |
| 14 | | N-trans-(4-{2-[4-(5-Fluoro-benzo[d]isoxazol-3-yl)-piperazin-1-yl]-ethyl}-cyclohexyl)-methanesulfonamide | 0.0281 | 0.00337 | 1.07 |
| 15 | | 2-[1,4]Dioxan-2-yl-N-trans-(4-{2-[4-(5-fluoro-benzo[d]isoxazol-3-yl)-piperazin-1-yl]-ethyl}-cyclohexyl)-acetamide | 0.0154 | 0.00634 | 0.752 |
| 16 | | 3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide | 0.0144 | 0.0214 | 1.44 |

-continued

| | | | Activity table | | |
|---|---|---|---|---|---|
| Ex. | Compound | Name | $K_i$ 5-HT$_{2A}$ | $K_i$ D$_3$ | $K_i$ D$_2$ |
| 17 | | N-trans-(4-{2-[4-(5-Fluoro-benzo[d]isoxazol-3-yl)-piperazin-1-yl]-ethyl}-cyclohexyl)-malonamide | 0.0254 | 0.00183 | 0.592 |
| 18 | | Rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide | 0.0252 | 0.0121 | 0.891 |
| 19 | | N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide | 0.0206 | 0.0360 | 1.02 |
| 20 | | N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide | 0.0193 | 0.00555 | 0.386 |

-continued

Activity table

| Ex. | Compound | Name | $K_i$ 5-HT$_{2A}$ | $K_i$ D$_3$ | $K_i$ D$_2$ |
|---|---|---|---|---|---|
| 21 | | N-trans-(4-{2-[4-(5-Fluoro-benzo[d]isoxazol-3-yl)-piperazin-1-yl]-ethyl}-cyclohexyl)-2-(3-methyl-oxetan-3-yl)-acetamide | 0.0111 | 0.00261 | 0.307 |
| 22 | Chiral | 2-((S)-2,2-Dimethyl-tetrahydro-pyran-4-yl)-N-(4-{2-[4-(5-fluoro-benzo[d]isoxazol-3-yl)-piperazin-1-yl]-ethyl}-cyclohexyl)-acetamide | 0.0327 | 0.00781 | 1.03 |
| 23 | Chiral | 2-((R)-2,2-Dimethyl-tetrahydro-pyran-4-yl)-N-(4-{2-[4-(5-fluoro-benzo[d]isoxazol-3-yl)-piperazin-1-yl]-ethyl}-cyclohexyl)-acetamide | 0.0268 | 0.00703 | 1.06 |
| 24 | | 2-[1,3]Dioxan-2-yl-N-trans-(4-{2-[4-(5-fluoro-benzo[d]isoxazol-3-yl)-piperazin-1-yl]-ethyl}-cyclohexyl)-acetamide | 0.0168 | 0.00455 | 1.07 |
| 25 | | N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide | 0.0133 | 0.0141 | 0.496 |

-continued
Activity table
| Ex. | Compound | Name | $K_i$ 5-HT$_{2A}$ | $K_i$ D$_3$ | $K_i$ D$_2$ |
|---|---|---|---|---|---|
| 26 | 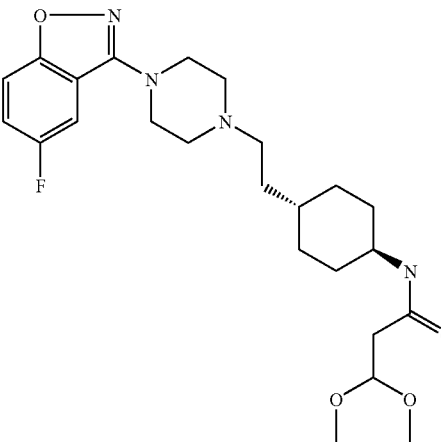 | N-trans-(4-{2-[4-(5-Fluoro-benzo[d]isoxazol-3-yl)-piperazin-1-yl]-ethyl}-cyclohexyl)-3,3-dimethoxy-propionamide | 0.0159 | 0.00212 | 0.761 |
| 27 | 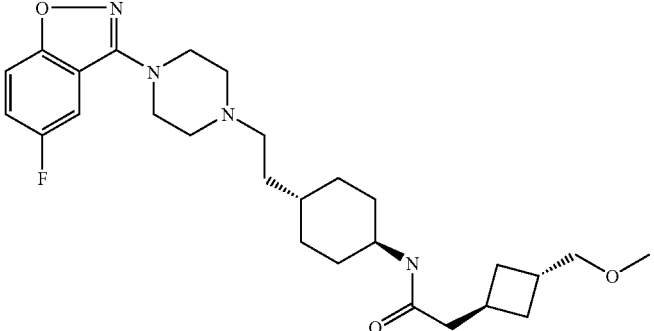 | N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide | 0.0262 | 0.0100 | 0.718 |
| 28 | 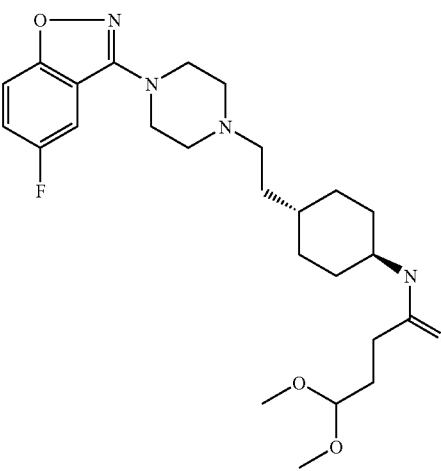 | N-trans-(4-{2-[4-(5-Fluoro-benzo[d]isoxazol-3-yl)-piperazin-1-yl]-ethyl}-cyclohexyl)-4,4-dimethoxy-butyramide | 0.0228 | 0.00878 | 0.918 |

-continued
Activity table
| Ex. | Compound | Name | $K_i$ 5-HT$_{2A}$ | $K_i$ D$_3$ | $K_i$ D$_2$ |
|---|---|---|---|---|---|
| 29 | 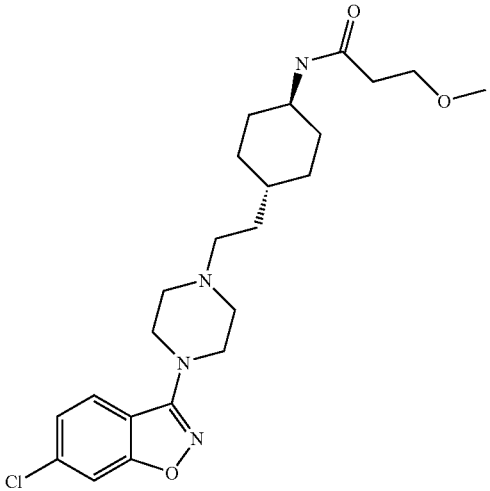 | N-trans-(4-{2-[4-(6-Chloro-benzo[d]isoxazol-3-yl)-piperazin-1-yl]-ethyl}-cyclohexyl)-3-methoxy-propionamide | 0.00859 | 0.00868 | 0.490 |
| 30 | 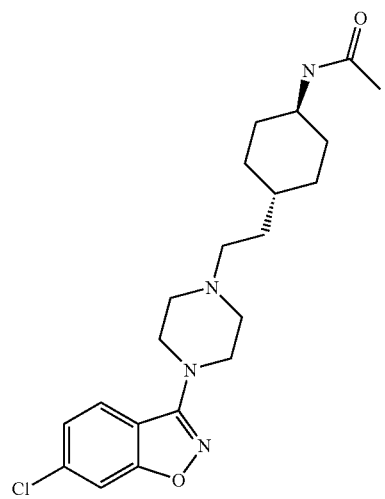 | N-trans-(4-{2-[4-(6-Chloro-benzo[d]isoxazol-3-yl)-piperazin-1-yl]-ethyl}-cyclohexyl)-acetamide | 0.00865 | 0.00918 | 0.675 |
| 31 | 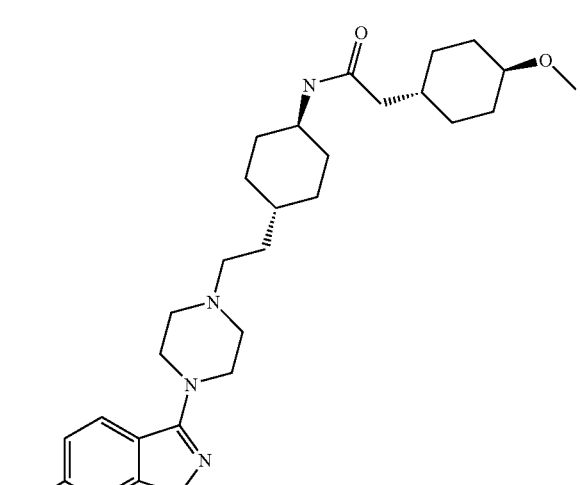 | N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide | 0.0029 | 0.00889 | 4.99 |

-continued

Activity table

| Ex. | Compound | Name | $K_i$ 5-HT$_{2A}$ | $K_i$ D$_3$ | $K_i$ D$_2$ |
|---|---|---|---|---|---|
| 32 | | Tetrahydro-pyran-4-carboxylic acid N-trans-(4-{2-[4-(6-chloro-benzo[d]isoxazol-3-yl)-piperazin-1-yl]-ethyl}-cyclohexyl)-amide | 0.00237 | 0.0159 | 3.04 |
| 33 | | N-trans-(4-{2-[4-(6-Chloro-benzo[d]isoxazol-3-yl)-piperazin-1-yl]-ethyl}-cyclohexyl)-rac-3,3,3-trifluoro-2-hydroxy-propionamide | 0.0124 | 0.0148 | 0.362 |
| 34 | | Tetrahydro-furan-3-carboxylic acid N-trans-(4-{2-[4-(6-chloro-benzo[d]isoxazol-3-yl)-piperazin-1-yl]-ethyl}-cyclohexyl)-amide | 0.0104 | 0.0188 | 0.193 |
| 35 | | N-trans-(4-{2-[4-(6-Chloro-benzo[d]isoxazol-3-yl)-piperazin-1-yl]-ethyl}-cyclohexyl)-2-(tetrahydro-pyran-2-yl)-acetamide | 0.0048 | 0.0172 | 0.899 |
| 36 | | N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide | 0.00274 | 0.0101 | 0.683 |
| 37 | | N-trans-(4-{2-[4-(6-Chloro-benzo[d]isoxazol-3-yl)-piperazin-1-yl]-ethyl}-cyclohexyl)-3-methoxy-butyramide | 0.00732 | 0.0149 | 0.350 |

-continued

Activity table

| Ex. | Compound | Name | $K_i$ 5-HT$_{2A}$ | $K_i$ D$_3$ | $K_i$ D$_2$ |
| --- | --- | --- | --- | --- | --- |
| 38 | | 1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide | 0.00819 | 0.0125 | 0.314 |
| 39 | | N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide | 0.00414 | 0.02344 | 3.80 |
| 40 | | N-trans-(4-{2-[4-(6-Chloro-benzo[d]isoxazol-3-yl)-piperazin-1-yl]-ethyl}-cyclohexyl)-2-(tetrahydro-pyran-4-yl)-acetamide | 0.0113 | 0.00702 | 1.0764 |
| 41 | | N-trans-(4-{2-[4-(6-Chloro-benzo[d]isoxazol-3-yl)-piperazin-1-yl]-ethyl}-cyclohexyl)-propionamide | 0.0109 | 0.0087 | 0.675 |
| 42 | | N-trans-(4-{2-[4-(6-Chloro-benzo[d]isoxazol-3-yl)-piperazin-1-yl]-ethyl}-cyclohexyl)-2-hydroxy-acetamide | 0.00699 | 0.0110 | 0.809 |
| 43 | | N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide | 0.00322 | 0.0125 | 2.92 |
| 44 | | N-trans-(4-{2-[4-(6-Chloro-benzo[d]isoxazol-3-yl)-piperazin-1-yl]-ethyl}-cyclohexyl)-3-hydroxy-3-methyl-butyramide | 0.00659 | 0.0101 | 0.325 |

Activity table

| Ex. | Compound | Name | $K_i$ 5-HT$_{2A}$ | $K_i$ D$_3$ | $K_i$ D$_2$ |
|---|---|---|---|---|---|
| 45 | Chiral | (S)-N-(4-{2-[4-(6-Chloro-benzo[d]isoxazol-3-yl)-piperazin-1-yl]-ethyl}-cyclohexyl)-3-hydroxy-butyramide | 0.00921 | 0.0158 | 0.356 |
| 46 | Chiral | (S)-Tetrahydro-furan-3-carboxylic acid (4-{2-[4-(6-chloro-benzo[d]isoxazol-3-yl)-piperazin-1-yl]-ethyl}-cyclohexyl)-amide | 0.0109 | 0.0209 | 0.488 |
| 47 | | N-trans-(4-{2-[4-(6-Chloro-benzo[d]isoxazol-3-yl)-piperazin-1-yl]-ethyl}-cyclohexyl)-2-oxetan-3-yl-acetamide | 0.00659 | 0.00814 | 0.238 |
| 48 | | N-trans-(4-{2-[4-(6-Chloro-benzo[d]isoxazol-3-yl)-piperazin-1-yl]-ethyl}-cyclohexyl)-2-trans-(3-methoxymethyl-cyclobutyl)-acetamide | 0.00377 | 0.00996 | 0.706 |

-continued

Activity table

| Ex. | Compound | Name | $K_i$ 5-HT$_{2A}$ | $K_i$ D$_3$ | $K_i$ D$_2$ |
|---|---|---|---|---|---|
| 49 | Chiral | N-trans-(4-{2-[4-(6-Chloro-benzo[d]isoxazol-3-yl)-piperazin-1-yl]-ethyl}-cyclohexyl)-2-(R)-tetrahydro-pyran-2-yl-acetamide | 0.00848 | 0.0206 | 1.02 |
| 50 | Chiral | N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide | 0.00478 | 0.0237 | 1.16 |
| 51 | | N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide | 0.00337 | 0.0104 | 3.02 |
| 52 | | N-trans-(4-{2-[4-(6-Chloro-benzo[d]isoxazol-3-yl)-piperazin-1-yl]-ethyl}-cyclohexyl)-2-cyclopropyl-acetamide | 0.00507 | 0.00384 | 0.315 |
| 53 | | N-trans-(4-{2-[4-(6-Chloro-benzo[d]isoxazol-3-yl)-piperazin-1-yl]-ethyl}-cyclohexyl)-3,3,3-trifluoro-propionamide | 0.00514 | 0.00274 | 0.172 |

-continued

Activity table

| Ex. | Compound | Name | $K_i$ 5-HT$_{2A}$ | $K_i$ D$_3$ | $K_i$ D$_2$ |
|---|---|---|---|---|---|
| 54 | | 4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide | 0.0083 | 0.0502 | 3.85 |
| 55 | | N-trans-(4-{2-[4-(6-Chloro-benzo[d]isoxazol-3-yl)-piperazin-1-yl]-ethyl}-cyclohexyl)-3,3-dimethoxy-propionamide | 0.0076 | 0.00616 | 0.396 |
| 56 | | N-trans-(4-{2-[4-(5,6-Difluoro-benzo[d]isoxazol-3-yl)-piperazin-1-yl]-ethyl}-cyclohexyl)-acetamide | 0.012 | 0.00583 | 0.380 |
| 57 | | N-trans-(4-{2-[4-(5,6-Difluoro-benzo[d]isoxazol-3-yl)-piperazin-1-yl]-ethyl}-cyclohexyl)-3-methoxy-propionamide | 0.0131 | 0.00618 | 0.396 |
| 58 | | N-trans-(4-{2-[4-(5,6-Difluoro-benzo[d]isoxazol-3-yl)-piperazin-1-yl]-ethyl}-cyclohexyl)-2-trans-(4-methoxy-cyclohexyl)-acetamide | 0.00759 | 0.0144 | 11.3 |

-continued

Activity table

| Ex. | Compound | Name | $K_i$ 5-HT$_{2A}$ | $K_i$ D$_3$ | $K_i$ D$_2$ |
|---|---|---|---|---|---|
| 59 | | N-trans-(4-{2-[4-(5,6-Difluoro-benzo[d]isoxazol-3-yl)-piperazin-1-yl]-ethyl}-cyclohexyl)-propionamide | 0.0148 | 0.00988 | 0.389 |
| 60 | | N-trans-(4-{2-[4-(5,6-Difluoro-benzo[d]isoxazol-3-yl)-piperazin-1-yl]-ethyl}-cyclohexyl)-2-methoxy-acetamide | 0.0095 | 0.0204 | 0.878 |
| 61 | | N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide | 0.00845 | 0.0101 | 0.811 |
| 62 | | N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide | 0.00992 | 0.0134 | 0.352 |
| 63 | | N-trans-(4-{2-[4-(5,6-Difluoro-benzo[d]isoxazol-3-yl)-piperazin-1-yl]-ethyl}-cyclohexyl)-2-(tetrahydro-pyran-4-yl)-acetamide | 0.00688 | 0.00713 | 9.71 |
| 64 | | N-trans-(4-{2-[4-(5,6-Difluoro-benzo[d]isoxazol-3-yl)-piperazin-1-yl]-ethyl}-cyclohexyl)-3-hydroxy-3-methyl-butyramide | 0.0118 | 0.0101 | 0.598 |
| 65 | | N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide | 0.0044 | 0.00767 | 0.822 |

-continued

Activity table

| Ex. | Compound | Name | $K_i$ 5-HT$_{2A}$ | $K_i$ D$_3$ | $K_i$ D$_2$ |
|---|---|---|---|---|---|
| 66 | | 4-Methoxy-cyclohexanecarboxylic acid N-trans(4-{2-[4-(5,6-difluoro-benzo[d]isoxazol-3-yl)-piperazin-1-yl]-ethyl}-cyclohexyl)-amide | 0.00694 | 0.0263 | 2.93 |
| 67 | | Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide | 0.00772 | 0.0300 | 2.67 |
| 68 | | Ethanesulfonic acid N-trans-(4-{2-[4-(5,6-difluoro-benzo[d]isoxazol-3-yl)-piperazin-1-yl]-ethyl}-cyclohexyl)-amide | 0.0178 | 0.0164 | 0.641 |
| 69 | | N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide | 0.00633 | 0.0131 | 0.862 |
| 70 | | N-trans-(4-{2-{4-(6-Chloro-5-fluoro-benzo[d]isoxazol-3-yl)-piperazin-1-yl]-ethyl}-cyclohexyl)-propionamide | 0.0681 | 0.00715 | 0.852 |

-continued
Activity table
| Ex. | Compound | Name | $K_i$ 5-HT$_{2A}$ | $K_i$ D$_3$ | $K_i$ D$_2$ |
|---|---|---|---|---|---|
| 71 | 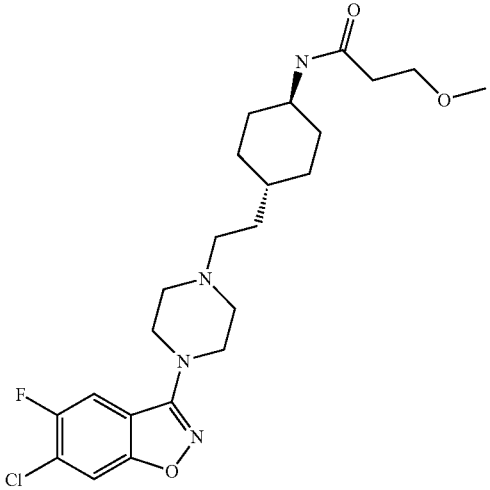 | N-trans-(4-{2-[4-(6-Chloro-5-fluoro-benzo[d]isoxazol-3-yl)-piperazin-1-yl]-ethyl}-cyclohexyl)-3-methoxy-propionamide | 0.0892 | 0.0201 | 1.43 |
| 72 | 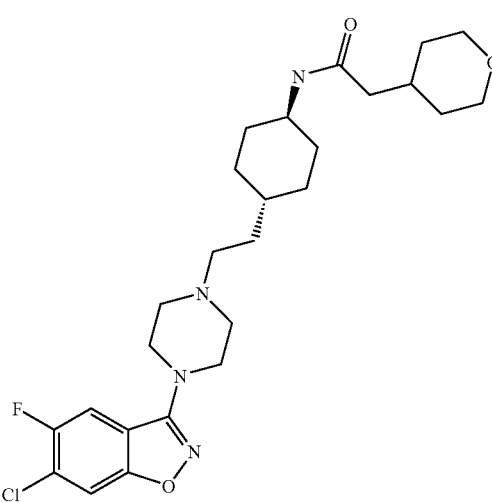 | N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide | 0.0366 | 0.0243 | 11.3 |
| 73 | 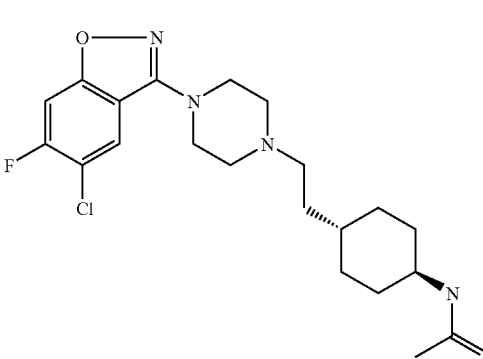 | N-trans-(4-{2-[4-(5-Chloro-6-fluoro-benzo[d]isoxazol-3-yl)-piperazin-1-yl]-ethyl}-cyclohexyl)-acetamide | 0.0168 | 0.00974 | 0.559 |

-continued
Activity table
| Ex. | Compound | Name | $K_i$ 5-HT$_{2A}$ | $K_i$ D$_3$ | $K_i$ D$_2$ |
|---|---|---|---|---|---|
| 74 | 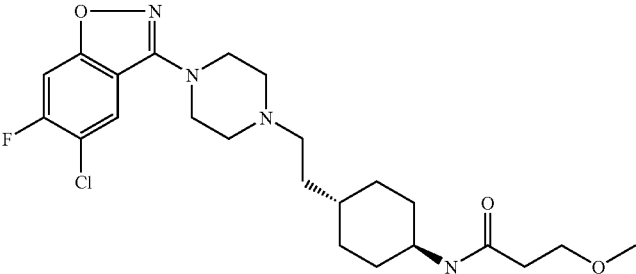 | N-trans-(4-{2-[4-(5-Chloro-6-fluoro-benzo[d]isoxazol-3-yl)-piperazin-1-yl]-ethyl}-cyclohexyl)-3-methoxy-propionamide | 0.0122 | 0.0101 | 0.260 |
| 75 | 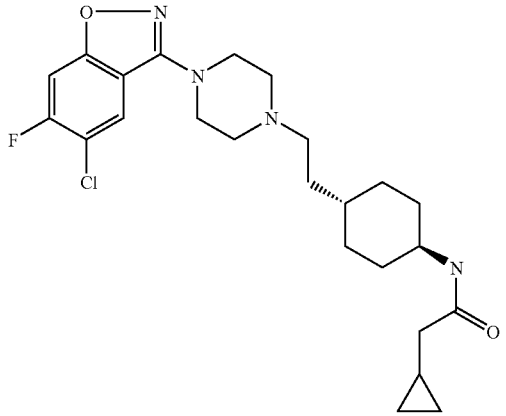 | N-trans-(4-{2-[4-(5-Chloro-6-fluoro-benzo[d]isoxazol-3-yl)-piperazin-1-yl]-ethyl}-cyclohexyl)-2-cyclopropyl-acetamide | 0.00592 | 0.00165 | 1.50 |
| 76 | 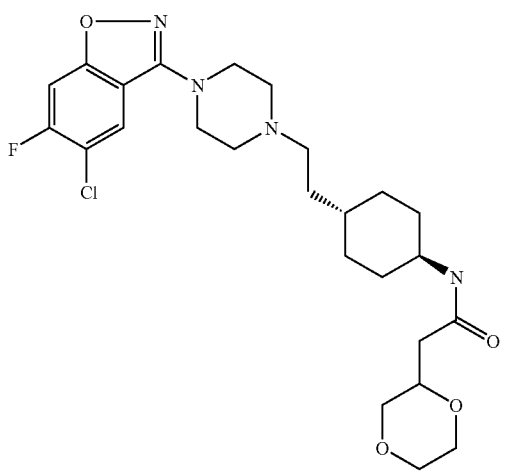 | N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide | 0.0204 | 0.0199 | 0.632 |

-continued

Activity table

| Ex. | Compound | Name | $K_i$ 5-HT$_{2A}$ | $K_i$ D$_3$ | $K_i$ D$_2$ |
|---|---|---|---|---|---|
| 77 | 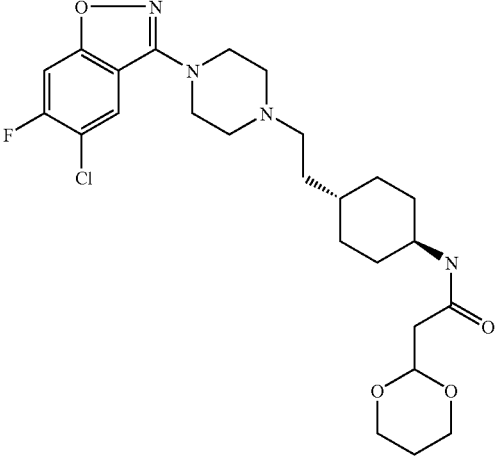 | N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide | 0.00226 | 0.00606 | 2.30 |
| 78 | 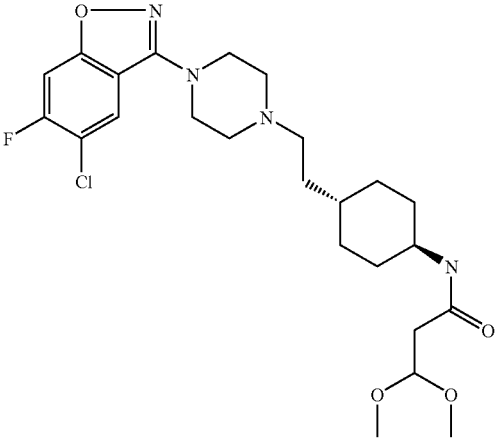 | N-trans-(4-{2-[4-(5-Chloro-6-fluoro-benzo[d]isoxazol-3-yl)-piperazin-1-yl]-ethyl}-cyclohexyl)-3,3-dimethoxy-propionamide | 0.00505 | 0.00626 | 1.31 |
| 79 | 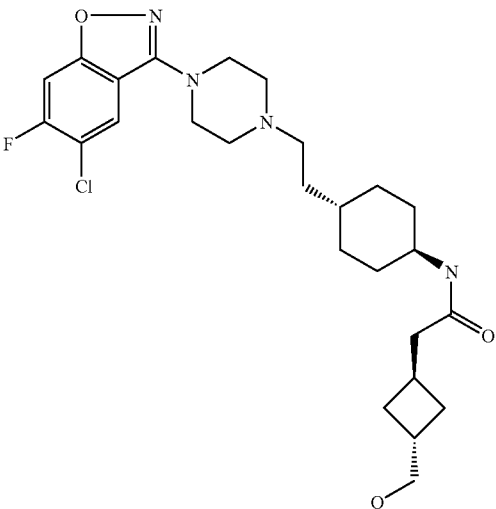 | N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide | 0.00248 | 0.00547 | 6.87 |

-continued

Activity table

| Ex. | Compound | Name | $K_i$ 5-HT$_{2A}$ | $K_i$ D$_3$ | $K_i$ D$_2$ |
|---|---|---|---|---|---|
| 80 | | N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide | 0.00298 | 0.00642 | 11.7 |
| 81 | | N-trans-(4-{2-[4-(5-Chloro-6-fluoro-benzo[d]isoxazol-3-yl)-piperazin-1-yl]-ethyl}-cyclohexyl)-3-methylsulfanyl-propionamide | 0.00528 | 0.00438 | 11.1 |
| 82 | | N-trans-(4-{2-[4-(5-Chloro-6-fluoro-benzo[d]isoxazol-3-yl)-piperazin-1-yl]-ethyl}-cyclohexyl)-2-(3-methyl-isoxazol-5-yl)-acetamide | 0.00299 | 0.00137 | 11.1 |
| 83 | | 3-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide | 0.00855 | 0.00585 | 11.1 |

-continued

Activity table

| Ex. | Compound | Name | $K_i$ 5-HT$_{2A}$ | $K_i$ D$_3$ | $K_i$ D$_2$ |
|---|---|---|---|---|---|
| 84 | | 5-Chloro-thiophene-2-carboxylic acid N-trans-(4-{2-[4-(5-chloro-6-fluoro-benzo[d]isoxazol-3-yl)-piperazin-1-yl]-ethyl}-cyclohexyl)-amide | 0.00711 | 0.00294 | 0.258 |
| 85 | | 5-Methoxy-thiophene-2-carboxylic acid N-trans-(4-{2-[4-(5-chloro-6-fluoro-benzo[d]isoxazol-3-yl)-piperazin-1-yl]-ethyl}-cyclohexyl)-amide | 0.00747 | 0.0082 | 0.368 |
| 86 | | N-trans-(4-{2-[4-(5-Chloro-6-fluoro-benzo[d]isoxazol-3-yl)-piperazin-1-yl]-ethyl}-cyclohexyl)-propionamide | 0.00953 | 0.00516 | 0.250 |
| 87 | | N-trans-(4-{2-[4-(5-Chloro-6-fluoro-benzo[d]isoxazol-3-yl)-piperazin-1-yl]-ethyl}-cyclohexyl)-2-hydroxy-acetamide | 0.0086 | 0.00997 | 0.401 |
| 88 | | N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide | 0.0167 | 0.0311 | 11.2 |

-continued

Activity table

| Ex. | Compound | Name | $K_i$ 5-HT$_{2A}$ | $K_i$ D$_3$ | $K_i$ D$_2$ |
|---|---|---|---|---|---|
| 89 | | N-trans-(4-{2-[4-(5-Chloro-6-fluoro-benzo[d]isoxazol-3-yl)-piperazin-1-yl]-ethyl}-cyclohexyl)-2-methanesulfonyl-acetamide | 0.00289 | 0.00572 | 11.2 |
| 90 | | N-trans-(4-{2-[4-(5-Chloro-6-fluoro-benzo[d]isoxazol-3-yl)-piperazin-1-yl]-ethyl}-cyclohexyl)-3-methanesulfonyl-propionamide | 0.00764 | 0.0143 | 1.19 |
| 91 | | N-trans-(4-{2-[4-(5-Chloro-6-fluoro-benzo[d]isoxazol-3-yl)-piperazin-1-yl]-ethyl}-cyclohexyl)-carbamic acid methyl ester | 0.00184 | 0.00058 | 0.197 |
| 92 | | Cyclobutanecarboxylic acid N-trans-(4-{2-[4-(5-chloro-6-fluoro-benzo[d]isoxazol-3-yl)-piperazin-1-yl]-ethyl}-cyclohexyl)-amide | 0.0116 | 0.0124 | 4.07 |
| 93 | | N-trans-(4-{2-[4-(5-Chloro-6-fluoro-benzo[d]isoxazol-3-yl)-piperazin-1-yl]-ethyl}-cyclohexyl)-3,3,3-trifluoro-propionamide | 0.006 | 0.00196 | |

Activity table

| Ex. | Compound | Name | $K_i$ 5-HT$_{2A}$ | $K_i$ D$_3$ | $K_i$ D$_2$ |
|---|---|---|---|---|---|
| 94 | 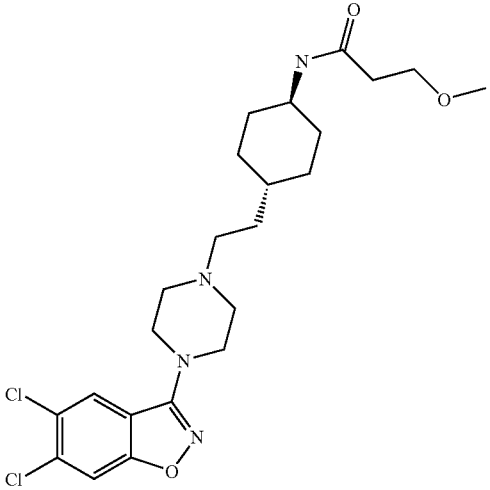 | N-trans-(4-{2-[4-(5,6-Dichloro-benzo[d]isoxazol-3-yl)-piperazin-1-yl]-ethyl}-cyclohexyl)-3-methoxy-propionamide | 0.0263 | 0.00223 | 1.97 |
| 95 | 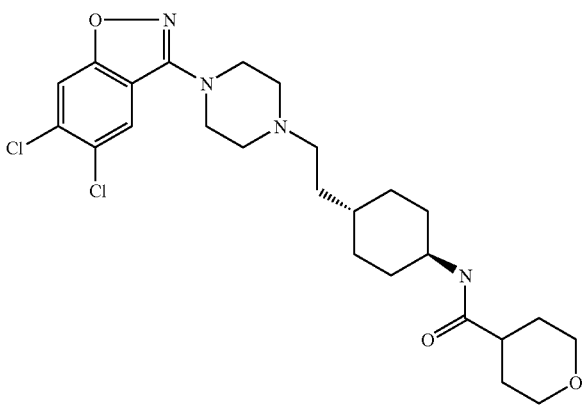 | Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide | 0.0499 | 0.117 | 7.95 |
| 96 | 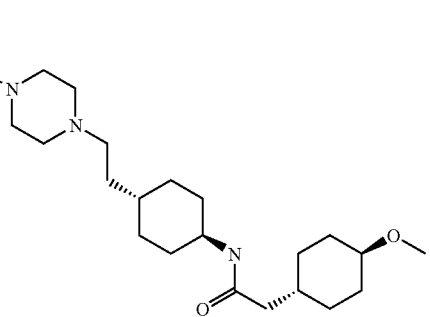 | N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide | 0.0514 | 0.0354 | 11.6 |

-continued

Activity table

| Ex. | Compound | Name | $K_i$ 5-HT$_{2A}$ | $K_i$ D$_3$ | $K_i$ D$_2$ |
|---|---|---|---|---|---|
| 97 | | N-trans-(4-{2-[4-(5,6-Dichloro-benzo[d]isoxazol-3-yl)-piperazin-1-yl]-ethyl}-cyclohexyl)-2-(tetrahydro-pyran-4-yl)-acetamide | 0.0307 | 0.00945 | 11.6 |
| 98 | | 3-Methoxy-N-trans-(4-{2-[4-(6-methyl-benzo[d]isoxazol-3-yl)-piperazin-1-yl]-ethyl}-cyclohexyl)-propionamide | 0.00521 | 0.00742 | 0.222 |
| 99 | | N-trans-(4-{2-[4-(6-Methyl-benzo[d]isoxazol-3-yl)-piperazin-1-yl]-ethyl}-cyclohexyl)-propionamide | 0.00592 | 0.0058 | 0.207 |
| 100 | | 2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide | 0.0053 | 0.0177 | 0.494 |

-continued

Activity table

| Ex. | Compound | Name | $K_i$ 5-HT$_{2A}$ | $K_i$ D$_3$ | $K_i$ D$_2$ |
|---|---|---|---|---|---|
| 101 | | 2-[1,3]Dioxan-2-yl-N-trans-(4-{2-[4-(6-methyl-benzo[d]isoxazol-3-yl)-piperazin-1-yl]-ethyl}-cyclohexyl)-acetamide | 0.00515 | 0.00833 | 0.384 |
| 102 | | 2-[1,4]Dioxan-2-yl-N-trans-(4-{2-[4-(6-methyl-benzo[d]isoxazol-3-yl)-piperazin-1-yl]-ethyl}-cyclohexyl)-acetamide | 0.00265 | 0.0139 | 0.333 |
| 103 | | 3,3-Dimethoxy-N-trans-(4-{2-[4-(6-methyl-benzo[d]isoxazol-3-yl)-piperazin-1-yl]-ethyl}-cyclohexyl)-propionamide | 0.0023 | 0.00696 | 0.206 |
| 104 | | 3-Methoxy-N-trans-(4-{2-[4-(5-methyl-benzo[d]isoxazol-3-yl)-piperazin-1-yl]-ethyl}-cyclohexyl)-propionamide | 0.0209 | 0.00259 | 0.554 |
| 105 | | 2-Methanesulfonyl-N-trans-(4-{2-[4-(6-methyl-benzo[d]isoxazol-3-yl)-piperazin-1-yl]-ethyl}-cyclohexyl)-acetamide | 0.004 | 0.005 | 0.170 |
| 106 | | N-trans-(4-{2-[4-(6-Fluoro-5-methyl-benzo[d]isoxazol-3-yl)-piperazin-1-yl]-ethyl}-cyclohexyl)-acetamide | 0.0319 | 0.00904 | 2.38 |

-continued

Activity table

| Ex. | Compound | Name | K$_i$ 5-HT$_{2A}$ | K$_i$ D$_3$ | K$_i$ D$_2$ |
|---|---|---|---|---|---|
| 107 | | N-trans-(4-{2-[4-(6-Fluoro-5-methyl-benzo[d]isoxazol-3-yl)-piperazin-1-yl]-ethyl}-cyclohexyl)-2-methoxy-acetamide | 0.0112 | 0.0200 | 0.674 |
| 108 | | N-trans-(4-{2-[4-(6-Fluoro-5-methyl-benzo[d]isoxazol-3-yl)-piperazin-1-yl]-ethyl}-cyclohexyl)-3-methoxy-propionamide | 0.0189 | 0.00800 | 0.297 |
| 109 | | 2-Cyclopropyl-N-trans-(4-{2-[4-(6-fluoro-5-methyl-benzo[d]isoxazol-3-yl)-piperazin-1-yl]-ethyl}-cyclohexyl)-acetamide | 0.0326 | 0.0145 | 10.0 |
| 110 | | 2-Ethoxy-N-trans-(4-{2-[4-(6-fluoro-5-methyl-benzo[d]isoxazol-3-yl)-piperazin-1-yl]-ethyl}-cyclohexyl)-acetamide | 0.0101 | 0.0316 | 1.55 |
| 111 | | 2-[1,3]Dioxan-2-yl-N-trans-(4-{2-[4-(6-fluoro-5-methyl-benzo[d]isoxazol-3-yl)-piperazin-1-yl]-ethyl}-cyclohexyl)-acetamide | 0.00766 | 0.0106 | 4.04 |

-continued

Activity table

| Ex. | Compound | | Name | $K_i$ 5-HT$_{2A}$ | $K_i$ D$_3$ | $K_i$ D$_2$ |
|---|---|---|---|---|---|---|
| 112 | | | N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide | 0.00351 | 0.00433 | 0.119 |
| 113 | | | 2-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide | 0.014 | 0.025 | >10.5 |
| 114 | | Chiral | 2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide | 0.017 | 0.031 | >9.7 |
| 115 | | Chiral | 2-(S)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide | 0.010 | 0.038 | >9.7 |
| 116 | | Chiral | (S)-4,4,4-Trifluoro-N-trans-(4-{2-[4-(6-fluoro-5-methyl-benzo[d]isoxazol-3-yl)-piperazin-1-yl]-ethyl}-cyclohexyl)-3-hydroxy-butyramide | 0.033 | 0.020 | 3.28 |

-continued

Activity table

| Ex. | Compound | Name | $K_i$ 5-HT$_{2A}$ | $K_i$ D$_3$ | $K_i$ D$_2$ |
|---|---|---|---|---|---|
| 117 | | N-trans-(4-{2-[4-(6-Fluoro-5-methyl-benzo[d]isoxazol-3-yl)-piperazin-1-yl]-ethyl}-cyclohexyl)-2-(tetrahydro-pyran-2-yl)-acetamide | 0.008 | 0.033 | >2 |
| 118 | | N-trans-(4-{2-[4-(6-Fluoro-5-methyl-benzo[d]isoxazol-3-yl)-piperazin-1-yl]-ethyl}-cyclohexyl)-2-(tetrahydro-furan-2-yl)-acetamide | 0.021 | 0.022 | 1.072 |
| 119 | | N-trans-(4-{2-[4-(6-Fluoro-5-methyl-benzo[d]isoxazol-3-yl)-piperazin-1-yl]-ethyl}-cyclohexyl)-2-methoxy-propionamide | 0.010 | 0.053 | 2.27 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such as carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for supposi-tories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples illustrate the present invention without limiting it.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and tilled into capsules or size 2.

Example C

Injection solutions can have the following composition:

| Ingredients | Per injection |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Ingredients | Per capsule |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Ingredients | Per sachet |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The following examples 1 to 119 are provided for illustration of the invention. They should not be considered as limiting the scope of the invention, but merely as being representative thereof.

Example 1

N-trans-{4-[2-(4-benzo[d]isoxazol-3-yl)-piperazin-1-yl)-ethyl]-cyclohexyl}-3-methoxy-propionamide

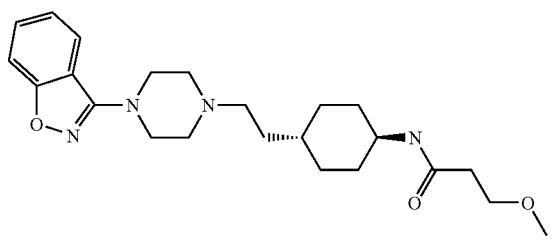

Step 1: trans-{4-[2-(4-Benzo[d]isoxazol-3-yl-piperazin-1-yl)-ethyl]-cyclohexyl}-carbamic acid tert-butyl ester

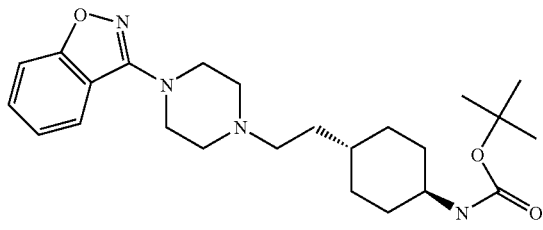

A mixture of 3-piperazin-1-yl-1,2-benzisoxazole (1 g, 4.92 mmol), trans-[4-(2-oxo-ethyl)-cyclohexyl]-carbamic acid tert-butyl ester (Intermediate A) (1.3 g, 5.41 mmol), in dichloromethane (15 ml) was stirred for 15 minutes at room temperature and sodium triacetoxyborohydride (1.88 g, 8.86 mmol) was added slowly and the resulting solution was stirred for 12 hours until the TLC indicated completion of the reaction. The mixture was extracted with saturated NaHCO$_3$-solution and two times dichloromethane. The organic layers were dried over sodium sulfate, filtrated and concentrated to dryness. The crude product was purified with column chromatography on silica gel using heptane:ethyl acetate 80:20->10:90. The product fractions were concentrated to give 1.34 g (64% yield) of a white solid. MS (m/e): 429.4 (M+H$^+$).

Step 2: trans-4-[2-(4-Benzo[d]isoxazol-3-yl-piperazin-1-yl)-ethyl]-cyclohexylamine hydrochloride

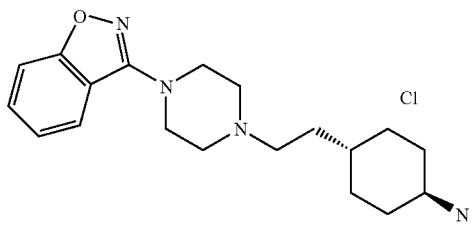

Trans-{4-[2-(4-Benzo[d]isoxazol-3-yl-piperazin-1-yl)-ethyl]-cyclohexyl}-carbamic acid tert-butyl ester (1.3 g, 3.03 mmol) was dissolved in 3 ml dichloromethane and 4N HCl in dioxane (15.2 ml, 60.7 mmol) was added. The white suspension was stirred for 4 hours at room temperature, diluted with diisopropylether and filtered. The crystals were washed with diisopropylether and dried for 1 hour at 50° C. and <20 mbar, to get the desired salt as a white solid (1.2 g, quant.) [MS: m/e=329.2 (M+H$^+$)].

Step 3: N-trans-{4-[2-(4-benzo[d]isoxazol-3-yl-piperazin-1-yl)-ethyl]-cyclohexyl}-3-methoxy-propionamide

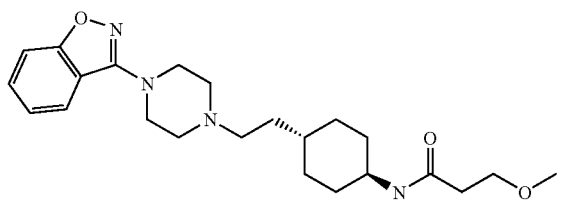

Trans-4-[2-(4-Benzo[d]isoxazol-3-yl-piperazin-1-yl)-ethyl]-cyclohexylamine hydrochloride (100 mg, 0.27 mmol), 3-methoxypropionic acid (31 mg, 0.30 mmol) and N-ethyl-diisopropylamine (140 μl, 0.820 mmol) were dissolved in DMF (2 ml). 2-(1H-benzotriazol-1-yl)-1,1,3,3-tetramethyl uronium tetrafluoroborate (TBTU) (100 mg, 0.32 mmol) was added and the mixture was stirred for 12 hours at room temperature. The mixture was extracted with two times ethyl acetate and saturated NaHCO$_3$-solution/water. The organic layers were dried over sodium sulfate, filtrated and concentrated to dryness. The crude product was purified with column chromatography on silica gel using dichloromethane:methanol 100:0->90:10. The product fractions were concentrated to give 57 mg (50% yield) of a white solid. MS (m/e): 415.4 (M+H$^+$).

Example 2

N-trans-{4-[2-(4-benzo[d]isoxazol-3-yl-piperazin-1-yl)-ethyl]-cyclohexyl}-acetamide

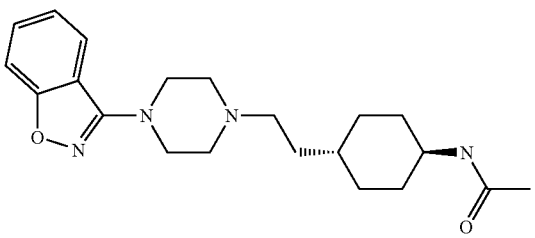

The title compound, MS: m/e=371.3 (M+H$^+$), can be prepared in accordance with the general method of example 1, step 3 from trans-4-[2-(4-benzo[d]isoxazol-3-yl-piperazin-1-yl)-ethyl]-cyclohexylamine hydrochloride (example 1, step 2) and acetic acid.

Example 3

N-trans-{4-[2-Benzo[d]isoxazol-3-yl-piperazin-1-yl)-ethyl]-cyclohexyl}-2-trans-(3-methoxy-cyclopentyl)-acetamide

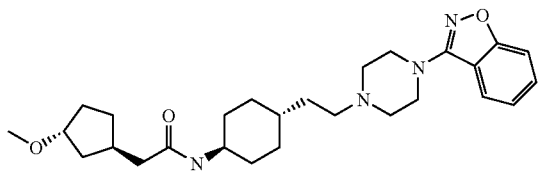

trans-(3-Methoxy-cyclopentyl)-acetic acid methyl ester (intermediate C) (71 mg, 0.41 mmol) was dissolved in 2 ml dichloromethane. Potassium trimethylsilanolate KO$^t$SiMe3 (105 mg, 0.82 mmol) was added and the suspension stirred for 16 hours at room temperature. The solvent was evaporated and trans-4-[2-(4-benzo[d]isoxazol-3-yl-piperazin-1-yl)-ethyl]-cyclohexylamine hydrochloride (example 1, step 2) (150 mg, 0.41 mmol) in 1 ml DMF was added. N,N-Diisopropylethylamine (280 μl 1.65 mmol) and 2-(1H-benzotriazol-1-yl)-1,1,3,3-tetramethyl uronium tetrafluoroborate TBTU (158 mg, 0.49 mmol) were added and the reaction stirred for 2 hours at room temperature. The reaction mixture was quenched with saturated NaHCO3-solution and extracted with dichloromethane. The organic extract was washed with brine, dried with sodium sulfate, filtered and evaporated. The crude product was purified by flash chromatography on silica gel (dichloromethane/methanol 100:0->90:10 gradient). The desired compound was obtained as a white solid (76 mg, 40%), MS: m/e=469.3 (M+H$^+$).

Example 4

N-trans-{4-[2-(4-Benzo[d]isoxazol-3-yl-piperazin-1-yl)-ethyl]-cyclohexyl}-2-hydroxy-acetamide

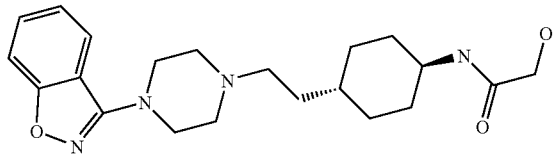

The title compound, MS: m/e=387.3 (M+H$^+$), can be prepared in accordance with the general method of example 1, step 3 from trans-4-[2-(4-benzo[d]isoxazol-3-yl-piperazin-1-yl)-ethyl]-cyclohexylamine hydrochloride (example 1, step 2) and hydroxy-acetic acid.

Example 5

N-trans-(4-{2-[4-(5-Fluoro-benzo[d]isoxazol-3-yl)-piperazin-1-yl]-ethyl}-cyclohexyl)-3-methoxy-propionamide

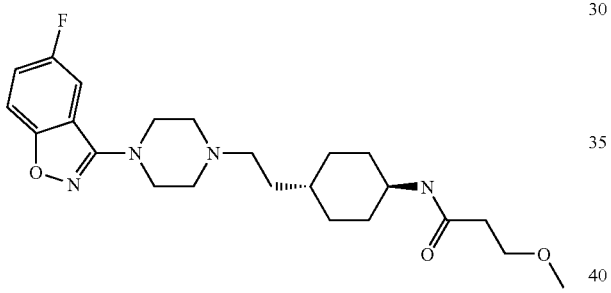

The title compound, MS: m/e=433.4 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and 3-methoxypropionic acid.

Example 6

N-trans-(4-{2-[4-(5-Fluoro-benzo[d]isoxazol-3-yl)-piperazin-1-yl]-ethyl}-cyclohexyl)-2-trans-(4-methoxy-cyclohexyl)-acetamide

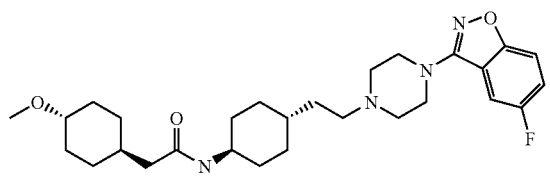

The title compound, MS: m/e=501.4 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and trans-(4-methoxy-cyclohexyl)-acetic acid methyl ester (intermediate B).

Example 7

Tetrahydro-pyran-4-carboxylic acid-trans-(4-{2-[4-(5-fluoro-benzo[d]isoxazol-3-yl)-piperazin-1-yl]-ethyl}-cyclohexyl)-amide

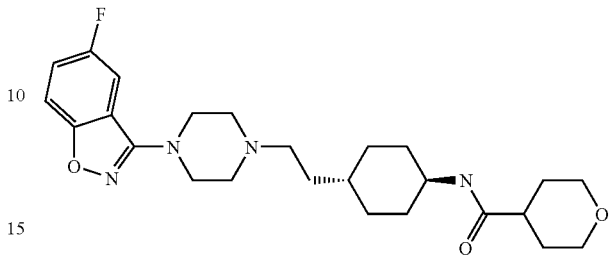

The title compound, MS: m/e=459.5 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and tetrahydro-pyran-4-carboxylic acid.

Example 8

N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide

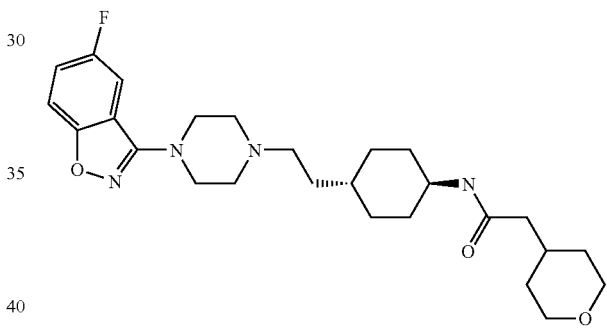

The title compound, MS: m/e=473.3 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and (tetrahydro-pyran-4-yl)-acetic acid.

Example 9

N-trans-(4-{2-[4-(5-Fluoro-benzo[d]isoxazol-3-yl)-piperazin-1-yl]-ethyl}-cyclohexyl)-2-methoxy-acetamide

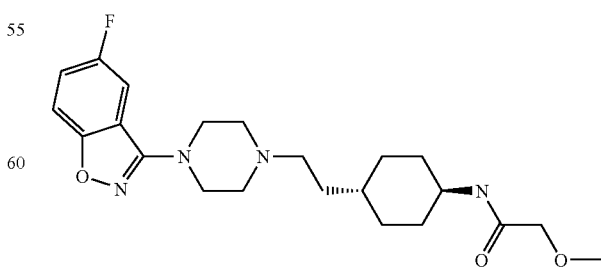

The title compound, MS: m/e=419.3 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and methoxyacetic acid.

Example 10

N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide

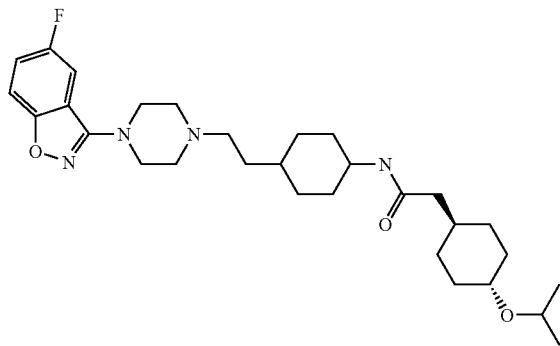

Step 1: 4-Isopropoxy-cyclohexanone

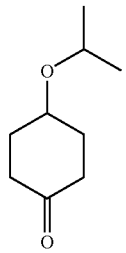

The title compound can be prepared in accordance with the literature in the patent WO 2007107566, description 42.

Step 2: (4-Isopropoxy-cyclohexylidene)-acetic acid methyl ester

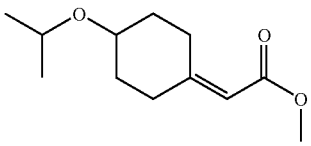

Trimethylphosphonoacetate (700 mg, 3.87 mmol) was solved in 10 ml of THF and added into a cold (0-5° C.) mixture of sodium hydride (169 mg, 3.87 mmol, 55%) in 10 ml THF. After 1 hour stirring at 0-5° C. 4-isopropoxy-cyclohexanone (550 mg, 3.5 mmol) in 5 ml THF was added drop wise. The reaction mixture was quenched after 1 hour at room temperature with saturated NaHCO$_3$-solution and extracted two times with ethyl acetate. The organic extracts were washed with brine, dried with sodium sulfate, filtered and evaporated. The crude product was purified with column chromatography on silica gel using heptane:ethyl acetate 90:10->20:80. The product fractions were concentrated to give 550 mg (74% yield) of a colorless liquid. MS (m/e): 213.3 (M+H$^+$).

Step 3: rac-(4-Isopropoxy-cyclohexyl)-acetic acid methyl ester

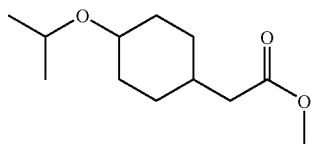

Prepared from (4-isopropoxy-cyclohexylidene)-acetic acid methyl ester (0.500 g, 2.36 mmol) by hydrogenation 16 hours at room temperature using Pd/C (10%) (50 mg) in ethylacetate (15 ml). cis/trans mixture. MS (m/e): 215.4 (M+H$^+$).

Step 4: N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide

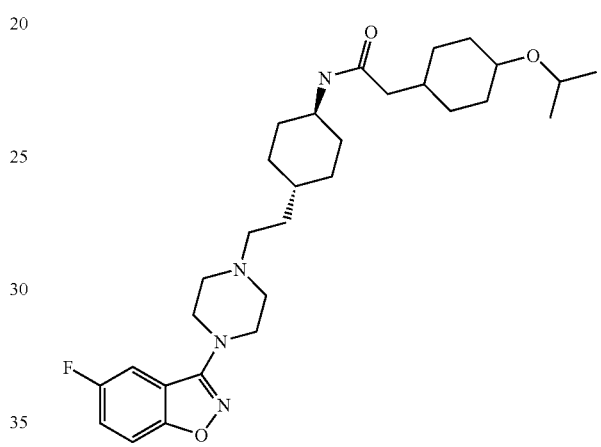

The title compound, MS: m/e=529.3 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and rac-(4-isopropoxy-cyclohexyl)-acetic acid methyl ester.

Example 11

N-trans-(4-{2-[4-(5-Fluoro-benzo[d]isoxazol-3-yl)-piperazin-1-yl]-ethyl}-cyclohexyl)-3-hydroxy-3-methyl-butyramide

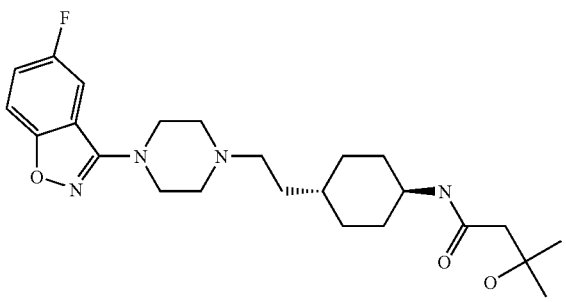

The title compound, MS: m/e=447.1 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and 3-hydroxy-3-methyl-butyric acid.

Example 12

2-Ethoxy-N-trans-(4-{2-[4-(5-fluoro-benzo[d]isoxazol-3-yl)-piperazin-1-yl]-ethyl}-cyclohexyl)-acetamide

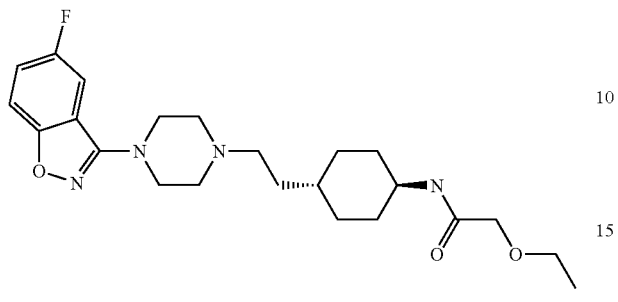

The title compound, MS: m/e=433.5 (M+H⁺), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and ethoxyacetic acid.

Example 13

4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide

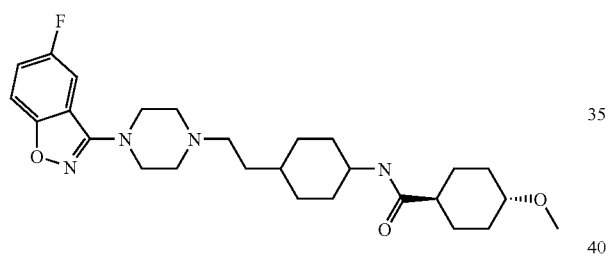

The title compound, MS: m/e=447.1 (M+H⁺, can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and 4-methoxy-cyclohexanecarboxylic acid.

Example 14

N-trans-(4-{2-[4-(5-Fluoro-benzo[d]isoxazol-3-yl)-piperazin-1-yl]-ethyl}-cyclohexyl)-methanesulfonamide

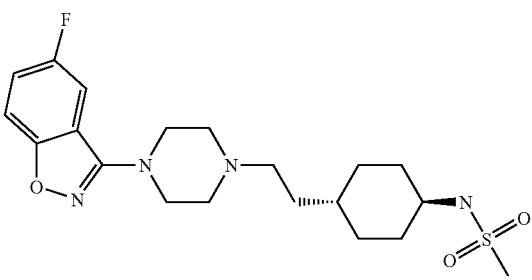

4-Trans-{2-[4-(5-Fluoro-benzo[d]isoxazol-3-yl)-piperazin-1-yl]-ethyl}-cyclohexylamine hydrochloride (intermediate D) (100 mg, 0.26 mmol) was solved in dichloromethane (2 ml), methanesulfonyl chloride (33 mg, 0.29 mmol) was added followed by triethylamine (80 µl, 0.57 mmol) and the solution was stirred overnight at room temperature. The reaction mixture was quenched with saturated NaHCO₃-solution and extracted with dichloromethane. The organic extracts were washed with brine, dried with sodium sulfate, filtered and evaporated. The crude product was purified with column chromatography on silica gel using dichloromethane/methanol 100:0->90:20. The product fractions were concentrated to give 88 mg (79% yield) of a white solid. MS (m/e): 425.2 (M+H⁺).

Example 15

2-[1,4]Dioxan-2-yl-N-trans-(4-{2-[4-(5-fluoro-benzo[d]isoxazol-3-yl)-piperazin-1-yl]-ethyl}-cyclohexyl)-acetamide

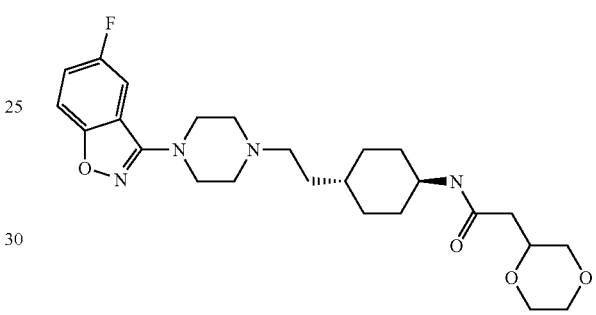

Step 1: [1,4]Dioxan-2-yl-acetic acid ethyl ester

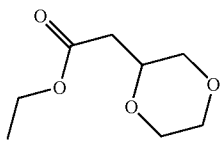

The title compound can be prepared in accordance with the literature in the patents WO 9857968 and U.S. Pat. No. 9,811,409.

Step 2: 2-[1,4]Dioxan-2-yl-N-trans-(4-{2-[4-(5-fluoro-benzo[d]isoxazol-3-yl)-piperazin-1-yl]-ethyl}-cyclohexyl)-acetamide

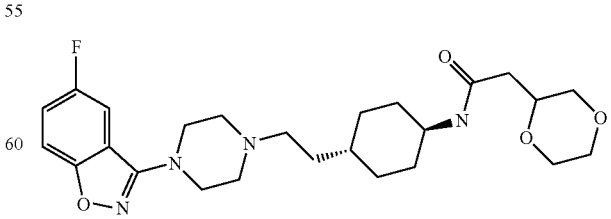

The title compound, MS: m/e=475.3 (M+H⁺), can be prepared in accordance with the general method of example 1, step 3 from 4-trans-{2-[4-(5-fluoro-benzo[d]isoxazol-3-yl)- piperazin-1-yl]-ethyl}-cyclohexylamine hydrochloride (intermediate D) and [1,4]dioxan-2-yl-acetic acid (can be prepared by LiOH hydrolysis of [1,4]dioxan-2-yl-acetic acid ethyl ester).

Example 16

3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide

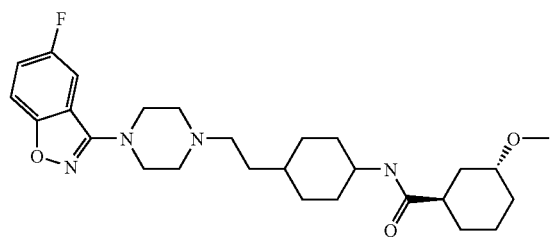

The title compound, MS: m/e=487.4 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and 3-methoxycyclohexanecarboxylic acid.

Example 17

N-trans-(4-{2-[4-(5-Fluoro-benzo[d]isoxazol-3-yl)-piperazin-1-yl]-ethyl}-cyclohexyl)-malonamide

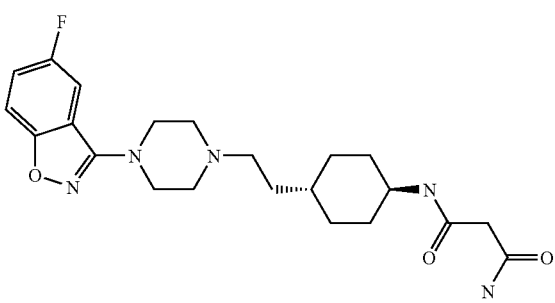

The title compound, MS: m/e=432.4 (M+H$^+$), can be prepared in accordance with the general method of example 1, step 3 from 4-trans-{2-[4-(5-fluoro-benzo[d]isoxazol-3-yl)-piperazin-1-yl]-ethyl}-cyclohexylamine hydrochloride (intermediate D) and malonamic acid (can be prepared by LiOH hydrolysis of the commercially available malonamic acid ethyl ester).

Example 18 rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide

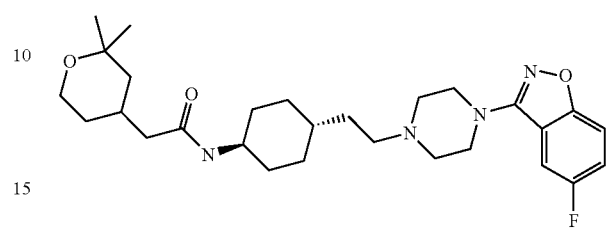

The title compound, MS: m/e=501.4 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and (2,2-dimethyl-tetrahydro-pyran-4-yl)-acetic acid methyl ester.

Example 19

N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide

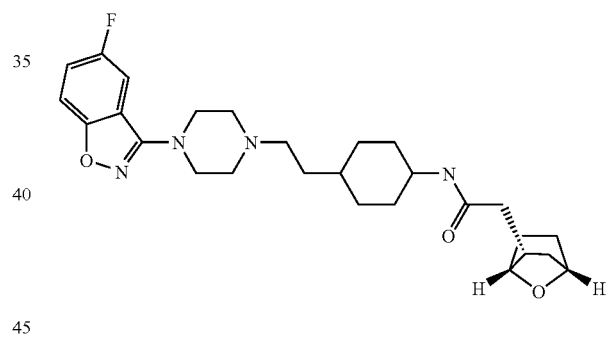

Step 1: 7-Oxa-bicyclo[2.2.1]hept-5-en-2-one

The title compound can be prepared in accordance with literature *Lit.: Helvetica Chimica ACTA*-Vol. 66, Fasc. 6(1983-Nr. 182), S1865-1871.

Step 2: (1S,4R)-[7-Oxa-bicyclo[2.2.1]hept-(2E)-ylidene]-acetic acid methyl ester The title compound, MS: m/e=169.0 (M+H$^+$), can be prepared in accordance with the general method of example 10, step 2 from 7-oxa-bicyclo[2.2.1]hept-5-en-2-one.

Step 3: (1S,4R)-(7-Oxa-bicyclo[2.2.1]hept-2-yl)-acetic acid methyl ester

The title compound, MS: m/e=171.2 (M+H$^+$), can be prepared in accordance with the general method of example 10, step 3 from (1S,4R)-[7-oxa-bicyclo[2.2.1]hept-(2E)-ylidene]-acetic acid methyl ester.

Step 4: N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide The title compound, MS: m/e=485.4 (M+H⁺), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and (1S,4R)-(7-oxa-bicyclo[2.2.1]hept-2-yl)-acetic acid methyl ester.

Example 20

N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide

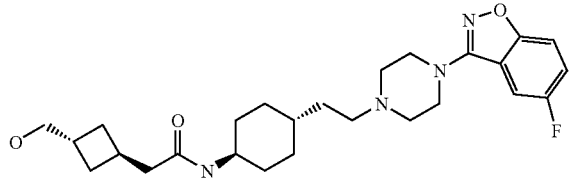

The title compound, MS: m/e=473.4 (M+H⁺), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and trans-(3-hydroxymethyl-cyclobutyl)-acetic acid methyl ester (intermediate E, step 5).

Example 21

N-trans-(4-{2-[4-(5-Fluoro-benzo[d]isoxazol-3-yl)-piperazin-1-yl]-ethyl}-cyclohexyl)-2-(3-methyl-oxetan-3-yl)-acetamide

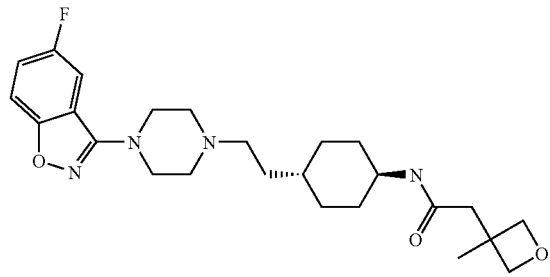

Step 1: Oxetan-3-ylidene-acetic acid methyl ester

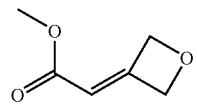

Oxetan-3-one (commercially available) (50 mg, 0.69 mmol) was solved in 1 ml dichloromethane and cooled to 0-5° C. (Methoxycarbonylmethylene) triphenylphosphorane (255 mg, 0.76 mmol) was added and the mixture stirred for 15 minutes. The mixture was directly purified with column chromatography on silica gel using heptane:ethyl acetate 100:0->0:100. The product fractions were concentrated to give 57 mg (64% yield) of a white solid.

Step 2: (3-Methyl-oxetan-3-yl)-acetic acid methyl ester

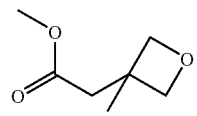

Chlorotrimethylsilane (74 µl, 0.58 mmol) was solved in 1.5 ml THF. Copper(I) iodide (7 mg, 0.04 mmol) and oxetan-3-ylidene-acetic acid methyl ester (50 mg, 0.39 mmol) in 0.5 ml THF were added at room temperature and the mixture was stirred for 15 minutes at room temperature. The reaction mixture was cooled to −15° C. and 3N methylmagnesium-chloride-solution (0.52 ml, 1.56 mmol) was added drop wise. The reaction mixture was stirred for 1 hour at room temperature, quenched then with saturated NH₄Cl-solution and extracted with dichloromethane. The organic extracts were washed with brine, dried with sodium sulfate, filtered and evaporated to give 65 mg (92%) light yellow oil. The crude product was used for the next step without further purification.

Step 3: N-trans-(4-{2-[4-(5-Fluoro-benzo[d]isoxazol-3-yl)-piperazin-1-yl]-ethyl}-cyclohexyl)-2-(3-methyl-oxetan-3-yl)-acetamide

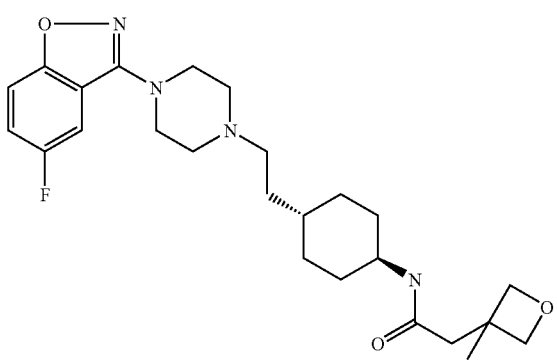

The title compound, MS: m/e=459.4 (M+H⁺), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and (3-methyl-oxetan-3-yl)-acetic acid methyl ester.

Example 22

2-((S)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide

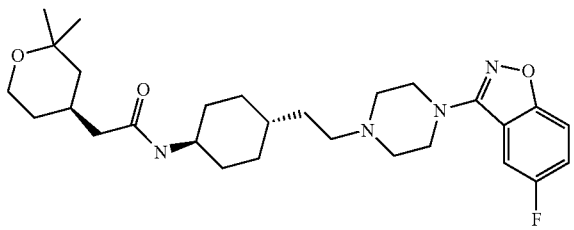

The title compound, MS: m/e=501.3 (M+H⁺), was obtained from separation of rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide (example 18) using a chiral column (chiralpak AD).

Example 23

2-((R)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide

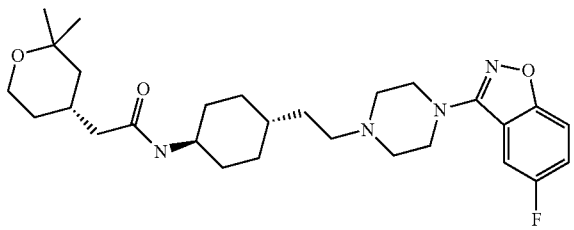

The title compound, MS: m/e=501.3 (M+H⁺), was obtained from separation of rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide (example 18) using a chiral column (chiralpak AD).

Example 24

2-[1,3]-Dioxan-2-yl-N-trans-(4-{2-[4-(5-fluoro-benzo[d]isoxazol-3-yl)-piperazin-1-yl]-ethyl}-cyclohexyl)-acetamide

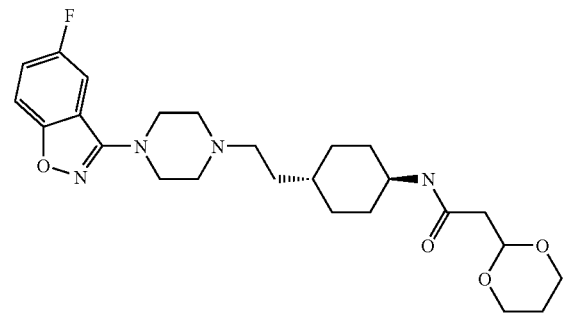

Step 1: [1,3]Dioxan-2-yl-acetic acid methyl ester

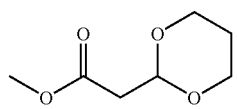

Propane-1,3-diol (2.45 ml, 36 mmol) was dissolved in 100 ml THF and cooled to 0-5° C. Sodium hydride (1.43 g, 40 mmol, 55%) was added and the reaction mixture stirred for 15 minutes at 0-5° C. Propyonic acid methyl ester (2.97 ml, 36 mmol) dissolved in 10 ml THF was added drop wise and stirred for 3 hours at 0-5° C. The reaction mixture was quenched with 2N HCl-solution and extracted two times with ethyl acetate. The organic extracts were washed with brine, dried with sodium sulfate, filtered and evaporated. The crude product was purified by flash chromatography on silica gel (dichloromethane). The desired compound was obtained as a colourless liquid (2.96 g, 52%).

Step 2: 2-[1,3]Dioxan-2-yl-N-trans-(4-{2-[4-(5-fluoro-benzo[d]isoxazol-3-yl)-piperazin-1-yl]-ethyl}-cyclohexyl)-acetamide

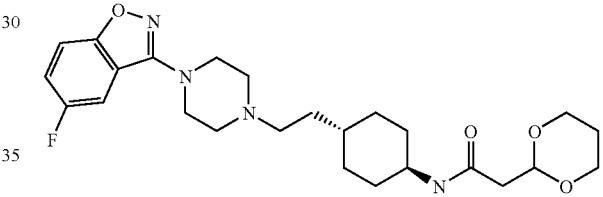

The title compound, MS: m/e=475.3 (M+H⁺), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and [1,3]dioxan-2-yl-acetic acid methyl ester.

Example 25

N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide

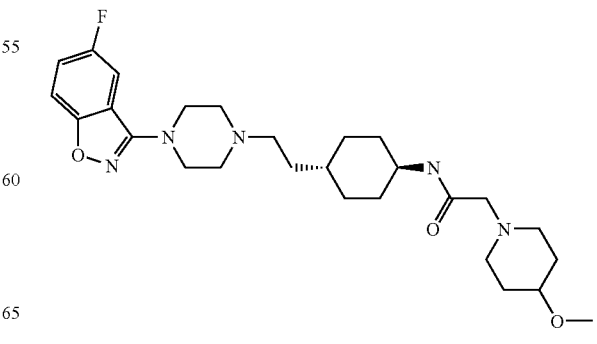

Step 1: (4-Hydroxy-piperidin-1-yl)-acetic acid methyl ester

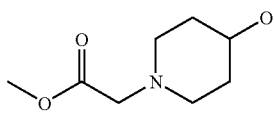

The title compound can be prepared in accordance with the literature in the patent WO2007127726, preparation 34.

Step 2: (4-Methoxy-piperidin-1-yl)-acetic acid methyl ester

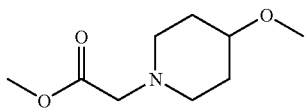

The title compound can be prepared in accordance with the general method of intermediate B, step 3 from (4-hydroxy-piperidin-1-yl)-acetic acid methyl ester.

Step 2: N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide

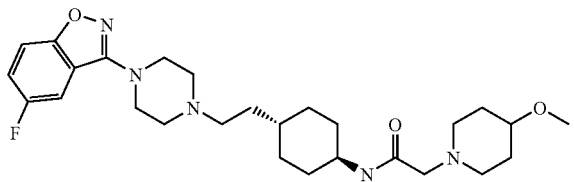

The title compound, MS: m/e=502.4 (M+H$^+$), can be prepared in accordance with the general method of example 3 from 4-trans-{2-[4-(5-fluoro-benzo[d]isoxazol-3-yl)-piperazin-1-yl]ethyl}-cyclohexylamine hydrochloride (intermediate D) and (4-methoxy-piperidin-1-yl)-acetic acid methyl ester.

Example 26

N-trans-(4-{2-[4-(5-Fluoro-benzo[d]isoxazol-3-yl)-piperazin-1-yl]-ethyl}-cyclohexyl)-3,3-dimethoxy-propionamide

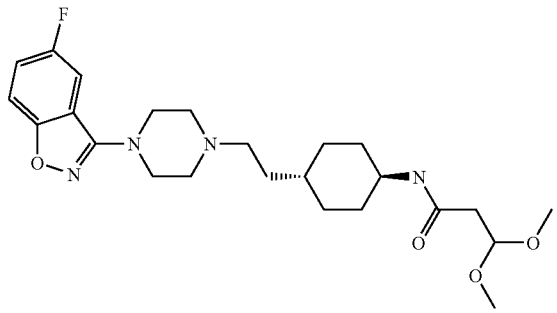

The title compound, MS: m/e=463.3 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and methyl 3,3-dimethoxypropionate.

Example 27

N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide

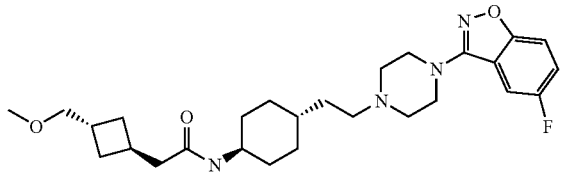

The title compound, MS: m/e=487.5 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and trans-(3-methoxymethyl-cyclobutyl)-acetic acid methyl ester (intermediate E).

Example 28

N-trans-(4-{2-[4-(5-Fluoro-benzo[d]isoxazol-3-yl)-piperazin-1-yl]-ethyl}-cyclohexyl)-4,4-dimethoxy-butyramide

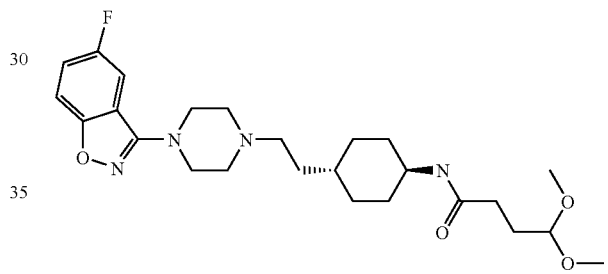

The title compound, MS: m/e=477.3 (M+H$^+$), can be prepared in accordance with the general method of example 3 from 4-trans-{2-[4-(5-fluoro-benzo[d]isoxazol-3-yl)-piperazin-1-yl]-ethyl}-cyclohexylamine hydrochloride (intermediate D) and methyl 4,4-dimethoxybutyrate.

Example 29

N-trans-(4-{2-[4-(6-Chloro-benzo[d]isoxazol-3-yl)-piperazin-1-yl]-ethyl}-cyclohexyl)-3-methoxy-propionamide

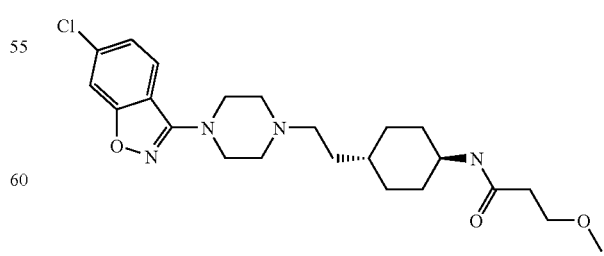

The title compound, MS: m/e=449.3/451.1 (M+H$^+$), can be prepared in accordance with the general method of example 1, step 3 from 4-trans-{2-[4-(6-chloro-benzo[d]

isoxazol-3-yl)-piperazin-1-yl]-ethyl}-cyclohexylamine hydrochloride (intermediate F) and 3-methoxypropionic acid.

Example 30

N-trans-(4-{2-[4-(6-Chloro-benzo[d]isoxazol-3-yl)-piperazin-1-yl]-ethyl}-cyclohexyl)-acetamide

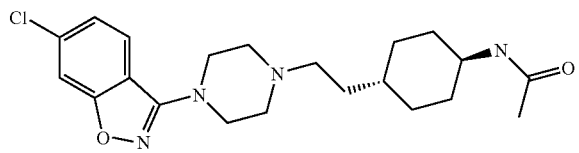

The title compound, MS: m/e=405.4 (M+H⁺), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and acetic acid.

Example 31

N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide

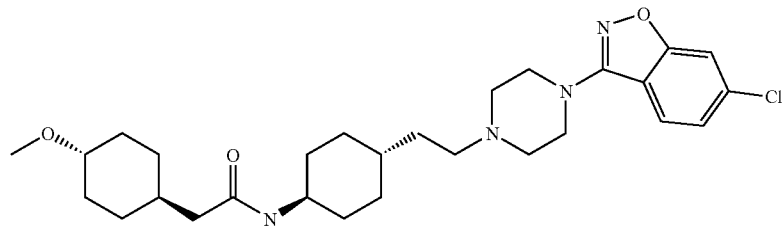

The title compound, MS: m/e=516.9 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and trans-(4-methoxy-cyclohexyl)-acetic acid methyl ester (intermediate B).

Example 32

Tetrahydro-pyran-4-carboxylic acid-trans-(4-{2-[4-(6-chloro-benzo[d]isoxazol-3-yl)-piperazin-1-yl]-ethyl}-cyclohexyl)-amide

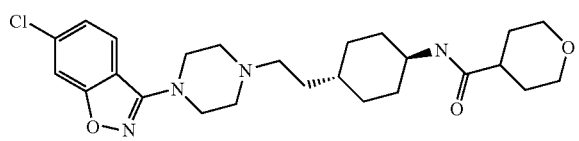

The title compound, MS: m/e=475.3 (M+H⁺), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and tetrahydro-pyran-4-carboxylic acid.

Example 33 rac-N-trans-(4-{2-[4-(6-Chloro-benzo[d]isoxazol-3-yl)-piperazin-1-yl]-ethyl}-cyclohexyl)-3,3,3-trifluoro-2-hydroxy-propionamide

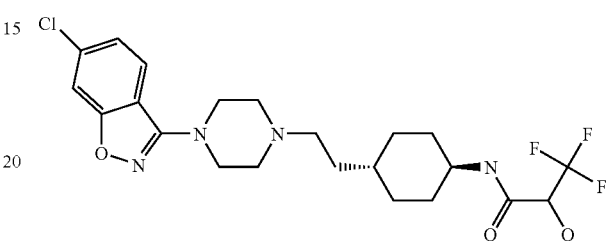

The title compound, MS: m/e=489.4 (M+H⁺), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and rac-3,3,3-trifluoro-2-hydroxy-propionic acid.

Example 34

Tetrahydro-furan-3-carboxylic acid N-trans-(4-{2-[4-(6-chloro-benzo[d]isoxazol-3-yl)-piperazin-1-yl]-ethyl}-cyclohexyl)-amide

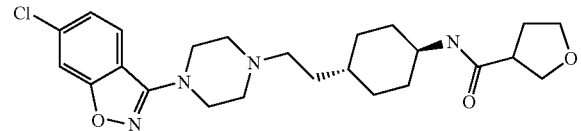

The title compound, MS: m/e=461.3 (M+H⁺), can be prepared in accordance with the general method of example 1, step 3 from 4-trans-{2-[4-(6-chloro-benzo[d]isoxazol-3-yl)- piperazin-1-yl]-ethyl}-cyclohexylamine hydrochloride (intermediate F) and tetrahydro-furan-3-carboxylic acid.

Example 35

N-trans-(4-{2-[4-(6-Chloro-benzo[d]isoxazol-3-yl)-piperazin-1-yl]-ethyl}-cyclohexyl)-2-(tetrahydro-pyran-2-yl)-acetamide

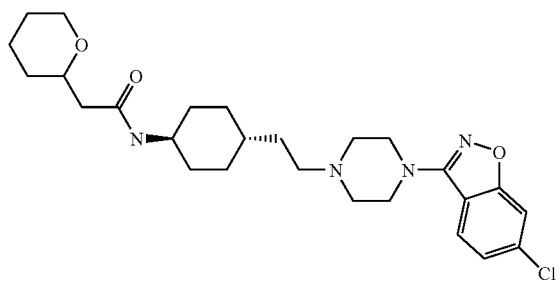

The title compound, MS: m/e=489.4 (M+H⁺), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and (tetrahydro-pyran-2-yl)-acetic acid.

Example 36

N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide

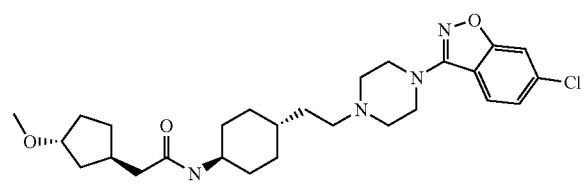

The title compound, MS: m/e=503.4 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and trans-(3-methoxy-cyclopentyl)-acetic acid methyl ester (intermediate C).

Example 37

N-trans-(4-{2-[4-(6-Chloro-benzo[d]isoxazol-3-yl)-piperazin-1-yl]-ethyl}-cyclohexyl)-3-methoxy-butyramide

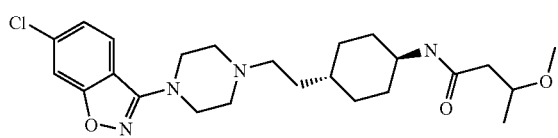

Step 1: 3-Methoxy-butyric acid methyl ester

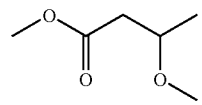

The title compound can be prepared in accordance with the preparation described in the literature *Journal of Organic Chemistry* (1995), 60(11), 3529-32.

Step 2: N-trans (4-{2-[4-(6-Chloro-benzo[d]isoxazol-3-yl)-piperazin-1-yl]-ethyl}-cyclohexyl)-3-methoxy-butyramide

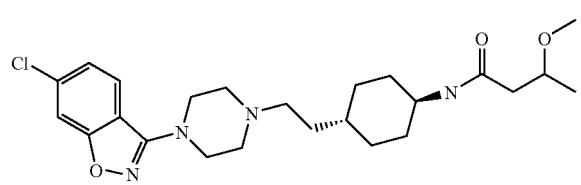

The title compound, MS: m/e=463.3 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and 3-methoxy-butyric acid methyl ester.

Example 38

1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide

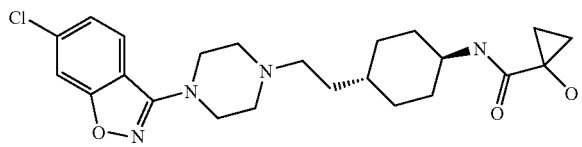

The title compound, MS: m/e=447.1 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and 1-hydroxy-cyclopropanecarboxylic acid.

Example 39

N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide

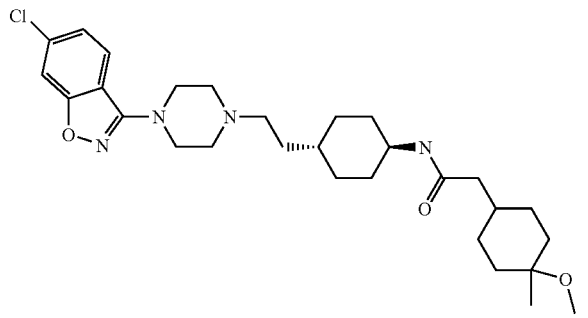

Step 1: (4-Methoxy-4-methyl-cyclohexyl)-acetic acid methyl ester

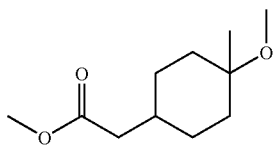

The title compound, MS: m/e=201.2 (M+H$^+$), can be prepared in accordance with the general method of example 10, step 1 and step 2 from 4-methoxy-4-methyl-cyclohexanone (described in literatures).

Step 2: N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide

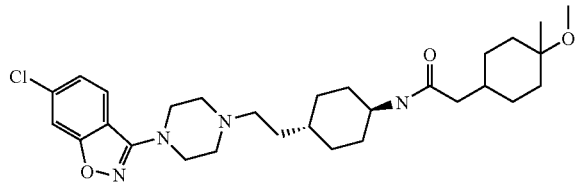

The title compound, MS: m/e=531.3 (M+H$^+$), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and (4-methoxy-4-methyl-cyclohexyl)-acetic acid methyl ester.

Example 40

N-trans-(4-{2-[4(6-Chloro-benzo[d]isoxazol-3-yl)-piperazin-1-yl]-ethyl}-cyclohexyl)-2-(tetrahydro-pyran-4-yl)-acetamide

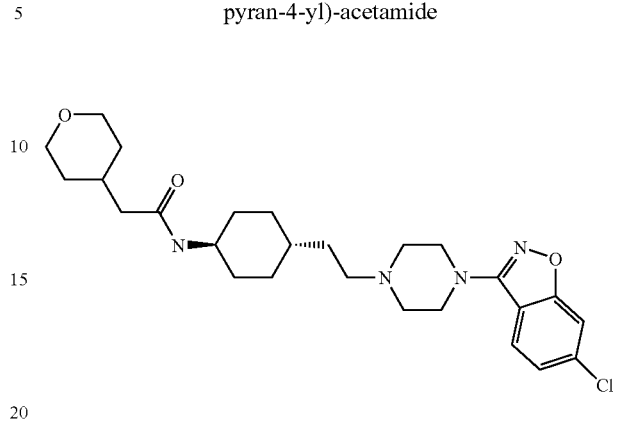

The title compound, MS: m/e=489.4 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and (tetrahydro-pyran-4-yl)-acetic acid.

Example 41

N-trans-(4-{2-[4-(6-Chloro-benzo[d]isoxazol-3-yl)-piperazin-1-yl]-ethyl}-cyclohexyl)-propionamide

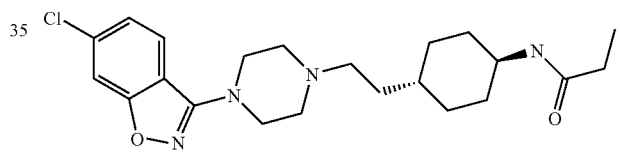

The title compound, MS: m/e=419.4 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and propionic acid.

Example 42

N-trans-(4-{2-[4-(6-Chloro-benzo[d]isoxazol-3-yl)-piperazin-1-yl]-ethyl}-cyclohexyl)-2-hydroxy-acetamide

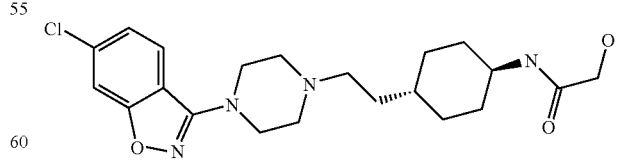

The title compound, MS: m/e=421.3 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and hydroxy-acetic acid.

Example 43

N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide

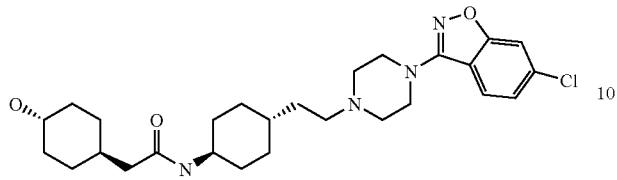

The title compound, MS: m/e=503.4 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and trans-(4-hydroxy-cyclohexyl)-acetic acid (intermediate B, step 1).

Example 44

N-trans-(4-{2-[4-(6-Chloro-benzo[d]isoxazol-3-yl)-piperazin-1-yl]-ethyl}-cyclohexyl)-3-hydroxy-3-methyl-butyramide

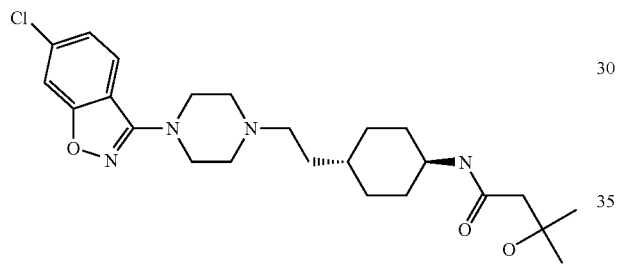

The title compound, MS: m/e=463.3 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and 3-hydroxy-3-methyl-butyric acid.

Example 45

(S)—N-trans-(4-{2-[4-(6-Chloro-benzo[d]isoxazol-3-yl)-piperazin-1-yl]-ethyl}-cyclohexyl)-3-hydroxy-butyramide

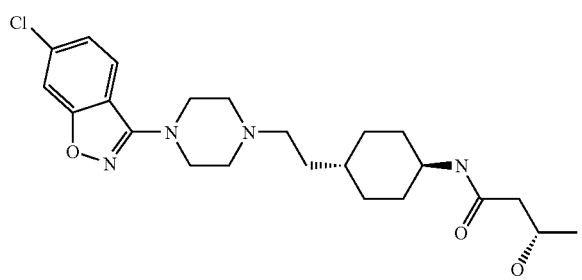

The title compound, MS: m/e=449.1 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and (S)-(+)-3-hydroxylbutyric acid.

Example 46

(S)-Tetrahydro-furan-3-carboxylic acid-N-trans-(4-{2-[4-(6-chloro-benzo[d]isoxazol-3-yl)-piperazin-1-yl]-ethyl}-cyclohexyl)-amide

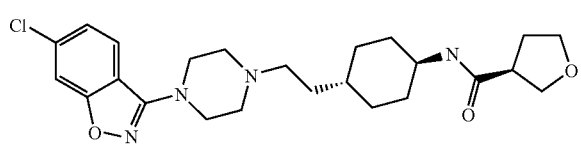

The title compound, MS: m/e=461.4 (M+H$^+$), was obtained from separation of tetrahydro-furan-3-carboxylic acid N-trans-(4-{2-[4-(6-chloro-benzo[d]isoxazol-3-yl)-piperazin-1-yl]-ethyl}-cyclohexyl)-amide (example 34) using a chiral column (chiralpak AD).

Example 47

N-trans-(4-{2-[4-(6-Chloro-benzo[d]isoxazol-3-yl)-piperazin-1-yl]-ethyl}-cyclohexyl)-2-oxetan-3-yl-acetamide

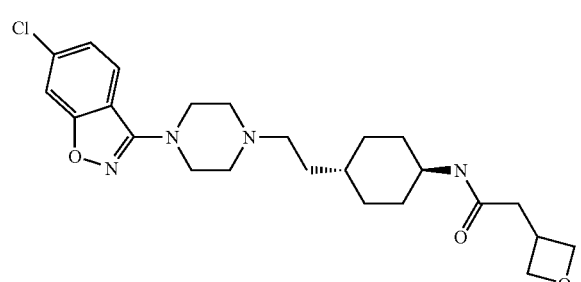

Step 1: Oxetan-3-ylidene-acetic acid methyl ester

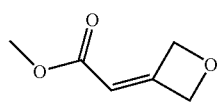

Oxetan-3-one (commercially available) (50 mg, 0.69 mmol) was solved in 1 ml dichloromethane and cooled to 0-5° C. (Methoxycarbonylmethylene) triphenylphosphorane (255 mg, 0.76 mmol) was added and the mixture stirred for 15 minutes. The mixture was directly purified with column chromatography on silica gel using heptane:ethyl acetate 100:0->0:100. The product fractions were concentrated to give 57 mg (64% yield) of a white solid.

Step 2: Oxetan-3-yl-acetic acid methyl ester

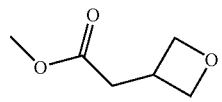

The title compound can be prepared in accordance with the general method of example 10, step 2 from oxetan-3-ylidene-acetic acid methyl ester.

Step 3: N-trans-(4-{2-[4-(6-Chloro-benzo[d]isoxazol-3-yl)-piperazin-1-yl]-ethyl}-cyclohexyl)-2-oxetan-3-yl-acetamide

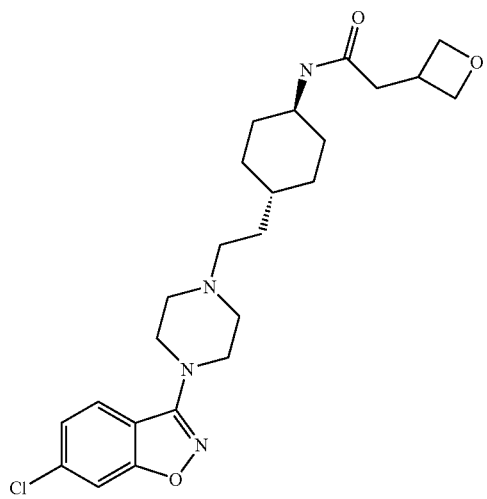

The title compound, MS: m/e=461.1 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and oxetan-3-yl-acetic acid methyl ester.

Example 48

N-trans-(4-{2-[4-(6-Chloro-benzo[d]isoxazol-3-yl)-piperazin-1-yl]-ethyl}-cyclohexyl)-2-trans-(3-methoxymethyl-cyclobutyl)-acetamide

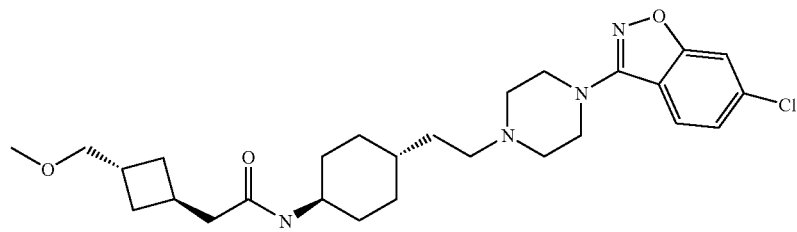

The title compound, MS: m/e=503.0 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and trans-(3-methoxymethyl-cyclobutyl)-acetic acid methyl ester (intermediate E).

Example 49

N-trans-(4-{2-[4-(6-Chloro-benzo[d]isoxazol-3-yl)-piperazin-1-yl]-ethyl}-cyclohexyl)-2-(R)-tetrahydro-pyran-2-yl-acetamide

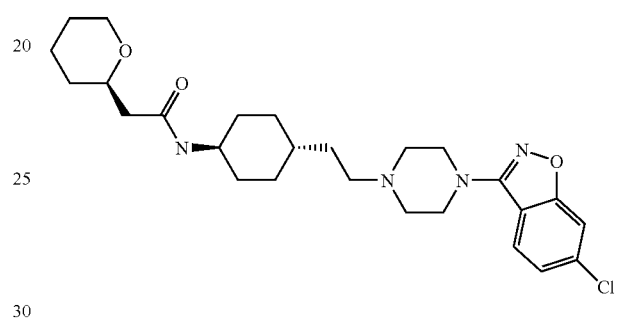

Step 1: N-trans (4-{2-[4-(6-Chloro-benzo[d]isoxazol-3-yl)-piperazin-1-yl]-ethyl}-cyclohexyl)-2-tetrahydro-pyran-2-yl-acetamide The title compound, MS: m/e=489.4 (M+H⁺), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and 2-(tetrahydro-pyran-2-yl)-acetic acid.

Step 2: N-trans (4-{2-[4-(6 Chloro-benzo[d]isoxazol-3-yl)-piperazin-1-yl]-ethyl}-cyclohexyl)-2-(R)-tetrahydro-pyran-2-yl-acetamide The title compound, MS: m/e=489.4 (M+H⁺), was obtained from separation of N-trans-(4-{2-[4-(6-chloro-benzo[d]isoxazol-3-yl)-piperazin-1-yl]-ethyl}-cyclohexyl)-2-tetrahydro-pyran-2-yl-acetamide (example 49, step 1) using a chiral column (chiralpak AD).

Example 50

N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide

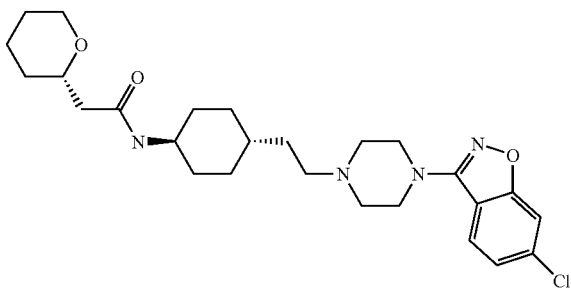

The title compound, MS: m/e=489.4 (M+H$^+$), was obtained from separation of N-trans-(4-{2-[4-(6-chloro-benzo[d]isoxazol-3-yl)-piperazin-1-yl]-ethyl}-cyclohexyl)-2-tetrahydro-pyran-2-yl-acetamide (example 49, step 1) using a chiral column (chiralpak AD).

Example 51

N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide

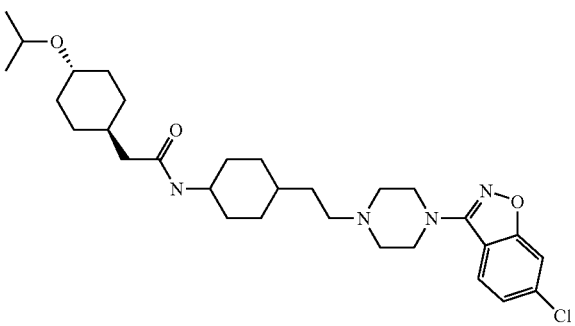

The title compound, MS: m/e=545.4 (M+H$^+$), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and rac-(4-isopropoxy-cyclohexyl)-acetic acid methyl ester (example 10, step 3).

Example 52

N-trans-(4-{2-[4-(6-Chloro-benzo[d]isoxazol-3-yl)-piperazin-1-yl]-ethyl}-cyclohexyl)-2-cyclopropyl-acetamide

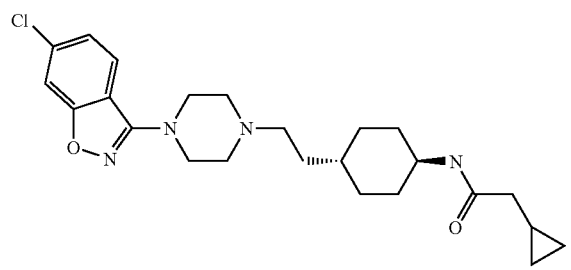

The title compound, MS: m/e=445.3 (M+H$^+$, can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and cyclopropyl-acetic acid.

Example 53

N-trans-(4-{2-[4-(6-Chloro-benzo[d]isoxazol-3-yl)-piperazin-1-yl]-ethyl}-cyclohexyl)-3,3,3-trifluoro-propionamide

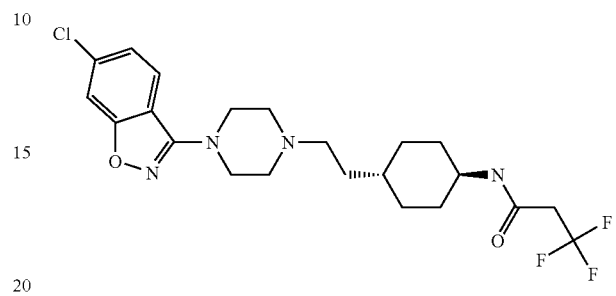

The title compound, MS: m/e=473.2 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and 3,3,3-trifluoro-propionic acid.

Example 54

4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide

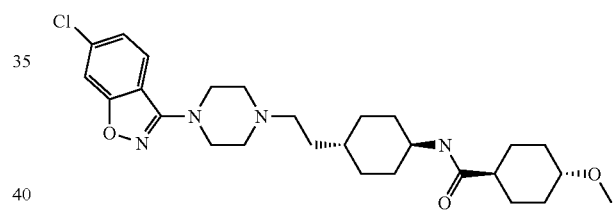

The title compound, MS: m/e=503.3/505.2 (M+H$^+$), can be prepared in accordance with the general method of example 1, step 3 from 4-trans-{2-[4-(6-chloro-benzo[d]isoxazol-3-yl)-piperazin-1-yl]-ethyl}-cyclohexylamine hydrochloride (intermediate F) and 4-methoxycyclohexanecarboxylic acid and by separation of the two stereoisomers using a chiral column (chiralpak AD).

Example 55

N-trans-(4-{2-[4-(6-Chloro-benzo[d]isoxazol-3-yl)-piperazin-1-yl]-ethyl}-cyclohexyl)-3,3-dimethoxy-propionamide

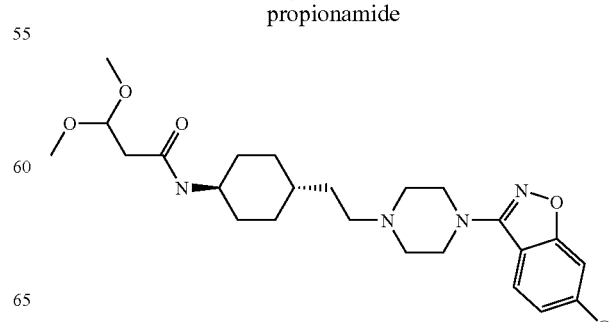

The title compound, MS: in/e=479.2 (M+H⁺), can be prepared in accordance with the general method of example 3 from 4-trans-{2-[4-(6-chloro-benzo[d]isoxazol-3-yl)-piperazin-1-yl]-ethyl}-cyclohexylamine hydrochloride (intermediate F) and methyl 3,3-dimethoxypropionate.

Example 56

N-trans-(4-{2-[4-(5,6-Difluoro-benzo[d]isoxazol-3-yl)-piperazin-1-yl]-ethyl}-cyclohexyl)-acetamide

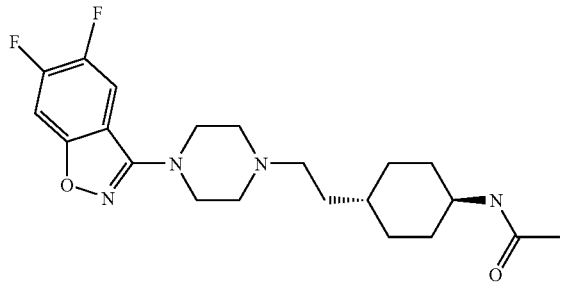

The title compound, MS: m/e=407.3 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and acetic acid.

Example 57

N-trans-(4-{2-[4-(5,6-Difluoro-benzo[d]isoxazol-3-yl)-piperazin-1-yl]-ethyl}-cyclohexyl)-3-methoxy-propionamide

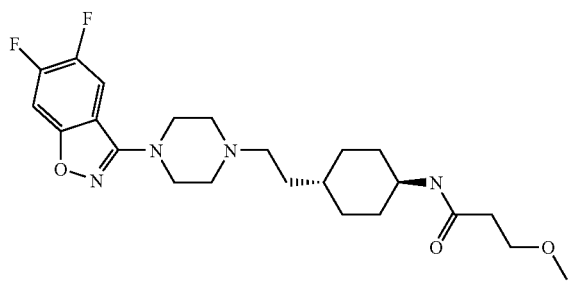

The title compound, MS: m/e=451.2 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and 3-methoxypropionic acid.

Example 58

N-trans-(4-{2-[4-(5,6-Difluoro-benzo[d]isoxazol-3-yl)-piperazin-1-yl]-ethyl}-cyclohexyl)-2-trans-(4-methoxy-cyclohexyl)-acetamide The title compound, MS: m/e=519.4 (M+H⁺), can be prepared in accordance with the general method of example 3 from 4-trans-{2-[4-(5,6-difluoro-benzo[d]isoxazol-3-yl)-piperazin-1-yl]-ethyl}-cyclohexylamine hydrochloride (intermediate G) and trans-(4-methoxy-cyclohexyl)-acetic acid methyl ester (intermediate B).

Example 59

N-trans-(4-{2-[4-(5,6-Difluoro-benzo[d]isoxazol-3-yl)-piperazin-1-yl]-ethyl}-cyclohexyl)-propionamide

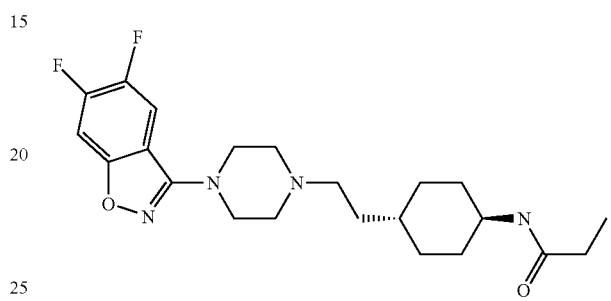

The title compound, MS: m/e=421.2 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and propionic acid.

Example 60

N-trans-(4-{2-[4-(5,6-Difluoro-benzo[d]isoxazol-3-yl)-piperazin-1-yl]-ethyl}-cyclohexyl)-2-methoxy-acetamide

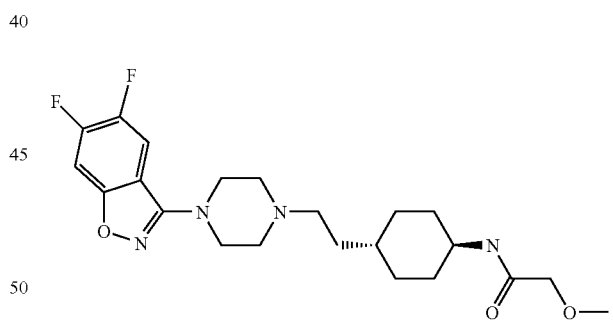

The title compound, MS: m/e=437.2 (M+H⁺), can be prepared in accordance with the general method of example 1, step 3 from 4-trans-{2-[4-(5,6-difluoro-benzo[d]isoxazol-3-

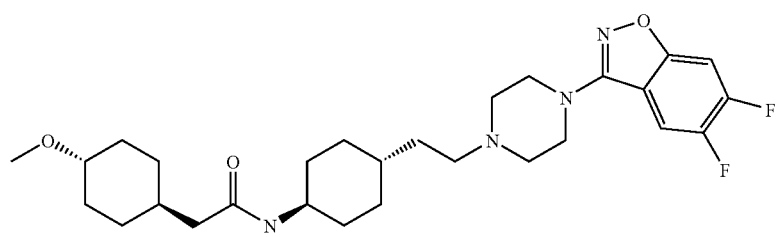

Example 61

N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide

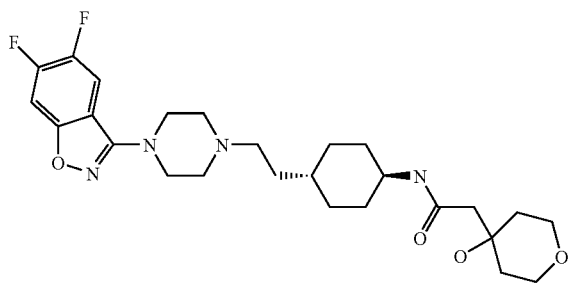

The title compound, MS: m/e=507.3 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and (4-hydroxy-tetrahydro-pyran-4-yl)-acetic acid (can be prepared in accordance with the patent WO2007006534).

Example 62

N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide

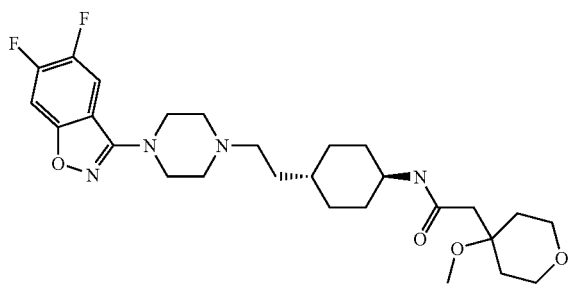

The title compound, MS: m/e=521.4 (M+H⁺), can be prepared in accordance with the general method of example 3 from 4-trans-{2-[4-(5,6-difluoro-benzo[d]isoxazol-3-yl)-piperazin-1-yl]-ethyl}-cyclohexylamine hydrochloride (intermediate G) and (4-methoxy-tetrahydro-pyran-4-yl)-acetic acid methyl ester (can be prepared in accordance with the general method of intermediate B, step 2 and step 3 from (4-hydroxy-tetrahydro-pyran-4-yl)-acetic acid (WO2007006534).

Example 63

N-trans-(4-{2-[4-(5,6-Difluoro-benzo[d]isoxazol-3-yl)-piperazin-1-yl]-ethyl}-cyclohexyl)-2-(tetrahydro-pyran-4-yl)-acetamide

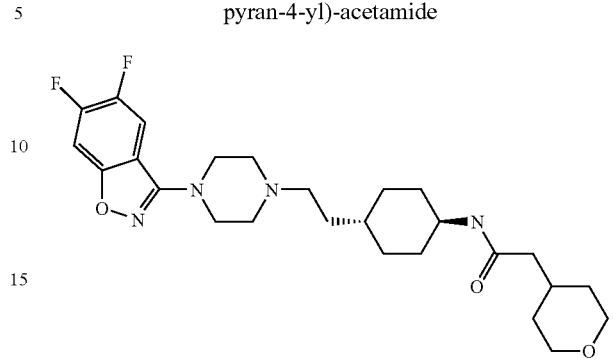

The title compound, MS: m/e=491.2 (M+H⁺), can be prepared in accordance with the general method of example 1, step 3 from 4-trans-{2-[4-(5,6-difluoro-benzo[d]isoxazol-3-yl)-piperazin-1-yl]ethyl}-cyclohexylamine hydrochloride (intermediate G) and tetrahydropyran-4-yl-acetic acid.

Example 64

N-trans-(4-{2-[4-(5,6-Difluoro-benzo[d]isoxazol-3-yl)-piperazin-1-yl]-ethyl}-cyclohexyl)-3-hydroxy-3-methyl-butyramide

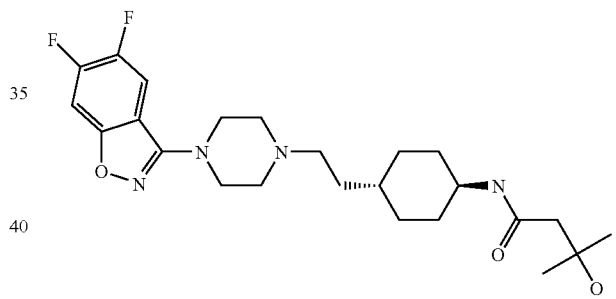

The title compound, MS: m/e=465.3 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and beta-hyroxyisovaleric acid.

Example 65

N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide

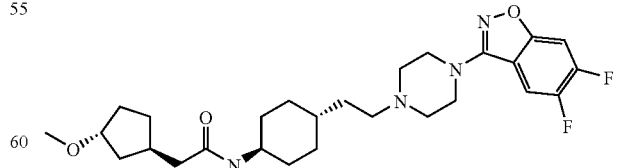

The title compound, MS: m/e=505.3 (M+H⁺), can be prepared in accordance with the general method of example 3 from 4-trans-{2-[4-(5,6-difluoro-benzo[d]isoxazol-3-yl)-piperazin-1-yl]-ethyl}-cyclohexylamine hydrochloride (intermediate G) and trans-(3-methoxy-cyclopentyl)-acetic acid methyl ester (intermediate C).

Example 66

4-Methoxy-cyclohexanecarboxylic acid N-trans-(4-{2-[4-(5,6-difluoro-benzo[d]isoxazol-3-yl)-piperazin-1-yl]-ethyl}-cyclohexyl)-amide

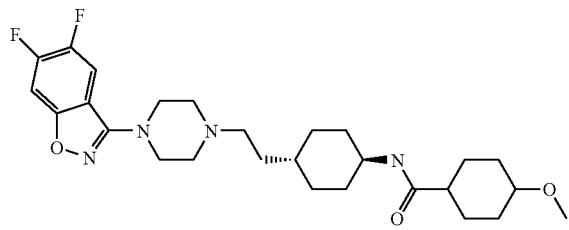

The title compound, MS: m/e=505.3 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and 4-methoxy-cyclohexanecarboxylic acid.

Example 67

Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide

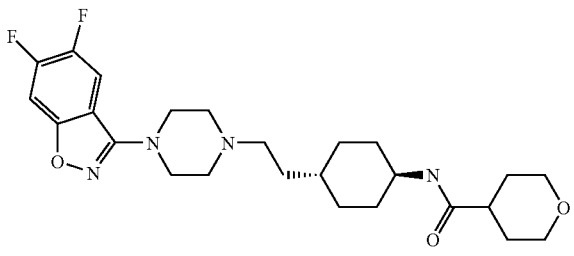

The title compound, MS: m/e=477.2 (M+H⁺), can be prepared in accordance with the general method of example 1, step 3 from 4-trans-{2-[4-(5,6-difluoro-benzo[d]isoxazol-3-yl)-piperazin-1-yl]-ethyl}-cyclohexylamine hydrochloride (intermediate G) and tetrahydro-pyran-4-carboxylic acid.

Example 68

Ethanesulfonic acid N-trans-(4-{2-[4-(5,6-difluoro-benzo[d]isoxazol-3-yl)-piperazin-1-yl]-ethyl}-cyclohexyl)-amide

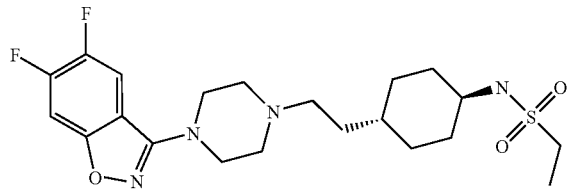

The title compound, MS: m/e=457.4 (M+H⁺), can be prepared in accordance with the general method of example 14 from 4-trans-{2-[4-(5,6-difluoro-benzo[d]isoxazol-3-yl)-piperazin-1-yl]-ethyl}-cyclohexylamine hydrochloride (intermediate G) and ethanesulfonyl chloride.

Example 69

N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide

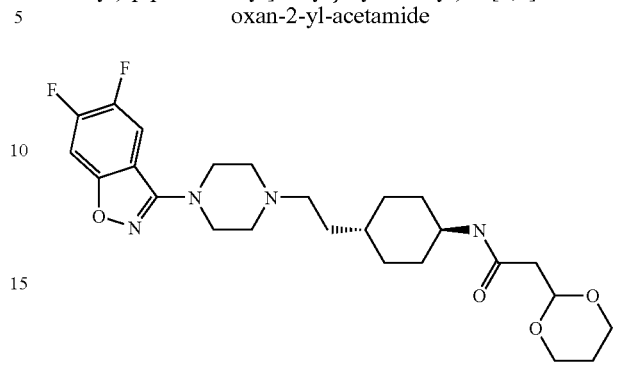

The title compound, MS: m/e=493.3 (M+H⁺), can be prepared in accordance with the general method of example 3 from 4-trans-{2-[4-(5,6-difluoro-benzo[d]isoxazol-3-yl)-piperazin-1-yl]-ethyl}-cyclohexylamine hydrochloride (intermediate G) and [1,3]dioxan-2-yl-acetic acid methyl ester (example 24, step 1).

Example 70

N-trans-(4-{2-[4-(6-Chloro-5-fluoro-benzo[d]isoxazol-3-yl)-piperazin-1-yl]-ethyl}-cyclohexyl)-propionamide

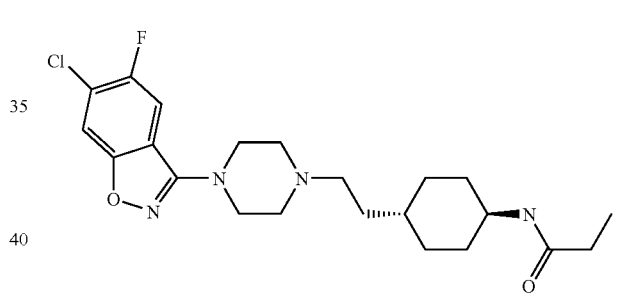

The title compound, MS: m/e=437.2 (M+H⁺), can be prepared in accordance with the general method of example 1, step 3 from 4-trans-{2-[4-(6-chloro-5-fluoro-benzo[d]isoxazol-3-yl)-piperazin-1-yl]-ethyl}-cyclohexylamine hydrochloride (intermediate H) and propionic acid.

Example 71

N-trans-(4-{2-[4-(6-Chloro-5-fluoro-benzo[d]isoxazol-3-14)-piperazin-1-yl]-ethyl}-cyclohexyl)-3-methoxy-propionamide

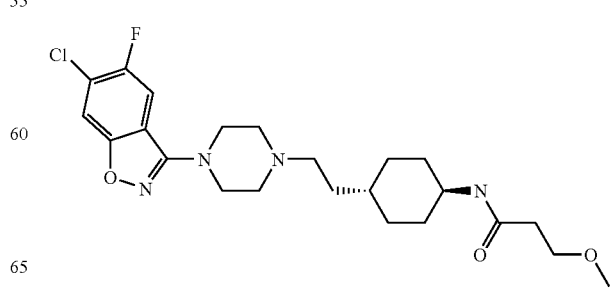

The title compound, MS: m/e=467.3 (M+H⁺), can be prepared in accordance with the general method of example 1, step 3 from 4-trans-{2-[4-(6-chloro-5-fluoro-benzo[d]isoxazol-3-yl)-piperazin-1-yl]-ethyl}-cyclohexylamine hydrochloride (intermediate H) and 3-methoxypropionic acid.

Example 72

N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide

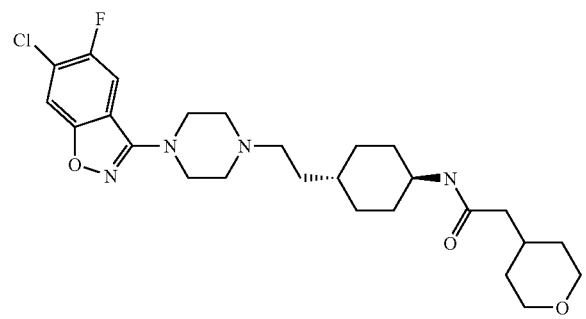

The title compound, MS: m/e=507.3 (M+H⁺), can be prepared in accordance with the general method of example 1, step 3 from 4-trans-{2-[4-(6-chloro-5-fluoro-benzo[d]isoxazol-3-yl)-piperazin-1-yl]-ethyl}-cyclohexylamine hydrochloride (intermediate H) and (tetrahydro-pyran-4-yl)-acetic acid.

Example 73

N-trans-(4-{2-[4-(5-Chloro-6-fluoro-benzo[d]isoxazol-3-yl)-piperazin-1-yl]-ethyl}-cyclohexyl)-acetamide

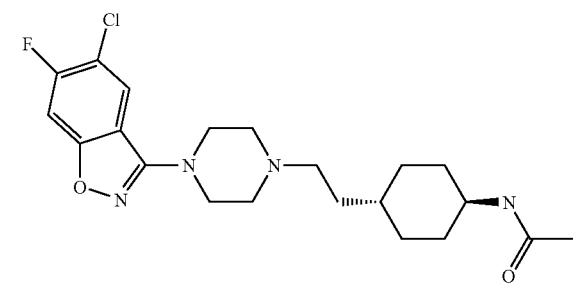

The title compound, MS: m/e=423.2 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and acetic acid.

Example 74

N-trans-(4-{2-[4-(5-Chloro-6-fluoro-benzo[d]isoxazol-3-yl)-piperazin-1-yl]-ethyl}-cyclohexyl)-3-methoxy-propionamide

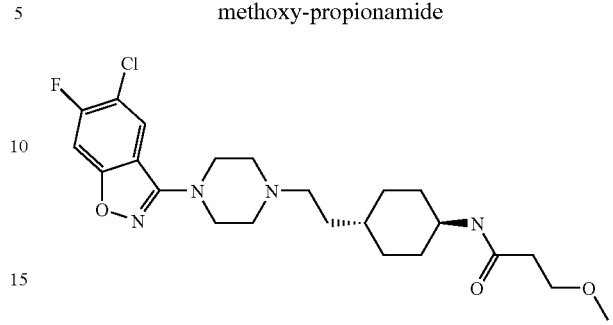

The title compound, MS: m/e=467.2 (M+H⁺, can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 3-methoxypropionic acid.

Example 75

N-trans-(4-{2-[4-(5-Chloro-6-fluoro-benzo[d]isoxazol-3-yl)-piperazin-1-yl]-ethyl}-cyclohexyl)-2-cyclopropyl-acetamide

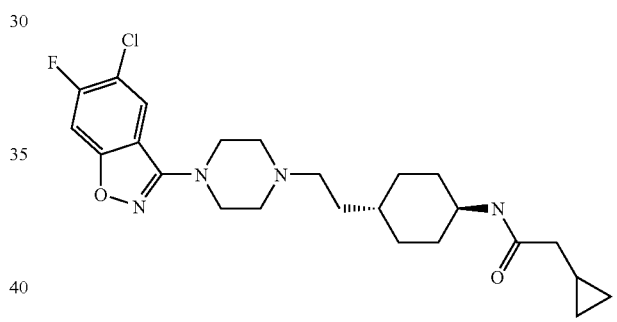

The title compound, MS: m/e=463.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and cyclopropylacetic acid.

Example 76

N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide

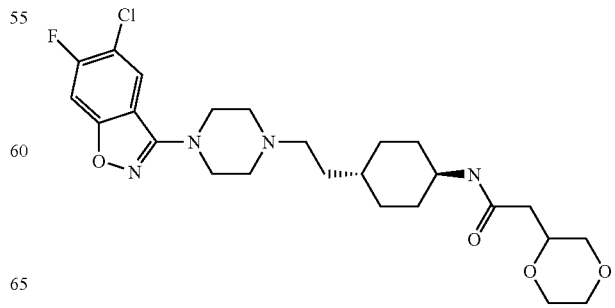

The title compound, MS: m/e=509.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and [1,4]dioxan-2-yl-acetic acid [can be prepared by LiOH hydrolysis of [1,4]dioxan-2-yl-acetic acid ethyl ester (example 15, step 1)].

Example 77

N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide

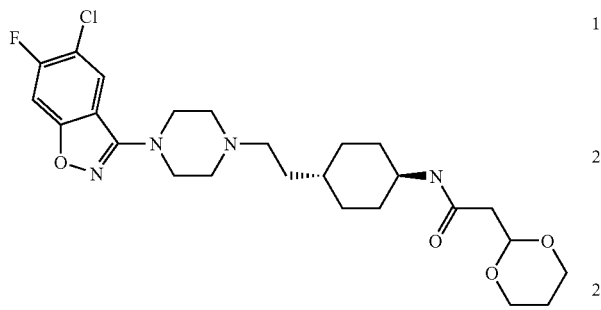

The title compound, MS: m/e=509.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and [1,3]dioxan-2-yl-acetic acid methyl ester (example 24, step 1).

Example 78

N-trans-(4-{2-[4-(5-Chloro-6-fluoro-benzo[d]isoxazol-3-yl)-piperazin-1-yl]-ethyl}-cyclohexyl)-3,3-dimethoxy-propionamide

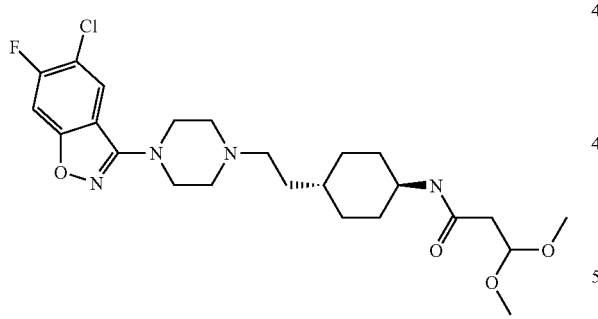

The title compound, MS: m/e=497.3 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and methyl 3,3-dimethoxypropionate.

Example 79

N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide

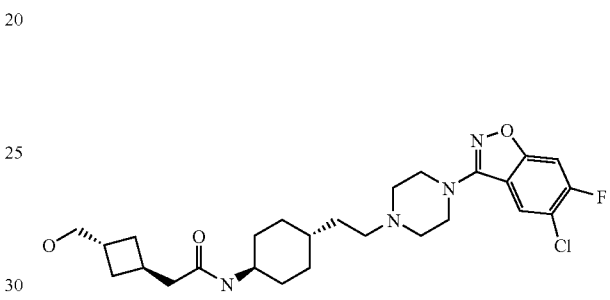

The title compound, MS: m/e=507.3 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and trans-(3-hydroxymethyl-cyclobutyl)-acetic acid methyl ester (intermediate E, step 5).

Example 80

N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide

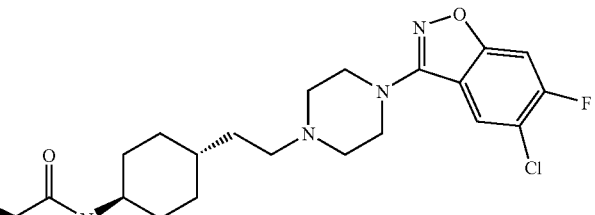

The title compound, MS: m/e=521.3 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and trans-(3-methoxymethyl-cyclobutyl)-acetic acid methyl ester (intermediate E).

Example 81

N-trans-(4-{2-[4-(5-Chloro-6-fluoro-benzo[d]isoxazol-3-yl)-piperazin-1-yl]-ethyl}-cyclohexyl)-3-methylsulfanyl-propionamide

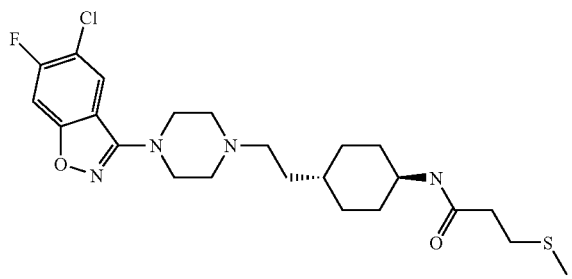

The title compound, MS: m/e=483.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 3-methylsulfanyl-propionic acid.

Example 82

N-trans-((4-{2-[4-(5-Chloro-6-fluoro-benzo[d]isoxazol-3-yl)-piperazin-1-yl]-ethyl}-cyclohexyl)-2-(3-methyl-isoxazol-5-yl)-acetamide

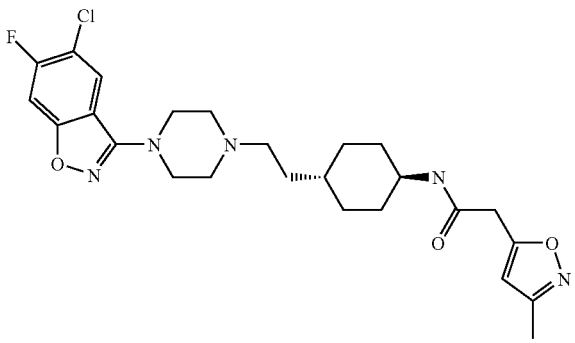

The title compound, MS: m/e=504.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and (3-methyl-isoxazol-5-yl)-acetic acid.

Example 83

3-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide

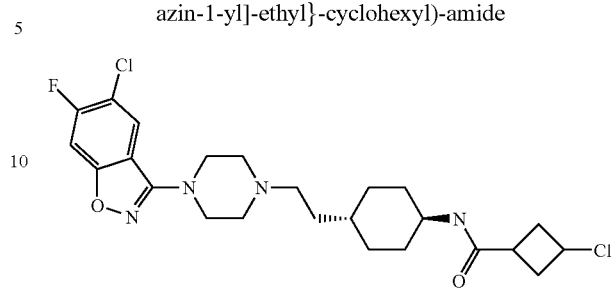

The title compound, MS: m/e=497.2 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 3-chloro-cyclobutanecarboxylic acid.

Example 84

5-Chloro-thiophene-2-carboxylic acid N-trans-(4-{2-[4-(5-chloro-6-fluoro-benzo[d]isoxazol-3-yl)-piperazin-1-yl]-ethyl}-cyclohexyl)-amide

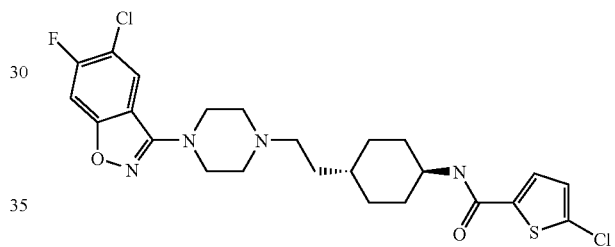

The title compound, MS: m/e=525.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 5-chloro-thiophene-2-carboxylic acid.

Example 85

5-Methoxy-thiophene-2-carboxylic acid N-trans-(4-{2-[4-(5-chloro-6-fluoro-benzo[d]isoxazol-3-yl)-piperazin-1-yl]-ethyl}-cyclohexyl)-amide

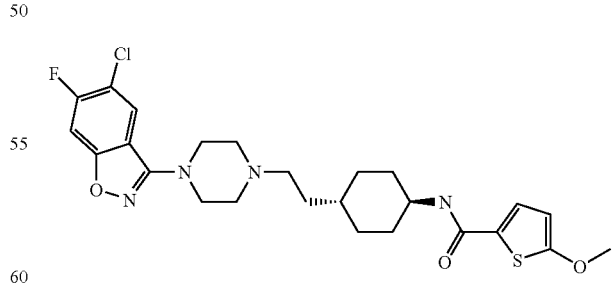

The title compound, MS: m/e=521.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 5-methoxy-thiophene-2-carboxylic acid.

Example 86

N-trans-(4-{2-[4-(5-Chloro-6-fluoro-benzo[d]isoxazol-3-yl)-piperazin-1-yl]-ethyl}-cyclohexyl)-propionamide

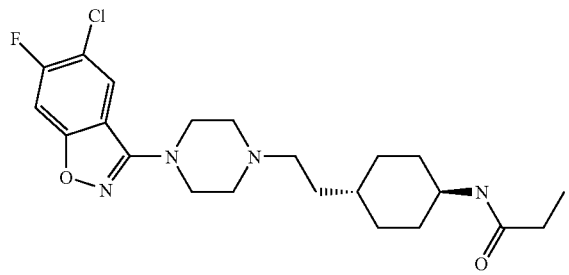

The title compound, MS: m/e=437.3 (M+H⁺, can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and propionic acid.

Example 87

N-trans-(4-{2-[4-(5-Chloro-6-fluoro-benzo[d]isoxazol-3-yl)-piperazin-1-yl]-ethyl}-cyclohexyl)-2-hydroxy-acetamide

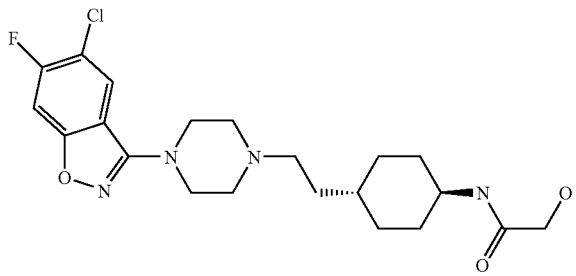

The title compound, MS: m/e=439.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and glycolic acid.

Example 88

N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide

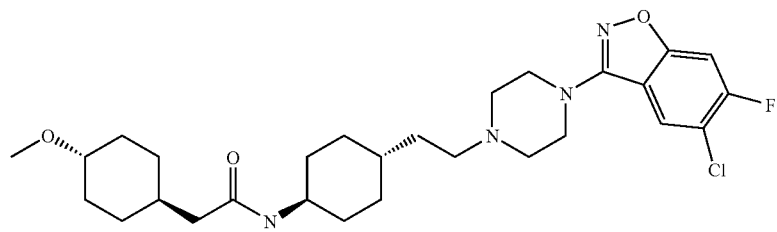

The title compound, MS: m/e=535.4 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and trans-(4-methoxy-cyclohexyl)-acetic acid methyl ester (intermediate B).

Example 89

N-trans-(4-{2-[4-(5-Chloro-6-fluoro-benzo[d]isoxazol-3-yl)-piperazin-1-yl]-ethyl}-cyclohexyl)-2-methanesulfonyl-acetamide

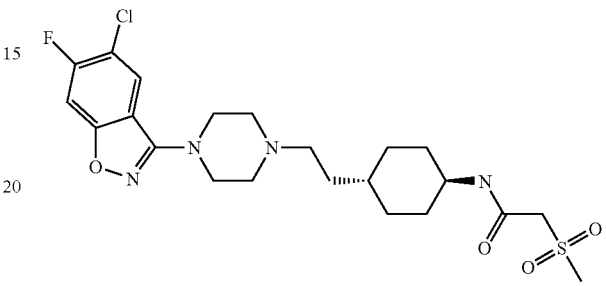

The title compound, MS: m/e=501.2 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and methanesulfonyl-acetic acid methyl ester.

Example 90

N-trans-(4-{2-[4-(5-Chloro-6-fluoro-benzo[d]isoxazol-3-yl)-piperazin-1-yl]-ethyl}-cyclohexyl)-3-methanesulfonyl-propionamide

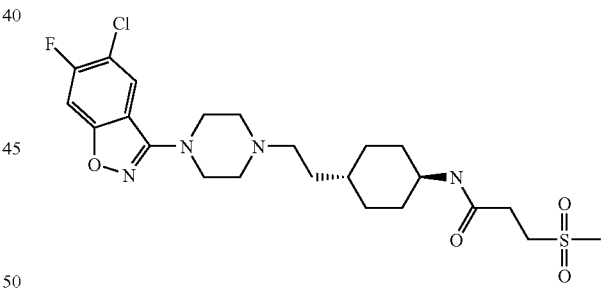

The title compound, MS: m/e=515.5 (M+H⁺), can be prepared in accordance with the general method of example 3 from 4-trans-{2-[4-(5-chloro-6-fluoro-benzo[d]isoxazol-3-yl)-piperazin-1-yl]-ethyl}-cyclohexylamine hydrochloride (intermediate I) and 3-methanesulfonyl-propionic acid methyl ester.

Example 91

N-trans-(4-{2-[4-(5-Chloro-6-fluoro-benzo[d]isox-azol-3-yl)-piperazin-1-yl]-ethyl}-cyclohexyl)-carbamic acid methyl ester

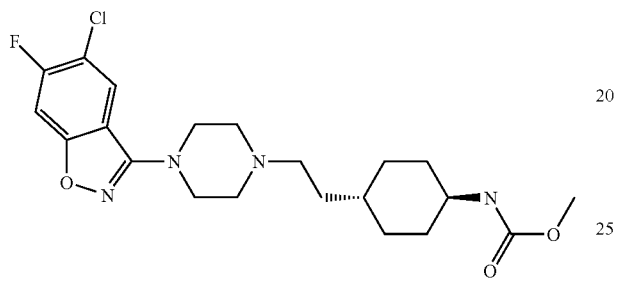

The title compound, MS: m/e=439.4/441.2 (M+H⁺), can be prepared in accordance with the general method of intermediate A, step 3 from 4-trans-{2-[4-(5-chloro-6-fluoro-benzo[d]isoxazol-3-yl)-piperazin-1-yl]-ethyl}-cyclohexylamine hydrochloride (intermediate I) and methylchloroformate.

Example 92

Cyclobutanecarboxylic acid N-trans-(4-{2-[4-(5-chloro-6-fluoro-benzo[d]isoxazol-3-yl)-piperazin-1-yl]-ethyl}-cyclohexyl)-amide

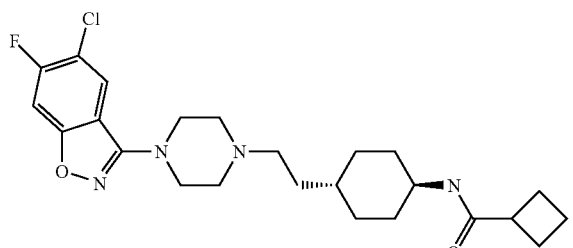

The title compound, MS: m/e=463.3/465.4 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and cyclobutanecarboxylic acid.

Example 93

N-trans-(4-{2-[4-(5-Chloro-6-fluoro-benzo[d]isoxazol-3-yl)-piperazin-1-yl]-ethyl}-cyclohexyl)-3,3,3-trifluoro-propionamide

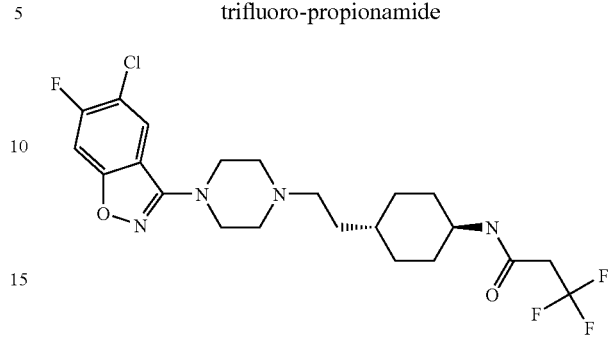

The title compound, MS: m/e=491.3/493.3 (M+H⁺), can be prepared in accordance with the general method of example 1, step 3 from 4-trans-{2-[4-(5-chloro-6-fluoro-benzo[d]isoxazol-3-yl)-piperazin-1-yl]-ethyl}-cyclohexylamine hydrochloride (intermediate I) and 3,3,3-trifluoro-propionic acid.

Example 94

N-trans-(4-{2-[4-(5,6-Dichloro-benzo[d]isoxazol-3-yl)-piperazin-1-yl]-ethyl}-cyclohexyl)-3-methoxy-propionamide

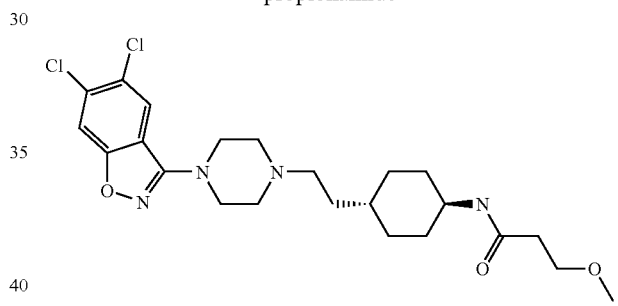

The title compound, MS: m/e=483.4 (M+H⁺), can be prepared in accordance with the general method of example 1, step 3 from 4-trans-{2-[4-(5,6-dichloro-benzo[d]isoxazol-3-yl)-piperazin-1-yl]-ethyl}-cyclohexylamine hydrochloride (intermediate J) and 3-methoxypropionic acid.

Example 95

Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide

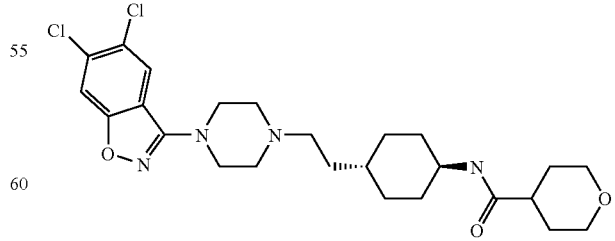

The title compound, MS: m/e=509.4 (M+H⁺), can be prepared in accordance with the general method of example 1, step 3 from 4-trans-{2-[4-(5,6-dichloro-benzo[d]isoxazol-3-yl)-piperazin-1-yl]-ethyl}-cyclohexylamine hydrochloride (intermediate J) and tetrahydro-pyran-4-carboxylic acid.

Example 96

N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide

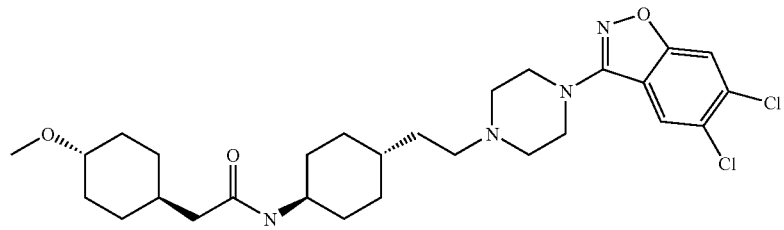

The title compound, MS: m/e=551.3 (M+H⁺), can be prepared in accordance with the general method of example 3 from 4-trans-{2-[4-(5,6-dichloro-benzo[d]isoxazol-3-yl)-piperazin-1-yl]-ethyl}-cyclohexylamine hydrochloride (intermediate J) and trans-(4-methoxy-cyclohexyl)-acetic acid methyl ester (intermediate B).

Example 97

N-trans-(4-{2-[4-(5,6-Dichloro-benzo[d]isoxazol-3-yl)-piperazin-1-yl]-ethyl}-cyclohexyl)-2-(tetrahydro-pyran-4-yl)-acetamide

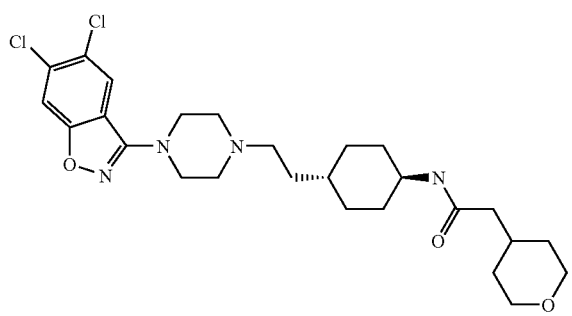

The title compound, MS: m/e=523.3 (M+H⁺), can be prepared in accordance with the general method of example 1, step 3 from 4-trans-{2-[4-(5,6-dichloro-benzo[d]isoxazol-3-yl)-piperazin-1-yl]-ethyl}-cyclohexylamine hydrochloride (intermediate J) and (tetrahydro-pyran-4-yl)-acetic acid.

Example 98

3-Methoxy-N-trans-(4-{2-[4-(6-methyl-benzo[d]isoxazol-3-yl)-piperazin-1-yl]-ethyl}-cyclohexyl)-propionamide

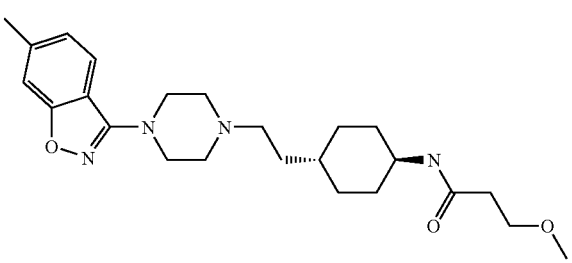

The title compound, MS: m/e=429.5 (M+H⁺), can be prepared in accordance with the general method of example 1, step 3 from 4-trans-{2-[4-(6-methyl-benzo[d]isoxazol-3-yl)-piperazin-1-yl]-ethyl}-cyclohexylamine hydrochloride (intermediate K) and 3-methoxypropionic acid.

Example 99

N-trans-(4-{2-[4-(6-Methyl-benzo[d]isoxazol-3-yl)-piperazin-1-yl]-ethyl}-cyclohexyl)-propionamide

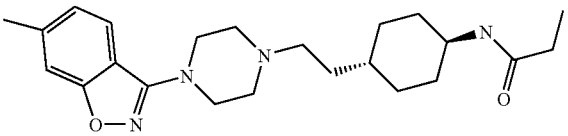

The title compound, MS: m/e=399.2 (M+H⁺), can be prepared in accordance with the general method of example 1, step 3 from 4-trans-{2-[4-(6-methyl-benzo[d]isoxazol-3-yl)-piperazin-1-yl]-ethyl}-cyclohexylamine hydrochloride (intermediate K) and propionic acid.

Example 100

2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide

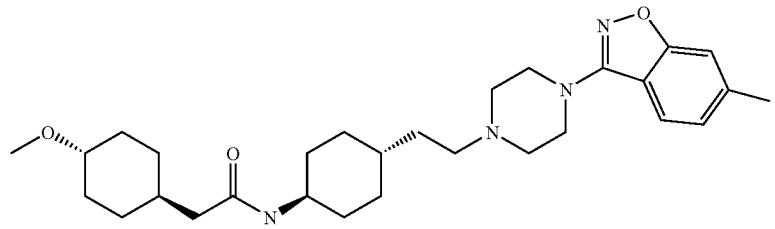

The title compound, MS: m/e=497.4 (M+H⁺), can be prepared in accordance with the general method of example 3 from 4-trans-{2-[4-(6-methyl-benzo[d]isoxazol-3-yl)-piperazin-1-yl]-ethyl}-cyclohexylamine hydrochloride (intermediate K) and trans-(4-methoxy-cyclohexyl)-acetic acid methyl ester (intermediate B).

Example 101

2-[1,3]-Dioxan-2-yl-N-trans-(4-{2-[4-(6-methyl-benzo[d]isoxazol-3-yl)-piperazin-1-yl]-ethyl}-cyclohexyl)-acetamide

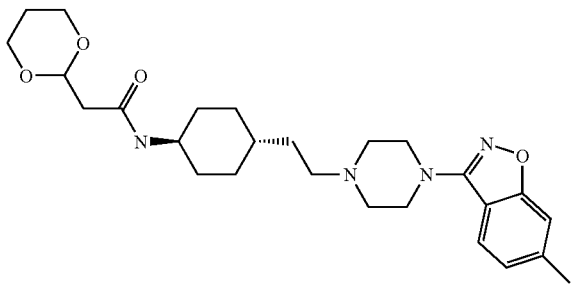

The title compound, MS: m/e=471.3 (M+H⁺), can be prepared in accordance with the general method of example 3 from 4-trans-{2-[4-(6-methyl-benzo[d]isoxazol-3-yl)-piperazin-1-yl]-ethyl}-cyclohexylamine hydrochloride (intermediate K) and [1,3]dioxan-2-yl-acetic acid methyl ester (example 24, step 1).

Example 102

2-[1,4]Dioxan-2-yl-N-trans-(4-{2-[4-(6-methyl-benzo[d]isoxazol-3-yl)-piperazin-1-yl]-ethyl}-cyclohexyl)-acetamide

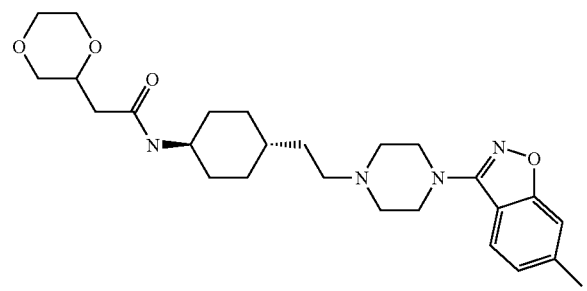

The title compound, MS: m/e=471.3 (M+H⁺), can be prepared in accordance with the general method of example 1, step 3 from 4-trans-{2-[4-(6-methyl-benzo[d]isoxazol-3-yl)-piperazin-1-yl]-ethyl}-cyclohexylamine hydrochloride (intermediate K) and [1,4]dioxan-2-yl-acetic acid (can be prepared by LiOH hydrolysis of [1,4]dioxan-2-yl-acetic acid ethyl ester, example 15, step 1).

Example 103

3,3-Dimethoxy-N-trans-(4-{2-[4-(6-methyl-benzo[d]isoxazol-3-yl)-piperazin-1-yl]-ethyl}-cyclohexyl)-propionamide

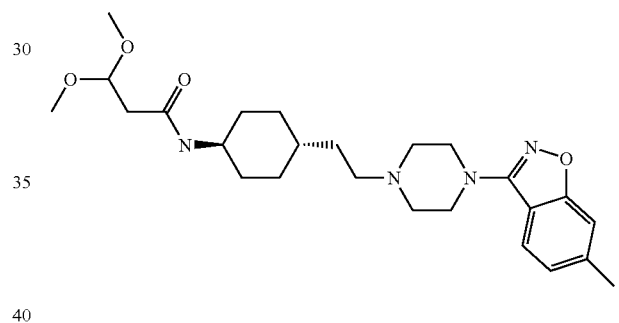

The title compound, MS: m/e=459.5 (M+H⁴), can be prepared in accordance with the general method of example 1, step 3 from 4-trans-{2-[4-(6-methyl-benzo[d]isoxazol-3-yl)-piperazin-1-yl]-ethyl}-cyclohexylamine hydrochloride (intermediate K) and 3,3-dimethoxy-propionic acid.

Example 104

3-Methoxy-N-trans-(4-{2-[4-(5-methyl-benzo[d]isoxazol-3-yl)-piperazin-1-yl]-ethyl}-cyclohexyl)-propionamide

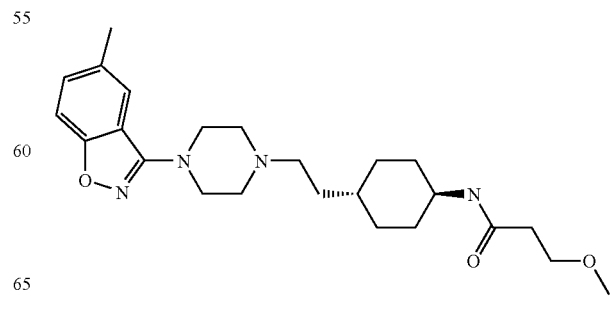

The title compound, MS: m/e=429.3 (M+H⁺), can be prepared in accordance with the general method of example 1, step 3 from 4-trans-{2-[4-(5-methyl-benzo[d]isoxazol-3-yl)-piperazin-1-yl]-ethyl}-cyclohexylamine hydrochloride (intermediate L) and 3-methoxypropionic acid.

Example 105

2-Methanesulfonyl-N-trans-(4-{2-[4-(6-methyl-benzo[d]isoxazol-3-yl)-piperazin-1-yl]-ethyl}-cyclohexyl)-acetamide

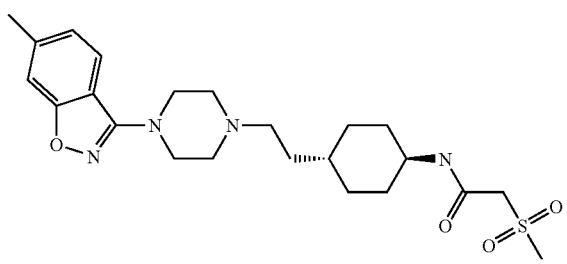

The title compound, MS: m/e=463.3 (M+H⁺), can be prepared in accordance with the general method of example 3 from 4-trans-{2-[4-(6-methyl-benzo[d]isoxazol-3-yl)-piperazin-1-yl]-ethyl}-cyclohexylamine hydrochloride (intermediate K) and methanesulfonyl-acetic acid methyl ester.

Example 106

N-trans-(4-{2-[4-(6-Fluoro-5-methyl-benzo[d]isoxazol-3-yl)-piperazin-1-yl]-ethyl}-cyclohexyl)-acetamide

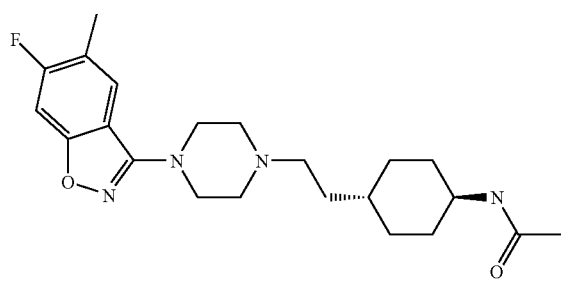

The title compound, MS: m/e=403.3 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and acetic acid.

Example 107

N-trans-(4-{2-[4-(6-Fluoro-5-methyl-benzo[d]isoxazol-3-yl)-piperazin-1-yl]-ethyl}-cyclohexyl)-2-methoxy-acetamide

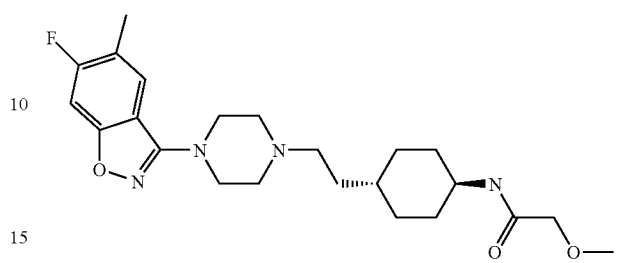

The title compound, MS: m/e=433.5 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and methoxyacetic acid.

Example 108

N-trans-(4-{2-[4-(6-Fluoro-5-methyl-benzo[d]isoxazol-3-yl)-piperazin-1-yl]-ethyl}-cyclohexyl)-3-methoxy-propionamide

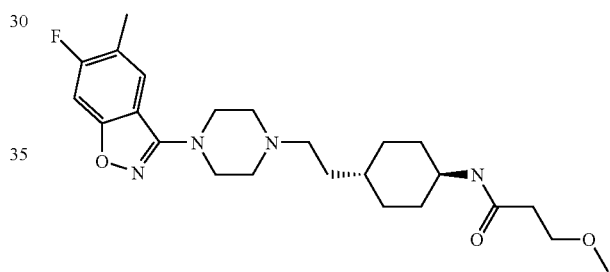

The title compound, MS: m/e=447.4 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and 3-methoxypropionic acid.

Example 109

2-Cyclopropyl-N-trans-(4-{2-[4-(6-fluoro-5-methyl-benzo[d]isoxazol-3-yl)-piperazin-1-yl]-ethyl}-cyclohexyl)-acetamide

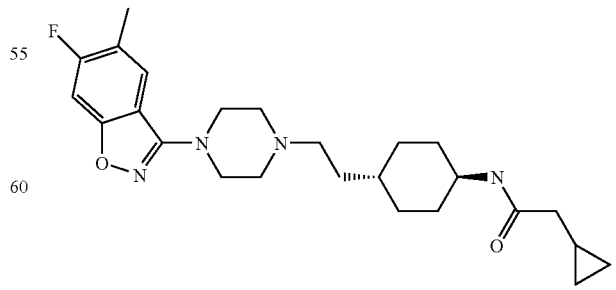

The title compound, MS: m/e=443.3 (M+H⁺), can be prepared in accordance with the general method of example 1,

Example 110

2-Ethoxy-N-trans-(4-{2-[4-(6-fluoro-5-methyl-benzo[d]isoxazol-3-yl)-piperazin-1-yl]-ethyl}-cyclohexyl)-acetamide

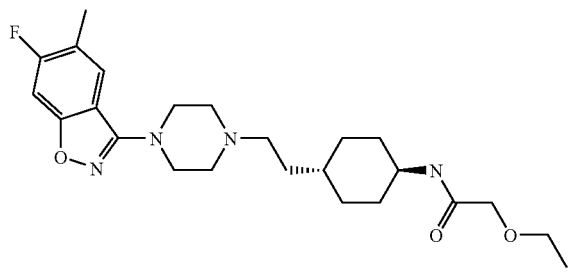

The title compound, MS: m/e=447.5 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and ethoxyacetic acid.

Example 111

2-[1,3]Dioxan-2-yl-N-trans-(4-{2-[4-(6-fluoro-5-methyl-benzo[d]isoxazol-3-yl)-piperazin-1-yl]-ethyl}-cyclohexyl)-acetamide

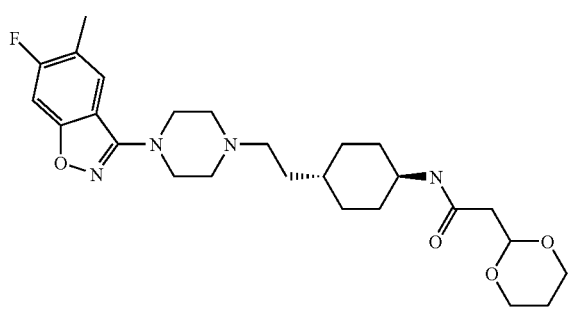

The title compound, MS: m/e=489.5 (M+H⁺), can be prepared in accordance with the general method of example 3 from 4-trans-{2-[4-(6-fluoro-5-methyl-benzo[d]isoxazol-3-yl)-piperazin-1-yl]-ethyl}-cyclohexylamine hydrochloride (intermediate M) and [1,3]dioxan-2-yl-acetic acid methyl ester (example 24, step 1).

Page 133 / step 3 from 4-trans-{2-[4-(6-fluoro-5-methyl-benzo[d]isoxazol-3-yl)-piperazin-1-yl]-ethyl}-cyclohexylamine hydrochloride (intermediate M) and cyclopropyl-acetic acid.

Example 112

N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide

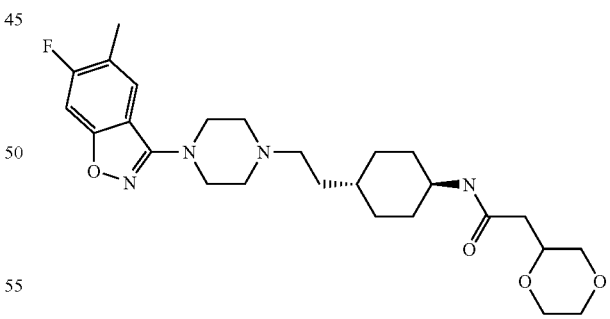

The title compound, MS: m/e=473.4 (M+H⁺), can be prepared in accordance with the general method of example 1, step 3 from 4-trans-{2-[4-(6-fluoro-benzo[d]isoxazol-3-yl)-piperazin-1-yl]-ethyl}-cyclohexylamine hydrochloride (intermediate N) and (tetrahydro-pyran-4-yl)-acetic acid.

Example 113

2-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide The title compound, MS: m/e=489.4 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and [1,4]dioxan-2-yl-acetic acid [can be prepared by LiOH hydrolysis of [1,4]dioxan-2-yl-acetic acid ethyl ester (example 15, step 1)].

Example 114

2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide

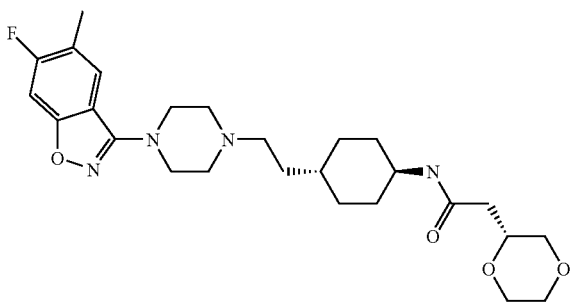

The title compound, MS: m/e=489.4 (M+H⁺), was obtained from separation of 2-[1,4]Dioxan-2-yl-N-(4-{2-[4-(6-fluoro-5-methyl-benzo[d]isoxazol-3-yl)-piperazin-1-yl]-ethyl}-cyclohexyl)-acetamide (example 113, step 1) using a chiral column (Reprosil Chiral NR).

Example 115

2-(S)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide

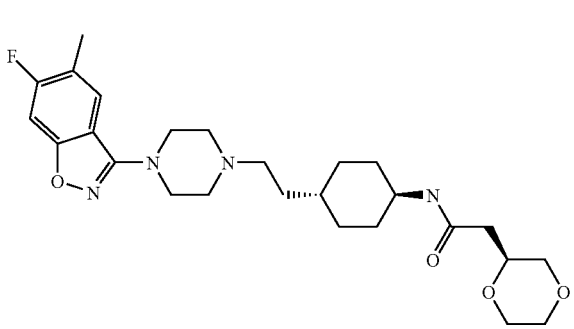

The title compound, MS: m/e=489.4 (M+H⁺), was obtained from separation of 2-[1,4]Dioxan-2-yl-N-(4-{2-[4-(6-fluoro-5-methyl-benzo[d]isoxazol-3-yl)-piperazin-1-yl]-ethyl}-cyclohexyl)-acetamide (example 113, step 1) using a chiral column (Reprosil Chiral NR).

Example 116

(S)-4,4,4-Trifluoro-N-trans-(4-{2-[4-(6-fluoro-5-methyl-benzo[d]isoxazol-3-yl)-piperazin-1-yl]-ethyl}-cyclohexyl)-3-hydroxy-butyramide

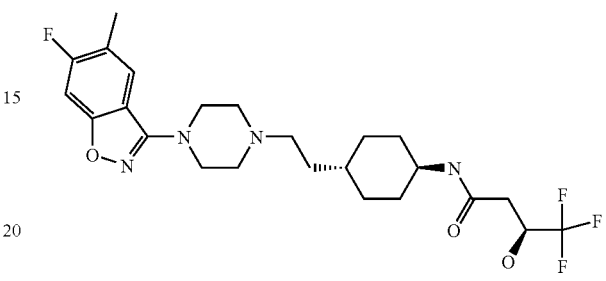

The title compound, MS: m/e=500.53 (M+H⁺), can be prepared in accordance with the general method of example 1, step 3 from 4-trans-{2-[4-(6-fluoro-benzo[d]isoxazol-3-yl)-piperazin-1-yl]-ethyl}-cyclohexylamine hydrochloride (intermediate N) and (S)-4,4,4-Trifluoro-3-hydroxybutyric acid.

Example 117

N-trans-(4-{2-[4-(6-Fluoro-5-methyl-benzo[d]isoxazol-3-yl)-piperazin-1-yl]-ethyl}-cyclohexyl)-2-(tetrahydro-pyran-2-yl)-acetamide

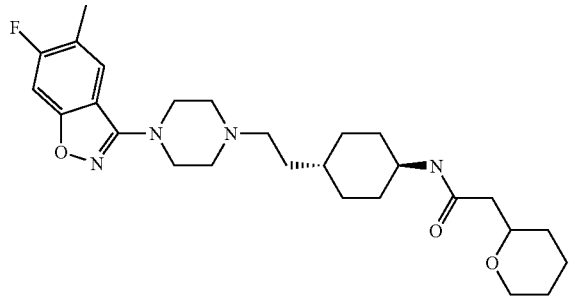

The title compound, MS: m/e=487.5 (M+H⁺), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and (Tetrahydro-pyran-2-yl)-acetic acid.

Example 118

N-trans-(4-{2-[4-(6-Fluoro-5-methyl-benzo[d]isoxazol-3-yl)-piperazin-1-yl]-ethyl}-cyclohexyl)-2-(tetrahydro-furan-2-yl)-acetamide

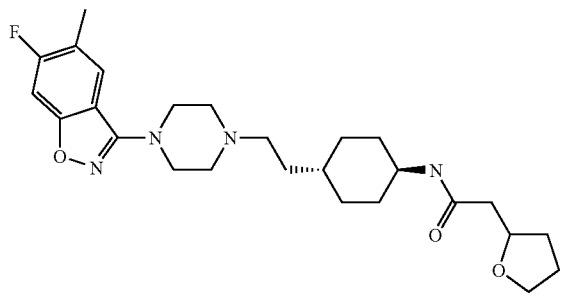

The title compound, MS: m/e=487.5 (M+H$^{+1}$), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and (Tetrahydro-furan-2-yl)-acetic acid.

Example 119

N-trans-(4-{2-[4-(6-Fluoro-5-methyl-benzo[d]isoxazol-3-yl)-piperazin-1-yl]-ethyl}-cyclohexyl)-2-methoxy-propionamide

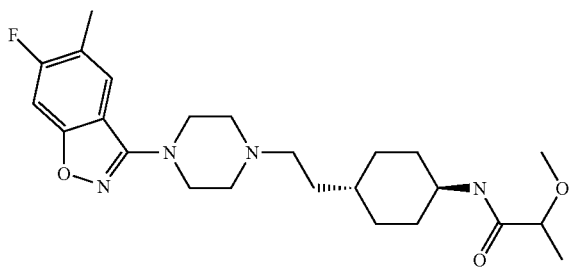

The title compound, MS: m/e=487.5 (M+H$^+$), can be prepared in accordance with the general method of example 1, step 3 from 4-trans-{2-[4-(6-fluoro-5-methyl-benzo[d]isoxazol-3-yl)-piperazin-1-yl]-ethyl}-cyclohexylamine hydrochloride (intermediate M) and 2-methoxypropionic acid (can be prepared by LiOH hydrolysis of [1,4]dioxan-2-yl-acetic acid ethyl ester, example 15, step 1).

Synthesis of Intermediates

Intermediate A

Trans-[4-(2-Oxo-ethyl)-cyclohexyl]-carbamic acid tert-butyl ester

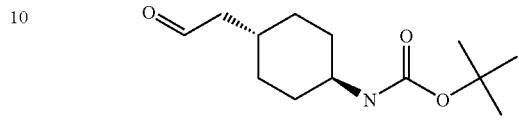

Step 1: trans-(4-Amino-cyclohexyl)-acetic acid (4-Nitro-phenyl)-acetic acid (50 g, 276 mmol) was added to a stirred solution of 22.08 g of 50% sodium hydroxide solution in 450 mL deionizated water. The clear yellow solution is transferred into a high-pressure autoclave that it charged with 30 g (511 mmol) of water-wet sponge nickel catalyst. The autoclave is sealed, flushed with nitrogen and then pressurized to 115 bar with hydrogen. The reaction mixture is stirred and heated to 125° C. for 48 h. At that time the autoclave is cooled, vented and charged under nitrogen with another 30 g (511 mmol) of the sponge nickel catalyst. The autoclave is flushed again with nitrogen and then pressurized to 115 bar and the vessel is heated to 130° C. while stirring (a maximum pressure of 130 bars is observed). Hydrogenation is continued for 5 days to 130° C. The autoclave is then cooled, vented and flushed with nitrogen and the contents are removed and filtered through filter aid to remove catalyst. After removal of the solvent 74 g of crude material was obtained. The intermediated is used directly in the next step without purification. MS (m/e): 158.3 (M+H$^+$).

Step 2: Trans-(4-amino-cyclohexyl)-acetic acid ethyl ester

A solution of the trans-(4-amino-cyclohexyl)-acetic acid obtained (74 g, 476 mmol) is adjusted to pH 5 with 25% HCl. The mixture was evaporated to dryness and dried under vacuum overnight. The residue was suspended in 146 mL of a 6.5N ethanolic HCl solution and 0.6 L of ethanol were added to the mixture. After 4 h refluxing, the mixture is cooled and filtered and the filtrate is concentrated to dryness under vacuum. The residue is dissolved in ethanol, treated with ether and cooled overnight in the refrigerator, to give the trans-(4-amino-cyclohexyl)-acetic acid ethyl ester hydrochloride (19.7 g, 32% on the two steps) as a white solid which was filtered and dried under vacuum. MS (m/e): 186.1 (M+W).

Step 3: trans-(4-tert-Butoxycarbonylamino-cyclohexyl)-acetic acid ethyl ester

To a solution of trans-(4-amino-cyclohexyl)-acetic acid ethyl ester (1.28 g, 7 mmol), in dichloromethane (15 ml), di-tert-butyl-dicarbonate (2.26 g, 10 mmol), triethylamine (0.699 ml, 7 mmol) and 4-dimethylaminopyridine (0.042 mL, 0.35 mmol) were added. The mixture was stirred for 8 h until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (4:2 to 3:2) to give 1.2 g (60%) of the product as a white solid. MS (m/e): 284.4 (M−H⁺).

Step 4: trans-[4-(2-Oxo-ethyl)-cyclohexyl]-carbamic acid tert-butyl ester

To a solution of trans-(4-tert-butoxycarbonylamino-cyclohexyl)-acetic acid ethyl ester (1.04 g, 4 mmol), in toluene (10 ml) at −78° C. a 1.2M solution of DIBAL-H (5.1 ml, 6 mmol) in toluene was added. The mixture was stirred at −78° C. until TLC after 0.5 h indicated completion of the reaction. Water was added and the solution was extracted three times with dichloromethane. The combined organic layers were washed with water and brine, dried over magnesium sulfate, filtered and evaporated. The crude product was used without purification on the next step. MS (m/e): 242.3 (M+H⁺).

Intermediate B trans-(4-Methoxy-cyclohexyl)-acetic acid methyl ester

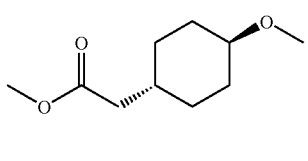

Step 1: trans-(4-Hydroxy-cyclohexyl)-acetic acid

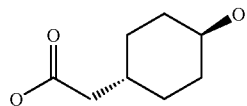

The title compound can be prepared in accordance with literature *Journal of the American Chemical Society* (1948), 70 1898-9.

Step 2: trans-(4-Hydroxy-cyclohexyl)-acetic acid methyl ester

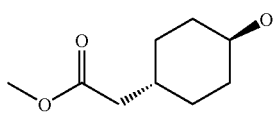

The ester can be prepared by refluxing the corresponding acid in methanol and catalytic sulfuric acid for 4 hours.

Step 3: trans-(4-Methoxy-cyclohexyl)-acetic acid methyl ester trans-(4-Hydroxy-cyclohexyl)-acetic acid methyl ester (500 mg, 2.90 mmol) were dissolved in 1.5 ml DMF and cooled to 0-5° C. Sodium hydride (190 mg, 4.35 mmol, 55%) and iodomethane (3.62 ml, 23.2 mmol) were added and the reaction mixture stirred for 4 hours at 0-5° C. The reaction mixture was quenched with saturated NaHCO3-solution and extracted with dichloromethane. The organic extract was washed with brine, dried with sodium sulfate, filtered and evaporated. The crude product (561 mg, quant.) was obtained as a colourless oil and used without any further purification for the next step.

Intermediate C

Trans-(3-Methoxy-cyclopentyl)-acetic acid methyl ester

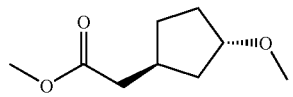

Step 1: Trans-(3-Hydroxy-cyclopentyl)-acetic acid methyl ester

The title compound can be prepared in accordance with literature *Helvetica Chimica Acta*—Vol. 75 (1992) Page 1945 and 1950.

Step 2: Trans-(3-Methoxy-cyclopentyl)-acetic acid methyl ester

The title compound was prepared in accordance with the general method of intermediate B, step 3 from rac-trans-(3-hydroxy-cyclopentyl)-acetic acid methyl ester.

Intermediate D

4-Trans-{2-[4-(5-Fluoro-benzo[d]isoxazol-3-yl)-piperazin-1-yl]-ethyl}-cyclohexylamine: hydrochloride

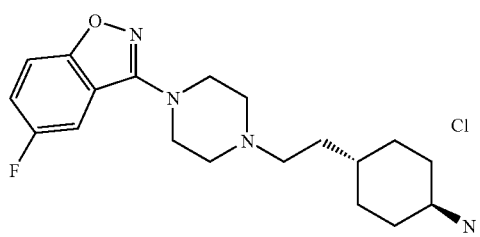

Step 1: 2,5-Difluoro-benzaldehyde oxime

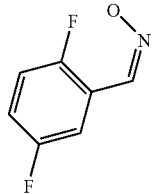

2,5-Difluorobenzaldehyde (28.5 g, 0.20 mol) was dissolved in 30 ml EtOH. 80 ml water, 80 g crushed ice and hydroxylamine hydrochloride (15.3 g, 0.22 mol) were added.

250 ml (0.50 mol) 2N NaOH were added drop wise and the yellow solution was stirred for 3 hours at room temperature. The reaction mixture was neutralized to pH 6 with acetic acid. The formed suspension was diluted with water and filtered. The crystals were washed with water and dried 2 hours at 50° C. and <20 mbar to obtain the desired product as a white solid (26.1 g, 83%). MS (m/e): 156.0 (M−H$^+$).

Step 2: 4-{2,5-Difluoro-phenyl)-[(E)-hydroxy-imino]-methyl}-piperazine-1-carboxylic acid tert-butyl ester

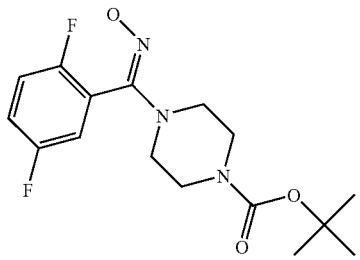

2,5-Difluoro-benzaldehyde oxime (26.1 g, 0.17 mol) was dissolved in 250 ml ACN and heated to 35-40° C. N-Chlorosuccinimide (23.3 g, 0.174 mmol) was added in portions (exothermic!) and the reaction mixture stirred for 30 minutes at 30-40° C. The reaction mixture was quenched with water and extracted two times with ethyl acetate. The organic extracts were washed with brine, dried with sodium sulfate, filtered and evaporated. The residue was dissolved in 400 ml dichloromethane and Et$_3$N (24.2 ml, 0.174 mmol) was added. Tert.-Butyl-1-piperazinecarboxylate (34.1 g, 0.183 mmol) was added and the mixture stirred for 30 minutes at room temperature. The reaction mixture was quenched with saturated NaHCO$_3$-solution and extracted with dichloromethane. The organic extracts were dried with sodium sulfate, filtered and evaporated. The crude product (61.9 g light yellow solid) was used without purification on the next step. MS (m/e): 342.2 (M+H$^+$).

Step 3: 4-(5-Fluoro-benzo[d]isoxazol-3-yl)-piperazine-1-carboxylic acid tert-butyl ester

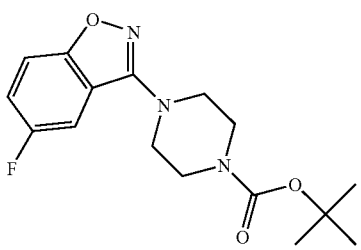

4-{(2,5-Difluoro-phenyl)-[(E)-hydroxyimino]-methyl}-piperazine-1-carboxylic acid tert-butyl ester (28.3 g, 82.9 mmol) was suspended in 200 ml dioxane and stirred together with 300 ml 30% KOH in water for 16 hours at reflux. The reaction mixture was cooled and extracted two times with dichloromethane. The organic extracts were dried with sodium sulfate, filtered and evaporated. The crude product was purified by flash-chromatography on silica gel with hexane:ethyl acetate (95:5 to 40:60) to give 22.7 g (85%) of the product as a white solid. MS (m/e): 322.2 (M−H$^+$).

Step 4: 5-Fluoro-3-piperazin-1-yl-benzo[d]isoxazole hydrochloride

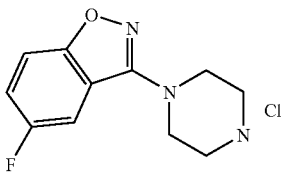

4-(5-Fluoro-benzo[d]isoxazol-3-yl)-piperazine-1-carboxylic acid tert-butyl ester (22.7 g, 70.6 mmol) was dissolved in 40 ml dichloromethane and 4N HCl in dioxane (264 ml, 1.06 mol) was added. The white suspension was stirred for 16 hours at room temperature, diluted with diisopropylether and filtered. The crystals were washed with diisopropylether and dried for 1 hour at 50° C. and <20 mbar, to get the desired salt as a white solid (18.2 g, quant.) [MS: m/e=222.3 (M+H$^+$)].

Step 5: Trans-(4-{2-[4-(5-Fluoro-benzo[d]isoxazol-3-yl)-piperazin-1-yl]-ethyl}-cyclohexyl)-carbamic acid tert-butyl ester The title compound, MS: m/e=447.1 (M+H$^+$), can be prepared in accordance with the general method of example 1, step 1 from 5-fluoro-3-piperazin-1-yl-benzo[d]isoxazole hydrochloride and trans-[4-(2-oxo-ethyl)-cyclohexyl]-carbamic acid tert-butyl ester (intermediate A).

Step 6: 4-Trans-{2-[4-(5-Fluoro-benzo[d]isoxazol-3-yl)-piperazin-1-yl]-ethyl}-cyclohexylamine hydrochloride The title compound, MS: m/e=347.1 (M+H$^+$), can be prepared in accordance with the general method of example 1, step 2 from trans-(4-{2-[4-(5-fluoro-benzo[d]isoxazol-3-yl)-piperazin-1-yl]-ethyl}-cyclohexyl)-carbamic acid tert-butyl ester.

Intermediate E

Trans-(3-Methoxymethyl-cyclobutyl)-acetic acid methyl ester

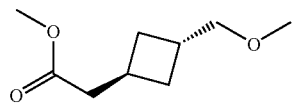

Step 1: 3-Benzyloxymethyl-cyclobutanone

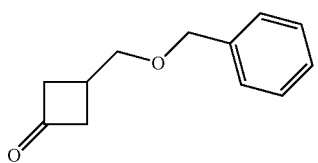

The title compound can be prepared in accordance with the literature in the patent WO2006063281.

Step 2: (3-Benzyloxymethyl-cyclobutylidene)-acetic acid methyl ester

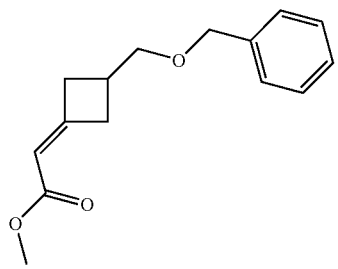

The title compound, MS: m/e=247.4 (M+H$^+$), can be prepared in accordance with the general method of example 10, step 2 from 3-benzyloxymethyl-cyclobutanone.

Step 3: (3-Benzyloxymethyl-cyclobutyl)-acetic acid methyl ester

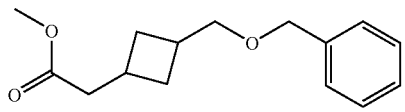

(3-Benzyloxymethyl-cyclobutylidene)-acetic acid methyl ester (5.4 g, 21.9 mmol) were dissolved in 80 ml methanol and cooled to 0-5° C. NiCl$_2$ (2.53 g, 19.5 mmol) and NaBH$_4$ (4.14 g, 109.6 mmol) were added slowly and the reaction mixture stirred for 1 hour at 0-5° C. The reaction mixture was quenched with 1N HCl and extracted two times with dichloromethane. The organic extract was washed with brine, dried with sodium sulfate, filtered and evaporated. The crude product (3.0 g, 55%) was obtained as a colourless liquid and used without any further purification for the next step. MS: m/e=249.1 (M+H$^+$).

Step 4: Trans-(3-Benzyloxymethyl-cyclobutyl)-acetic acid methyl ester

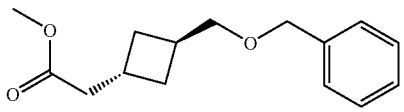

The title compound, MS: m/e=249.1 (M+H$^+$), was obtained from separation of (3-benzyloxymethyl-cyclobutyl)-acetic acid methyl ester using a chiral column (chiralpak AD).

Step 5: Trans-(3-Hydroxymethyl-cyclobutyl)-acetic acid methyl ester

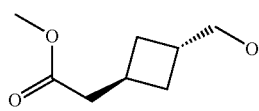

Prepared from trans-(3-benzyloxymethyl-cyclobutyl)-acetic acid methyl ester (980 mg, 3.95 mmol) by hydrogenation 16 hours at room temperature using Pd/C (10%) (420 mg) in ethylacetate (20 ml).

Step 6: Trans-(3-Methoxymethyl-cyclobutyl)-acetic acid methyl ester

The title compound can be prepared in accordance with the general method of intermediate B, step 3 from trans-(3-hydroxymethyl-cyclobutyl)-acetic acid methyl ester.

Intermediate F 4-trans-{2-[4-(6-Chloro-benzo[d]isoxazol-3-yl)-piperazin-1-yl]-ethyl}-cyclohexylamine hydrochloride

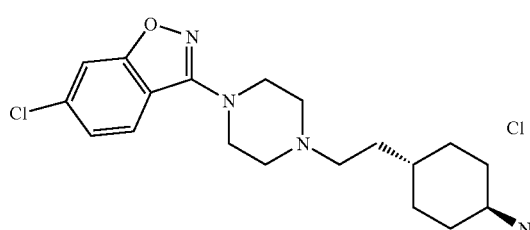

The title compound, MS: m/e=363.3 (M+H$^+$), can be prepared in accordance with the general method of intermediate D starting from 4-chloro-2-fluorobenzaldehyde.

Intermediate G 4-trans-{2-[4-(5,6-Difluoro-benzo[d]isoxazol-3-yl)-piperazin-1-yl]-ethyl}-cyclohexylamine hydrochloride

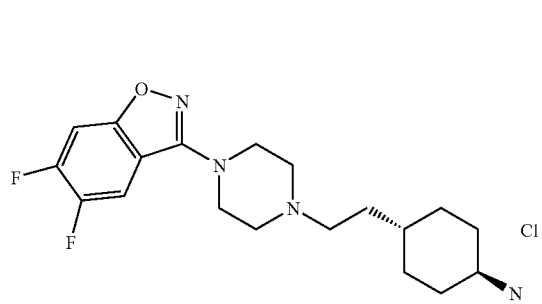

The title compound, MS: m/e=365.2 (M+H$^+$), can be prepared in accordance with the general method of intermediate D starting from 2,4,5-trifluorobenzaldehyde.

Intermediate H 4-trans-{2-[4-(6-Chloro-5-fluoro-benzo[d]isoxazol-3-yl)-piperazin-1-yl]-ethyl}-cyclohexylamine hydrochloride

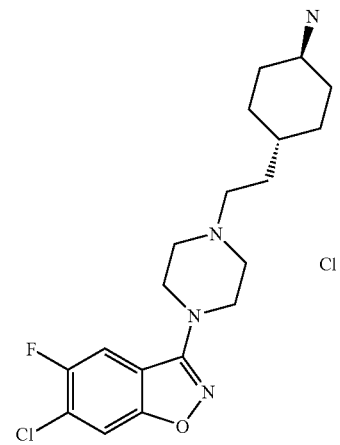

The title compound, MS: m/e=381.3 (M+H$^+$), can be prepared in accordance with the general method of intermediate D starting from 4-chloro-2,5-difluorobenzaldehyde.

Intermediate I 4-trans-{2-[4-(5-Chloro-6-fluoro-benzo[d]isoxazol-3-14)-piperazin-1-yl]-ethyl}-cyclohexylamine hydrochloride

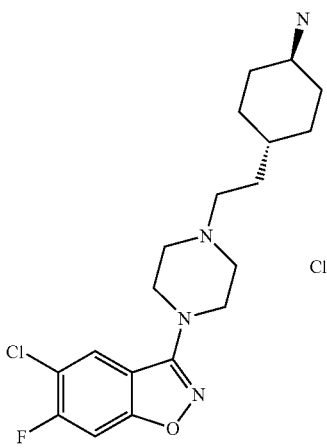

The title compound, MS: m/e=381.3 (M+H$^+$), can be prepared in accordance with the general method of intermediate D starting from 5-chloro-2,4-difluorobenzaldehyde.

Intermediate J 4-trans-{2-[4-(5,6-Dichloro-benzo[d]isoxazol-3-yl)-piperazin-1-yl]-ethyl}-cyclohexylamine hydrochloride

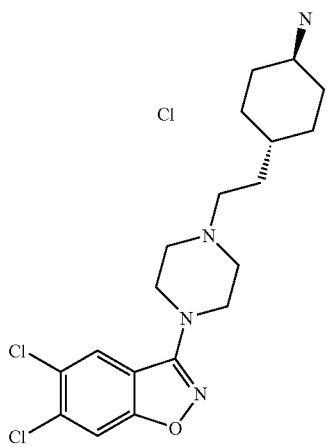

The title compound, MS: m/e=397.1 (M+H$^+$), can be prepared in accordance with the general method of intermediate D starting from 4,5-dichloro-2-fluorobenzaldehyde.

Intermediate K 4-trans-{2-[4-(6-Methyl-benzo[d]isoxazol-3-yl)-piperazin-1-yl]-ethyl}-cyclohexylamine hydrochloride

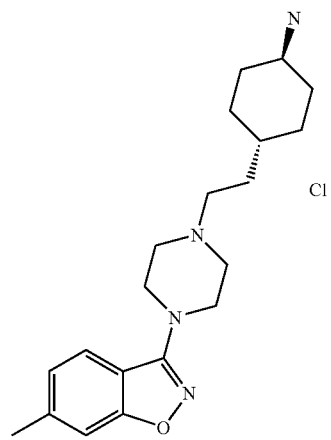

The title compound, MS: m/e=343.3 (M+H$^+$), can be prepared in accordance with the general method of intermediate D starting from 4-methyl-2-fluorobenzaldehyde.

Intermediate L 4-trans-{2-[4-(5-Methyl-benzo[d]isoxazol-3-yl)-piperazin-1-yl]-ethyl}-cyclohexylamine hydrochloride

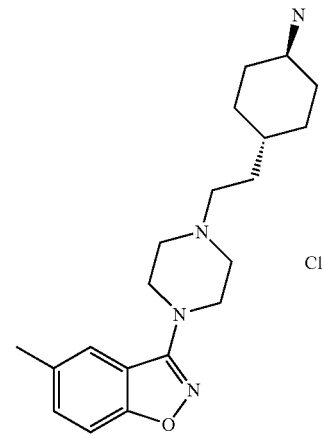

The title compound, MS: m/e=343.3 (M+H$^+$), can be prepared in accordance with the general method of intermediate D starting from 5-methyl-2-fluorobenzaldehyde.

Intermediate M 4-trans-{2-[4-(6-Fluoro-5-methyl-benzo[d]isoxazol-3-yl)-piperazin-1-yl]-ethyl}-cyclohexylamine hydrochloride

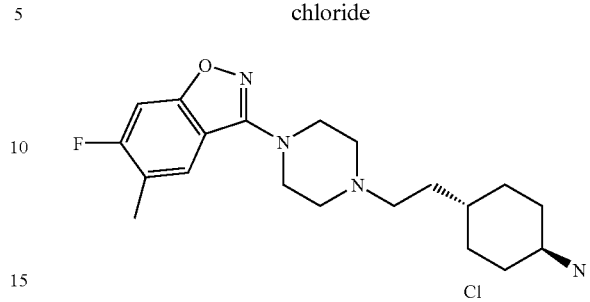

The title compound, MS: m/e=361.3 (M+H$^+$), can be prepared in accordance with the general method of intermediate D starting from 5-methyl-2,4-difluorobenzaldehyde.

Intermediate N 4-trans-{2-[4-(6-Fluoro-benzo[d]isoxazol-3-yl)-piperazin-1-yl]-ethyl}-cyclohexylamine hydrochloride

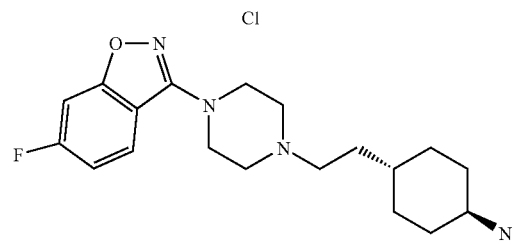

The title compound, MS: m/e=347.3 (M+H$^+$), can be prepared in accordance with the general method of intermediate D starting from 2,4-difluorobenzaldehyde.

The invention claimed is:

1. A compound of formula (I):

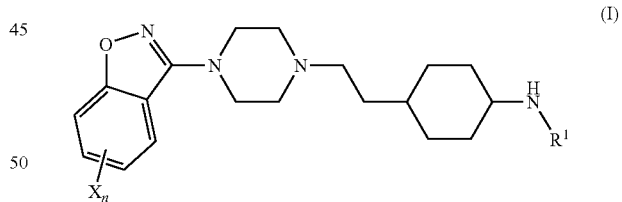

(I)

wherein:
X is independently halogen or $C_{1-6}$-alkyl;
n is 0, 1, or 2;
$R^1$ is —$COR^2$ or —$SO_2$—$C_{1-6}$-alkyl;
$R^2$ is $C_{1-6}$-alkyl, $C_{1-6}$-haloalkyl, $C_{1-6}$-hydroxyalkyl, $C_{1-6}$-alkoxy, 3 to 10 membered cycloalkyl, 4 to 10 membered heterocycloalkyl, or 5 to 10 membered heteroaryl, which are each optionally substituted by one or more substituents selected from the group consisting of:
halo,
hydroxy,
$C_{1-6}$-alkyl,
$C_{1-6}$-haloalkyl,
$C_{1-6}$-hydroxyalkyl, $C_{1-6}$-alkoxy,
$C_{1-6}$-alkoxy optionally substituted by one or more $R^a$,
—S—$C_{1-6}$-alkyl,
—$SO_2$—$C_{1-6}$-alkyl,
—$CONH_2$,
—CHO,
3 to 10 membered cycloalkyl optionally substituted by one or more $R^a$,
4 to 10 membered heterocycloalkyl optionally substituted by one or more $R^a$, and
5 to 10 membered heteroaryl optionally substituted by one or more $R^a$;
wherein $R^a$ is selected from the group consisting of:
halo,
hydroxy,
$C_{1-6}$-alkyl,
$C_{1-6}$-hydroxyalkyl,
$C_{1-6}$-haloalkyl, and
$C_{1-6}$-alkoxy;
or a pharmaceutically acceptable salt thereof.

2. The compound of claim 1 wherein $R^1$ is —$COR^2$.
3. The compound of claim 1 having formula (I'):

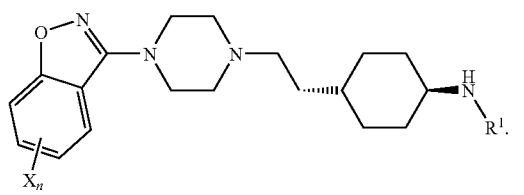

(I')

4. The compound of claim 3, wherein $R^1$ is —$COR^2$.
5. The compound of claim 1 having formula (Ia):

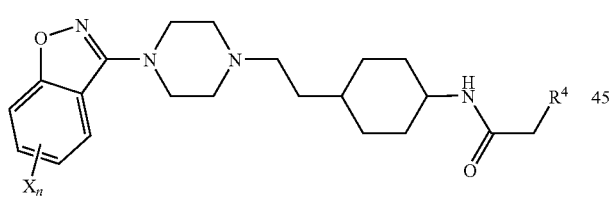

(Ia)

wherein:
$R^4$ is hydrogen,
hydroxyl,
$C_{1-6}$-alkyl,
$C_{1-6}$-hydroxyalkyl,
$C_{1-6}$-alkoxy,
3 to 6-membered cycloalkyl optionally substituted by one or more $R^b$, or
4 to 7-membered heterocycloalkyl optionally substituted by one or more $R^b$,
wherein $R^b$ is selected from the group consisting of:
hydroxy,
$C_{1-6}$-alkyl,
$C_{1-6}$-hydroxyalkyl, and
$C_{1-6}$-alkoxy.

6. The compound of claim 5 having formula (Ia'):

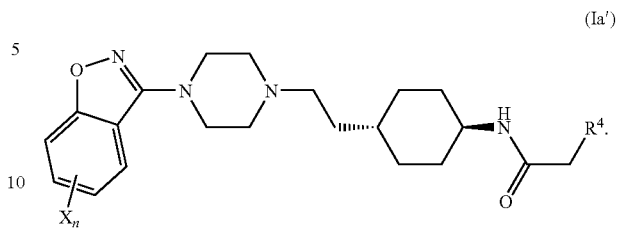

(Ia')

7. The compound of claim 6 wherein $R^4$ is $C_{1-6}$-alkoxy or $C_{1-6}$-alkoxy-$C_{1-6}$-alkyl.
8. The compound of claim 7 selected from the group consisting of:
N-trans-{4-[2-(4-benzo[d]isoxazol-3-yl)-piperazin-1-yl)-ethyl]-cyclohexyl}-3-methoxy-propionamide;
N-trans-(4-{2-[4-(5-Fluoro-benzo[d]isoxazol-3-yl)-piperazin-1-yl]-ethyl}-cyclohexyl)-3-methoxy-propionamide;
N-trans-(4-{2-[4-(5-Fluoro-benzo[d]isoxazol-3-yl)-piperazin-1-yl]-ethyl}-cyclohexyl)-2-methoxy-acetamide;
2-Ethoxy-N-trans-(4-{2-[4-(5-fluoro-benzo[d]isoxazol-3-yl)-piperazin-1-yl]-ethyl}-cyclohexyl)-acetamide;
N-trans-(4-{2-[4-(5-Fluoro-benzo[d]isoxazol-3-yl)-piperazin-1-yl]-ethyl}-cyclohexyl)-3,3-dimethoxy-propionamide;
N-trans-(4-{2-[4-(5-Fluoro-benzo[d]isoxazol-3-yl)-piperazin-1-yl]-ethyl}-cyclohexyl)-4,4-dimethoxy-butyramide;
N-trans-(4-{2-[4-(6-Chloro-benzo[d]isoxazol-3-yl)-piperazin-1-yl]-ethyl}-cyclohexyl)-3-methoxy-propionamide;
N-trans-(4-{2-[4-(6-Chloro-benzo[d]isoxazol-3-yl)-piperazin-1-yl]-ethyl}-cyclohexyl)-3-methoxy-butyramide;
N-trans-(4-{2-[4-(6-Chloro-benzo[d]isoxazol-3-yl)-piperazin-1-yl]-ethyl}-cyclohexyl)-3,3-dimethoxy-propionamide;
N-trans-(4-{2-[4-(5,6-Difluoro-benzo[d]isoxazol-3-yl)-piperazin-1-yl]-ethyl}-cyclohexyl)-3-methoxy-propionamide; and
N-trans-(4-{2-[4-(5,6-Difluoro-benzo[d]isoxazol-3-yl)-piperazin-1-yl]-ethyl}-cyclohexyl)-2-methoxy-acetamide.

9. The compound of claim 7 selected from the group consisting of:
N-trans-(4-{2-[4-(6-Chloro-5-fluoro-benzo[d]isoxazol-3-yl)-piperazin-1-yl]-ethyl}-cyclohexyl)-3-methoxy-propionamide;
N-trans-(4-{2-[4-(5-Chloro-6-fluoro-benzo[d]isoxazol-3-yl)-piperazin-1-yl]-ethyl}-cyclohexyl)-3-methoxy-propionamide;
N-trans-(4-{2-[4-(5-Chloro-6-fluoro-benzo[d]isoxazol-3-yl)-piperazin-1-yl]-ethyl}-cyclohexyl)-3,3-dimethoxy-propionamide;
N-trans-(4-{2-[4-(5,6-Dichloro-benzo[d]isoxazol-3-yl)-piperazin-1-yl]-ethyl}-cyclohexyl)-3-methoxy-propionamide;
3-Methoxy-N-trans-(4-{2-[4-(6-methyl-benzo[d]isoxazol-3-yl)-piperazin-1-yl]-ethyl}-cyclohexyl)-propionamide;
3,3-Dimethoxy-N-trans-(4-{2-[4-(6-methyl-benzo[d]isoxazol-3-yl)-piperazin-1-yl]-ethyl}-cyclohexyl)-propionamide;

3-Methoxy-N-trans-(4-{2-[4-(5-methyl-benzo[d]isox-azol-3-yl)-piperazin-1-yl]-ethyl}-cyclohexyl)-propionamide;

N-trans-(4-{2-[4-(6-Fluoro-5-methyl-benzo[d]isoxazol-3-yl)-piperazin-1-yl]-ethyl}-cyclohexyl)-2-methoxy-acetamide;

N-trans-(4-{2-[4-(6-Fluoro-5-methyl-benzo[d]isoxazol-3-yl)-piperazin-1-yl]-ethyl}-cyclohexyl)-3-methoxy-propionamide; and 2-Ethoxy-N-trans-(4-{2-[4-(6-fluoro-5-methyl-benzo[d]isoxazol-3-yl)-piperazin-1-yl]-ethyl}-cyclohexyl)-acetamide.

10. The compound of claim 6 wherein:

$R^4$ is 3 to 6-membered cycloalkyl optionally substituted by one or more $R^b$, or 4 to 7-membered heterocycloalkyl optionally substituted by one or more $R^b$;

wherein $R^b$ is selected from the group consisting of:
hydroxy,
$C_{1-6}$-alkyl,
$C_{1-6}$-hydroxyalkyl, and
$C_{1-6}$-alkoxy.

11. The compound of claim 10 selected from the group consisting of:

N-trans-{4-[2-(4-Benzo[d]isoxazol-3-yl)-piperazin-1-yl)-ethyl]-cyclohexyl}-2-trans-(3-methoxy-cyclopentyl)-acetamide;

N-trans-(4-{2-[4-(5-Fluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide;

2-[1,4]Dioxan-2-yl-N-trans-(4-{2-[4-(5-fluoro-benzo isoxazol-3-yl)-piperazin-1-yl]-ethyl}-cyclohexyl)-acetamide;

Rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;

N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide;

N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide;

N-trans-(4-{2-[4-(5-Fluoro-benzo isoxazol-3-yl)-piperazin-1-yl]-ethyl}-cyclohexyl)-2-(3-methyl-oxetan-3-yl)-acetamide; and N-trans-(4-{2-[4-(5-Fluoro-benzo[d]isoxazol-3-yl)-piperazin-1-yl]-ethyl}-cyclohexyl)-2-((S)-2,2,4-trimethyl-tetrahydro-pyran-4-yl-acetamide.

12. The compound of claim 10 selected from the group consisting of:

N-trans-(4-{2-[4-(5-Fluoro-benzo[d]isoxazol-3-yl)-piperazin-1-yl]-ethyl}-cyclohexyl)-2-((R)-2,2,4-trimethyl-tetrahydro-pyran-4-yl)-acetamide;

2-[1,3]Dioxan-2-yl-N-trans-(4-{2-[4-(5-fluoro-benzo[d]isoxazol-3-yl)-piperazin-1-yl]-ethyl}-cyclohexyl)-acetamide;

N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide;

N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide;

N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide;

N-trans-(4-{2-[4-(6-Chloro-benzo[d]isoxazol-3-yl)-piperazin-1-yl]ethyl}-cyclohexyl)-2-(tetrahydro-pyran-2-yl)-acetamide;

N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide;

N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide;

N-trans-(4-{2-[4-(6-Chloro-benzo[d]isoxazol-3-yl)-piperazin-1-yl]-ethyl}-cyclohexyl)-2-(tetrahydro-pyran-4-yl)-acetamide; and N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide.

13. The compound of claim 10 selected from the group consisting of:

N-trans-(4-{2-[4-(6-Chloro-benzo[d]isoxazol-3-yl)-piperazin-1-yl]-ethyl}-cyclohexyl)-2-oxetan-3-yl-acetamide;

N-trans-(4-{2-[4-(6-Chloro-benzo[d]isoxazol-3-yl)-piperazin-1-yl]ethyl}-cyclohexyl)-2-trans-(3-methoxymethyl-cyclobutyl)-acetamide;

N-trans-(4-{2-[4-(6-Chloro-benzo[d]isoxazol-3-yl)-piperazin-1-yl]ethyl}-cyclohexyl)-2-(R)-tetrahydro-pyran-2-yl-acetamide;

N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide;

N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide;

N-trans-(4-{2-[4-(6-Chloro-benzo[d]isoxazol-3-yl)-piperazin-1-yl]-ethyl}-cyclohexyl)-2-cyclopropyl-acetamide;

N-trans-(4-{2-[4-(5,6-Difluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide; and N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide.

14. The compound of claim 10 selected from the group consisting of:

N-trans-(4-{2-[4-(5,6-Difluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide;

N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide;

N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide;

N-trans-(4-{2-[4-(5-Chloro-6-fluoro-benzo[d]isoxazol-3-yl)-piperazin-1-yl]-ethyl}-cyclohexyl)-2-cyclopropyl-acetamide;

N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide;

N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide; and N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide.

15. The compound of claim 10 selected from the group consisting of:

N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide;

N-trans-(4-{2-[4-(5,6-Dichloro-benzo[d]isoxazol-3-yl)-piperazin-1-yl]-ethyl}-cyclohexyl)-2-(tetrahydro-pyran-4-yl)-acetamide;

2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide;

2-[1,3]Dioxan-2-yl-N-trans-(4-{2-[4-(6-methyl-benzo[d]isoxazol-3-yl)-piperazin-1-yl]-ethyl}-cyclohexyl)-acetamide;

2-[1,4]Dioxan-2-yl-N-trans-(4-{2-[4-(6-methyl-benzo[d]isoxazol-3-yl)-piperazin-1-yl]-ethyl}-cyclohexyl)-acetamide;

2-Cyclopropyl-N-trans-(4-{2-[4-(6-fluoro-5-methyl-benzo[d]isoxazol-3-yl)-piperazin-1-yl]-ethyl}-cyclohexyl)-acetamide;

2-[1,3]Dioxan-2-yl-N-trans-(4-{2-[4-(6-fluoro-5-methyl-benzo[d]isoxazol-3-yl)-piperazin-1-yl]-ethyl}-cyclohexyl)-acetamide; and N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide.

16. The compound of claim 1 having formula (Ib):

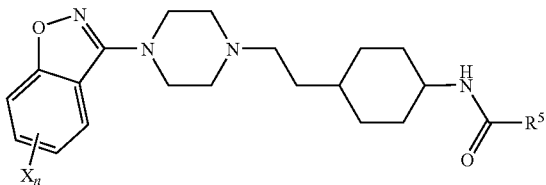

(Ib)

wherein:

$R^5$ is 4 to 7-membered heterocycloalkyl; or 3 to 6-membered cycloalkyl optionally substituted by one or more halogen, hydroxyl or $C_{1-6}$-alkoxy.

17. The compound of claim 16 having formula (Ib')

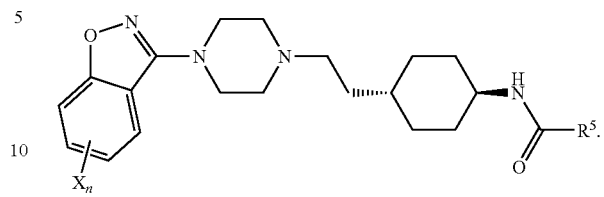

(Ib')

18. The compound of claim 17 selected from the group consisting of:

4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;

3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;

Tetrahydro-pyran-4-carboxylic acid N-trans-(4-{2-[4-(6-chloro-benzo[d]isoxazol-3-yl)-piperazin-1-yl]-ethyl}-cyclohexyl)-amide;

Tetrahydro-furan-3-carboxylic acid N-trans-(4-{2-[4-(6-chloro-benzo[d]isoxazol-3-yl)-piperazin-1-yl]-ethyl}-cyclohexyl)-amide;

1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide;

(S)-Tetrahydro-furan-3-carboxylic acid (4-{2-[4-(6-chloro-benzo[d]isoxazol-3-yl)-piperazin-1-yl]-ethyl}-cyclohexyl)-amide;

4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide;

4-Methoxy-cyclohexanecarboxylic acid N-trans-(4-{2-[4-(5,6-difluoro-benzo[d]isoxazol-3-yl)-piperazin-1-yl]-ethyl}-cyclohexyl)-amide;

Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide;

1-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide;

Cyclobutanecarboxylic acid N-trans-(4-{2-[4-(5-chloro-6-fluoro-benzo[d]isoxazol-3-yl)-piperazin-1-yl]-ethyl}-cyclohexyl)-amide; and Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide.

19. The compound according to claim 1, wherein the piperazinyl-ethyl moiety and the N-amide moiety are attached to the cyclohexyl-ring in a trans-configuration.

20. The compound of claim 1, wherein X is fluoro or methyl.

21. The compound of claim 1, wherein n is 1 or 2.

22. The compound of claim 1, wherein $R^2$ is $C_{1-6}$-alkyl which is optionally substituted by one substituent selected from the group consisting of $C_{1-6}$-alkoxy, —$SO_2$—$C_{1-6}$-alkyl and 6 membered heterocycloalkyl.

23. The compound of claim 1, wherein $R^2$ is methyl, methyl substituted by methanesulfonyl or [1,4]dioxin-2-yl or ethyl substituted by methoxy.

24. The compound of claim 1 selected from the group consisting of:

N-trans-{4-[2-(4-benzo[d]isoxazol-3-yl)-piperazin-1-yl)-ethyl]-cyclohexyl}-3-methoxy-propionamide;
N-trans-{4-[2-(4-benzo[d]isoxazol-3-yl)-piperazin-1-yl)-ethyl]-cyclohexyl}-acetamide;
N-trans-{4-[2-(4-Benzo[d]isoxazol-3-yl)-piperazin-1-yl)-ethyl]-cyclohexyl}-2-trans-(3-methoxy-cyclopentyl)-acetamide;
N-trans-{4-[2-(4-Benzo[d]isoxazol-3-yl)-piperazin-1-yl)-ethyl]-cyclohexyl}-2-hydroxy-acetamide;
N-trans-(4-{2-[4-(5-Fluoro-benzo[d]isoxazol-3-yl)-piperazin-1-yl]-ethyl}-cyclohexyl)-3-methoxy-propionamide;
N-trans-(4-{2-[4-(5-Fluoro-benzo[d]isoxazol-3-yl)-piperazin-1-yl]-ethyl}-cyclohexyl)-2-trans-(4-methoxy-cyclohexyl)-acetamide;
Tetrahydro-pyran-4-carboxylic acid-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-2-(tetrahydro-pyran-4-yl)-acetamide;
N-trans-(4-{2-[4-(5-Fluoro-benzo[d]isoxazol-3-yl)-piperazin-1-yl]-ethyl}-cyclohexyl)-2-methoxy-acetamide;
N-trans-(4-{2-[4-(5-Fluoro-benzo[d]isoxazol-3-yl)-piperazin-1-yl]-ethyl}-cyclohexyl)-2-(4-isopropoxy-cyclohexyl)-acetamide; and
N-trans-(4-{2-[4-(5-Fluoro-benzo[d]isoxazol-3-yl)-piperazin-1-yl]-ethyl}-cyclohexyl)-3-hydroxy-3-methyl-butyramide.

25. The compound of claim 1 selected from the group consisting of:

2-Ethoxy-N-trans-(4-{2-[4-(5-fluoro-benzo[d]isoxazol-3-yl)-piperazin-1-yl]-ethyl}-cyclohexyl)-acetamide;
4-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-methanesulfonamide;
2-[1,4]Dioxan-2-yl-N-trans-(4-{2-[4-(5-fluoro-benzo[d]isoxazol-3-yl)-piperazin-1-yl]-ethyl}-cyclohexyl)-acetamide;
3-Methoxy-cyclohexanecarboxylic acid N-trans-(4-{2-[4-(5-fluoro-benzo[d]isoxazol-3-yl)-piperazin-1-yl]-ethyl}-cyclohexyl)-amide;
N-trans-(4-{2-[4-(5-Fluoro-benzo[d]isoxazol-3-yl)-piperazin-1-yl]-ethyl}-cyclohexyl)-malonamide;
Rac-2-(2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;
N-trans-(4-{2-[4-(5-Fluoro-benzo[d]isoxazol-3-yl)-piperazin-1-yl]-ethyl}-cyclohexyl)-2-(1R,4S)-7-oxa-bicyclo[2.2.1]hept-2-yl-acetamide;
N-trans-(4-{2-[4-(5-Fluoro-benzo[d]isoxazol-3-yl)-piperazin-1-yl]-ethyl}-cyclohexyl)-2-trans-(3-hydroxymethyl-cyclobutyl)-acetamide;
N-trans-(4-{2-[4-(5-Fluoro-benzo[d]isoxazol-3-yl)-piperazin-1-yl]ethyl}-cyclohexyl)-2-(3-methyl-oxetan-3-yl)-acetamide; and
2-((S)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide.

26. The compound of claim 1 selected from the group consisting of:

2-((R)-2,2-Dimethyl-tetrahydro-pyran-4-yl)-N-trans-(4-{2-[4-(5-fluoro-benzo[d]isoxazol-3-yl)-piperazin-1-yl]-ethyl}-cyclohexyl)-acetamide;
2-[1,3]Dioxan-2-yl-N-trans-(4-{2-[4-(5-fluoro-benzo[d]isoxazol-3-yl)-piperazin-1-yl]-ethyl}-cyclohexyl)-acetamide;
N-trans-(4-{2-[4-(5-Fluoro-benzo[d]isoxazol-3-yl)-piperazin-1-yl]-ethyl}-cyclohexyl)-2-(4-methoxy-piperidin-1-yl)-acetamide;
N-trans-(4-{2-[4-(5-Fluoro-benzo[d]isoxazol-3-yl)-piperazin-1-yl]-ethyl}-cyclohexyl)-3,3-dimethoxy-propionamide;
N-trans-(4-{2-[4-(5-Fluoro-benzo[d]isoxazol-3-yl)-piperazin-1-yl]-ethyl}-cyclohexyl)-2-trans-(3-methoxymethyl-cyclobutyl)-acetamide;
N-trans-(4-{2-[4-(5-Fluoro-benzo[d]isoxazol-3-yl)-piperazin-1-yl]-ethyl}-cyclohexyl)-4,4-dimethoxy-butyramide;
N-trans-(4-{2-[4-(6-Chloro-benzo[d]isoxazol-3-yl)-piperazin-1-yl]-ethyl}-cyclohexyl)-3-methoxy-propionamide;
N-trans-(4-{2-[4-(6-Chloro-benzo[d]isoxazol-3-yl)-piperazin-1-yl]-ethyl}-cyclohexyl)-acetamide;
N-trans-(4-{2-[4-(6-Chloro-benzo[d]isoxazol-3-yl)-piperazin-1-yl]-ethyl}-cyclohexyl)-2-trans-(4-methoxy-cyclohexyl)-acetamide;
Tetrahydro-pyran-4-carboxylic acid N-trans-(4-{2-[4-(6-chloro-benzo[d]isoxazol-3-yl)-piperazin-1-yl]-ethyl}-cyclohexyl)-amide; and
N-trans-(4-{2-[4-(6-Chloro-benzo[d]isoxazol-3-yl)-piperazin-1-yl]-ethyl}-cyclohexyl)-rac-3,3,3-trifluoro-2-hydroxy-propionamide.

27. The compound of claim 1 selected from the group consisting of:

Tetrahydro-furan-3-carboxylic acid N-trans-(4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-2-(tetrahydro-pyran-2-yl)-acetamide;
N-trans-(4-{2-[4-(6-Chloro-benzo[d]isoxazol-3-yl)-piperazin-1-yl]-ethyl}-cyclohexyl)-2-trans-(3-methoxy-cyclopentyl)-acetamide;
N-trans-(4-{2-[4-(6-Chloro-benzo[d]isoxazol-3-yl)-piperazin-1-yl]-ethyl}-cyclohexyl)-3-methoxy-butyramide;
1-Hydroxy-cyclopropanecarboxylic acid N-trans-(4-{2-[4-(6-chloro-benzo[d]isoxazol-3-yl)-piperazin-1-yl]-ethyl}-cyclohexyl)-amide;
N-trans-(4-{2-[4-(6-Chloro-benzo[d]isoxazol-3-yl)-piperazin-1-yl]-ethyl}-cyclohexyl)-2-(4-methoxy-4-methyl-cyclohexyl)-acetamide;
N-trans-(4-{2-[4-(6-Chloro-benzo[d]isoxazol-3-yl)-piperazin-1-yl]-ethyl}-cyclohexyl)-2-(tetrahydro-pyran-4-yl)-acetamide;
N-trans-(4-{2-[4-(6-Chloro-benzo[d]isoxazol-3-yl)-piperazin-1-yl]-ethyl}-cyclohexyl)-propionamide;
N-trans-(4-{2-[4-(6-Chloro-benzo[d]isoxazol-3-yl)-piperazin-1-yl]-ethyl}-cyclohexyl)-2-hydroxy-acetamide;
N-trans-(4-{2-[4-(6-Chloro-benzo[d]isoxazol-3-yl)-piperazin-1-yl]-ethyl}-cyclohexyl)-2-trans-(4-hydroxy-cyclohexyl)-acetamide; and
N-trans-(4-{2-[4-(6-Chloro-benzo[d]isoxazol-3-yl)-piperazin-1-yl]-ethyl}-cyclohexyl)-3-hydroxy-3-methyl-butyramide.

28. The compound of claim 1 selected from the group consisting of:
- (S)—N-(4-{2-[4-(6-Chloro-benzo[d]isoxazol-3-yl)-piperazin-1-yl]-ethyl}-cyclohexyl)-3-hydroxy-butyramide;
- (S)-Tetrahydro-furan-3-carboxylic acid (4-{2-[4-(6-chloro-benzo[d]isoxazol-3-yl)-piperazin-1-yl]-ethyl}-cyclohexyl)-amide;
- N-trans-(4-{2-[4-(6-Chloro-benzo[d]isoxazol-3-yl)-piperazin-1-yl]-ethyl}-cyclohexyl)-2-oxetan-3-yl-acetamide;
- N-trans-(4-{2-[4-(6-Chloro-benzo[d]isoxazol-3-yl)-piperazin-1-yl]-ethyl}-cyclohexyl)-2-trans-(3-methoxymethyl-cyclobutyl)-acetamide;
- N-trans-(4-{2-[4-(6-Chloro-benzo[d]isoxazol-3-yl)-piperazin-1-yl]-ethyl}-cyclohexyl)-2-(R)-tetrahydro-pyran-2-yl-acetamide;
- N-trans-(4-{2-[4-(6-Chloro-benzo[d]isoxazol-3-yl)-piperazin-1-yl]-ethyl}-cyclohexyl)-2-(S)-tetrahydro-pyran-2-yl-acetamide;
- N-trans-(4-{2-[4-(6-Chloro-benzo[d]isoxazol-3-yl)-piperazin-1-yl]-ethyl}-cyclohexyl)-2-(4-isopropoxy-cyclohexyl)-acetamide;
- N-trans-(4-{2-[4-(6-Chloro-benzo[d]isoxazol-3-yl)-piperazin-1-yl]-ethyl}-cyclohexyl)-2-cyclopropyl-acetamide;
- N-trans-(4-{2-[4-(6-Chloro-benzo[d]isoxazol-3-yl)-piperazin-1-yl]-ethyl}-cyclohexyl)-3,3,3-trifluoro-propionamide;
- 4-trans-Methoxy-cyclohexanecarboxylic acid N-trans-(4-{2-[4-(6-chloro-benzo[d]isoxazol-3-yl)-piperazin-1-yl]-ethyl}-cyclohexyl)-amide; and
- N-trans-(4-{2-[4-(6-Chloro-benzo[d]isoxazol-3-yl)-piperazin-1-yl]-ethyl}-cyclohexyl)-3,3-dimethoxy-propionamide.

29. The compound of claim 1 selected from the group consisting of:
- N-trans-(4-{2-[4-(5,6-Difluoro-benzo[d]isoxazol-3-yl)-piperazin-1-yl]-ethyl}-cyclohexyl)-acetamide;
- N-trans-(4-{2-[4-(5,6-Difluoro-benzo[d]isoxazol-3-yl)-piperazin-1-yl]-ethyl}-cyclohexyl)-3-methoxy-propionamide;
- N-trans-(4-{2-[4-(5,6-Difluoro-benzo[d]isoxazol-3-yl)-piperazin-1-yl]-ethyl}-cyclohexyl)-2-trans-(4-methoxy-cyclohexyl)-acetamide;
- N-trans-(4-{2-[4-(5,6-Difluoro-benzo[d]isoxazol-3-yl)-piperazin-1-yl]-ethyl}-cyclohexyl)-propionamide;
- N-trans-(4-{2-[4-(5,6-Difluoro-benzo[d]isoxazol-3-yl)-piperazin-1-yl]-ethyl}-cyclohexyl)-2-methoxy-acetamide;
- N-trans-(4-{2-[4-(5,6-Difluoro-benzo[d]isoxazol-3-yl)-piperazin-1-yl]-ethyl}-cyclohexyl)-2-(4-hydroxy-tetrahydro-pyran-4-yl)-acetamide;
- N-trans-(4-{2-[4-(5,6-Difluoro-benzo[d]isoxazol-3-yl)-piperazin-1-yl]-ethyl}-cyclohexyl)-2-(4-methoxy-tetrahydro-pyran-4-yl)-acetamide;
- N-trans-(4-{2-[4-(5,6-Difluoro-benzo[d]isoxazol-3-yl)-piperazin-1-yl]-ethyl}-cyclohexyl)-2-(tetrahydro-pyran-4-yl)-acetamide;
- N-trans-(4-{2-[4-(5,6-Difluoro-benzo[d]isoxazol-3-yl)-piperazin-1-yl]-ethyl}-cyclohexyl)-3-hydroxy-3-methyl-butyramide;
- N-trans-(4-{2-[4-(5,6-Difluoro-benzo[d]isoxazol-3-yl)-piperazin-1-yl]-ethyl}-cyclohexyl)-2-trans-(3-methoxy-cyclopentyl)-acetamide; and
- 4-Methoxy-cyclohexanecarboxylic acid N-trans-(4-{2-[4-(5,6-difluoro-benzo[d]isoxazol-3-yl)-piperazin-1-yl]-ethyl}-cyclohexyl)-amide.

30. The compound of claim 1 selected from the group consisting of:
- Tetrahydro-pyran-4-carboxylic acid N-trans-(4-{2-[4-(5,6-difluoro-benzo[d]isoxazol-3-yl)-piperazin-1-yl]-ethyl}-cyclohexyl)-amide;
- Ethanesulfonic acid N-trans-(4-{2-[4-(5,6-difluoro-benzo[d]isoxazol-3-yl)-piperazin-1-yl]-ethyl}-cyclohexyl)-amide;
- N-trans-(4-{2-[4-(5,6-Difluoro-benzo[d]isoxazol-3-yl)-piperazin-1-yl]-ethyl}-cyclohexyl)-2-[1,3]dioxan-2-yl-acetamide;
- N-trans-(4-{2-[4-(6-Chloro-5-fluoro-benzo[d]isoxazol-3-yl)-piperazin-1-yl]-ethyl}-cyclohexyl)-propionamide;
- N-trans-(4-{2-[4-(6-Chloro-5-fluoro-benzo[d]isoxazol-3-yl)-piperazin-1-yl]-ethyl}-cyclohexyl)-3-methoxy-propionamide;
- N-trans-(4-{2-[4-(6-Chloro-5-fluoro-benzo[d]isoxazol-3-yl)-piperazin-1-yl]-ethyl}-cyclohexyl)-2-(tetrahydro-pyran-4-yl)-acetamide;
- N-trans-(4-{2-[4-(5-Chloro-6-fluoro-benzo[d]isoxazol-3-yl)-piperazin-1-yl]-ethyl}-cyclohexyl)-acetamide;
- N-trans-(4-{2-[4-(5-Chloro-6-fluoro-benzo[d]isoxazol-3-yl)-piperazin-1-yl]-ethyl}-cyclohexyl)-3-methoxy-propionamide;
- N-trans-(4-{2-[4-(5-Chloro-6-fluoro-benzo[d]isoxazol-3-yl)-piperazin-1-yl]-ethyl}-cyclohexyl)-2-cyclopropyl-acetamide;
- N-trans-(4-{2-[4-(5-Chloro-6-fluoro-benzo[d]isoxazol-3-yl)-piperazin-1-yl]-ethyl}-cyclohexyl)-2-[1,4]dioxan-2-yl-acetamide; and
- N-trans-(4-{2-[4-(5-Chloro-6-fluoro-benzo[d]isoxazol-3-yl)-piperazin-1-yl]-ethyl}-cyclohexyl)-2-[1,3]dioxan-2-yl-acetamide.

31. The compound of claim 1 selected from the group consisting of:
- N-trans-(4-{2-[4-(5-Chloro-6-fluoro-benzo[d]isoxazol-3-yl)-piperazin-1-yl]-ethyl}-cyclohexyl)-3,3-dimethoxy-propionamide;
- N-trans-(4-{2-[4-(5-Chloro-6-fluoro-benzo[d]isoxazol-3-yl)-piperazin-1-yl]-ethyl}-cyclohexyl)-2-trans-(3-hydroxymethyl-cyclobutyl)-acetamide;
- N-trans-(4-{2-[4-(5-Chloro-6-fluoro-benzo[d]isoxazol-3-yl)-piperazin-1-yl]-ethyl}-cyclohexyl)-2-trans-(3-methoxymethyl-cyclobutyl)-acetamide;
- N-trans-(4-{2-[4-(5-Chloro-6-fluoro-benzo[d]isoxazol-3-yl)-piperazin-1-yl]-ethyl}-cyclohexyl)-3-methylsulfanyl-propionamide;
- N-trans-(4-{2-[4-(5-Chloro-6-fluoro-benzo[d]isoxazol-3-yl)-piperazin-1-yl]-ethyl}-cyclohexyl)-2-(3-methyl-isoxazol-5-yl)-acetamide;
- 3-Chloro-cyclobutanecarboxylic acid N-trans-(4-{2-[4-(5-chloro-6-fluoro-benzo[d]isoxazol-3-yl)-piperazin-1-yl]-ethyl}-cyclohexyl)-amide;
- 5-Chloro-thiophene-2-carboxylic acid N-trans-(4-{2-[4-(5-chloro-6-fluoro-benzo[d]isoxazol-3-yl)-piperazin-1-yl]-ethyl}-cyclohexyl)-amide;
- 5-Methoxy-thiophene-2-carboxylic acid N-trans-(4-{2-[4-(5-chloro-6-fluoro-benzo[d]isoxazol-3-yl)-piperazin-1-yl]-ethyl}-cyclohexyl)-amide;
- N-trans-(4-{2-[4-(5-Chloro-6-fluoro-benzo[d]isoxazol-3-yl)-piperazin-1-yl]-ethyl}-cyclohexyl)-propionamide;
- N-trans-(4-{2-[4-(5-Chloro-6-fluoro-benzo[d]isoxazol-3-yl)-piperazin-1-yl]-ethyl}-cyclohexyl)-2-hydroxy-acetamide; and N-trans-(4-{2-[4-(5-Chloro-6-fluoro-benzo[d]isoxazol-3-yl)-piperazin-1-yl]-ethyl}-cyclohexyl)-2-trans-(4-methoxy-cyclohexyl)-acetamide.

32. The compound of claim 1 selected from the group consisting of:
N-trans-(4-{2-[4-(5-Chloro-6-fluoro-benzo[d]isoxazol-3-yl)-piperazin-1-yl]-ethyl}-cyclohexyl)-2-methanesulfonyl-acetamide;
N-trans-(4-{2-[4-(5-Chloro-6-fluoro-benzo[d]isoxazol-3-yl)-piperazin-1-yl]-ethyl}-cyclohexyl)-3-methanesulfonyl-propionamide;
N-trans-(4-{2-[4-(5-Chloro-6-fluoro-benzo[d]isoxazol-3-yl)-piperazin-1-yl]-ethyl}-cyclohexyl)-carbamic acid methyl ester;
Cyclobutanecarboxylic acid N-trans-(4-{2-[4-(5-chloro-6-fluoro-benzo[d]isoxazol-3-yl)-piperazin-1-yl]-ethyl}-cyclohexyl)-amide;
N-trans-(4-{2-[4-(5-Chloro-6-fluoro-benzo[d]isoxazol-3-yl)-piperazin-1-yl]-ethyl}-cyclohexyl)-3,3,3-trifluoro-propionamide;
N-trans-(4-{2-[4-(5,6-Dichloro-benzo[d]isoxazol-3-yl)-piperazin-1-yl]-ethyl}-cyclohexyl)-3-methoxy-propionamide;
Tetrahydro-pyran-4-carboxylic acid N-trans-(4-{2-[4-(5,6-dichloro-benzo[d]isoxazol-3-yl)-piperazin-1-yl]-ethyl}-cyclohexyl)-amide;
N-trans-(4-{2-[4-(5,6-Dichloro-benzo[d]isoxazol-3-yl)-piperazin-1-yl]-ethyl}-cyclohexyl)-2-trans-(4-methoxy-cyclohexyl)-acetamide;
N-trans-(4-{2-[4-(5,6-Dichloro-benzo[d]isoxazol-3-yl)-piperazin-1-yl]-ethyl}-cyclohexyl-2-(tetrahydro-pyran-4-yl)-acetamide;
3-Methoxy-N-trans-(4-{2-[4-(6-methyl-benzo[d]isoxazol-3-yl)-piperazin-1-yl]-ethyl}-cyclohexyl)-propionamide; and
N-trans-(4-{2-[4-(6-Methyl-benzo[d]isoxazol-3-yl)-piperazin-1-yl]ethyl}-cyclohexyl)-propionamide.

33. The compound of claim 1 selected from the group consisting of:
2-trans-(4-Methoxy-cyclohexyl)-N-trans-(4-{2-[4-(6-methyl-benzo[d]isoxazol-3-yl)-piperazin-1-yl]-ethyl}-cyclohexyl)-acetamide;
2-[1,3]Dioxan-2-yl-N-trans-(4-{2-[4-(6-methyl-benzo[d]isoxazol-3-yl)-piperazin-1-yl]-ethyl}-cyclohexyl)-acetamide;
2-[1,4]Dioxan-2-yl-N-trans-(4-{2-[4-(6-methyl-benzo[d]isoxazol-3-yl)-piperazin-1-yl]-ethyl}-cyclohexyl)-acetamide;
3,3-Dimethoxy-N-trans-(4-{2-[4-(6-methyl-benzo[d]isoxazol-3-yl)-piperazin-1-yl]-ethyl}-cyclohexyl)-propionamide;
3-Methoxy-N-trans-(4-{2-[4-(5-methyl-benzo[d]isoxazol-3-yl)-piperazin-1-yl]-ethyl}-cyclohexyl)-propionamide;
N-trans-(4-{2-[4-(6-Fluoro-5-methyl-benzo[d]isoxazol-3-yl)-piperazin-1-yl]-ethyl}-cyclohexyl)-acetamide;
N-trans-(4-{2-[4-(6-Fluoro-5-methyl-benzo[d]isoxazol-3-yl)-piperazin-1-yl]-ethyl}-cyclohexyl)-2-methoxy-acetamide;
N-trans-(4-{2-[4-(6-Fluoro-5-methyl-benzo[d]isoxazol-3-yl)-piperazin-1-yl]-ethyl}-cyclohexyl)-3-methoxy-propionamide;
2-Cyclopropyl-N-trans-(4-{2-[4-(6-fluoro-5-methyl-benzo[d]isoxazol-3-yl)-piperazin-1-yl]-ethyl}-cyclohexyl)-acetamide;
2-Ethoxy-N-trans-(4-{2-[4-(6-fluoro-5-methyl-benzo[d]isoxazol-3-yl)-piperazin-1-yl]-ethyl}-cyclohexyl)-acetamide;
2-[1,3]Dioxan-2-yl-N-trans-(4-{2-[4-(6-fluoro-5-methyl-benzo[d]isoxazol-3-yl)-piperazin-1-yl]-ethyl}-cyclohexyl)-acetamide; and
N-trans-(4-{2-[4-(6-Fluoro-benzo[d]isoxazol-3-yl)-piperazin-1-yl]-ethyl}-cyclohexyl)-2-(tetrahydro-pyran-4-yl)-acetamide.

34. The compound of claim 1 selected from the group consisting of:
2-Methanesulfonyl-N-trans-(4-{2-[4-(6-methyl-benzo[d]isoxazol-3-yl)-piperazin-1-yl]-ethyl}-cyclohexyl)-acetamide;
2-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;
2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;
2-(S)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide;
(S)-4,4,4-Trifluoro-N-trans-(4-{2-[4-(6-fluoro-5-methyl-benzo[d]isoxazol-3-yl)-piperazin-1-yl]-ethyl}-cyclohexyl)-3-hydroxy-butyramide;
N-trans-(4-{2-[4-(6-Fluoro-5-methyl-benzo[d]isoxazol-3-yl)-piperazin-1-yl]-ethyl}-cyclohexyl)-2-(tetrahydro-pyran-2-yl)-acetamide;
N-trans-(4-{2-[4-(6-Fluoro-5-methyl-benzo[d]isoxazol-3-yl)-piperazin-1-yl]-ethyl}-cyclohexyl)-2-(tetrahydro-furan-2-yl)-acetamide; and
N-trans-(4-{2-[4-(6-Fluoro-5-methyl-benzo[d]isoxazol-3-yl)-piperazin-1-yl]-ethyl}-cyclohexyl)-2-methoxy-propionamide.

35. The compound of formula (I) according to claim 1 selected from the group consisting of:
2-Methanesulfonyl-N-trans-(4-{2-[4-(6-methyl-benzo[d]isoxazol-3-yl)-piperazin-1-yl]-ethyl}-cyclohexyl)-acetamide;
N-trans-(4-{2-[4-(6-Fluoro-5-methyl-benzo[d]isoxazol-3-yl)-piperazin-1-yl]-ethyl}-cyclohexyl)-acetamide;
N-trans-(4-{2-[4-(6-Fluoro-5-methyl-benzo[d]isoxazol-3-yl)-piperazin-1-yl]-ethyl}-cyclohexyl)-3-methoxy-propionamide; and
2-(R)-[1,4]Dioxan-2-yl-N-trans-(4-{2-[4-(6-fluoro-5-methyl-benzo[d]isoxazol-3-yl)-piperazin-1-yl]-ethyl}-cyclohexyl)-acetamide.

36. A pharmaceutical composition comprising a therapeutically effective amount of a compound of formula I

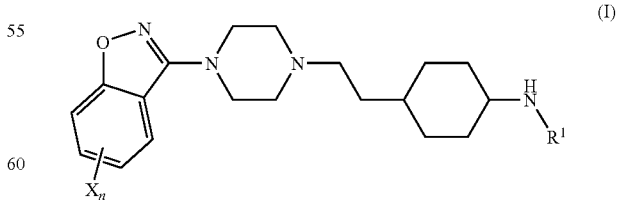

wherein:
X is independently halogen or $C_{1-6}$-alkyl;
n is 0, 1, or 2;
$R^1$ is —$COR^2$ or —$SO_2$—$C_{1-6}$-alkyl;

R² is $C_{1-6}$-alkyl, $C_{1-6}$-haloalkyl, $C_{1-6}$-hydroxyalkyl, $C_{1-6}$-alkoxy, 3 to 10 membered cycloalkyl, 4 to 10 membered heterocycloalkyl, or 5 to 10 membered heteroaryl, which are each optionally substituted by one or more substituents selected from the group consisting of:
halo,
hydroxy,
$C_{1-6}$-alkyl,
$C_{1-6}$-haloalkyl,
$C_{1-6}$-hydroxyalkyl,
$C_{1-6}$-alkoxy,
$C_{1-6}$-alkoxy optionally substituted by one or more $R^a$,
—S—$C_{1-6}$-alkyl,
—SO₂—$C_{1-6}$-alkyl,
—CONH₂,
—CHO,
3 to 10 membered cycloalkyl optionally substituted by one or more $R^a$,
4 to 10 membered heterocycloalkyl optionally substituted by one or more $R^a$, and
5 to 10 membered heteroaryl optionally substituted by one or more $R^a$;
wherein $R^a$ is selected from the group consisting of:
halo,
hydroxy,
$C_{1-6}$-alkyl,
$C_{1-6}$-hydroxyalkyl,
$C_{1-6}$-haloalkyl, and
$C_{1-6}$-alkoxy;
or a pharmaceutically acceptable salt thereof and a pharmaceutically acceptable carrier.

* * * * *